US010670559B2

United States Patent
Mannion et al.

(10) Patent No.: US 10,670,559 B2
(45) Date of Patent: Jun. 2, 2020

(54) NANOFLUIDIC CHANNELS WITH INTEGRATED CHARGE SENSORS AND METHODS BASED THEREON

(75) Inventors: John T. Mannion, Menlo Park, CA (US); Harold G. Craighead, Ithaca, NY (US)

(73) Assignee: Cornell University, Ithaca, NY (US)

( * ) Notice: Subject to any disclaimer, the term of this patent is extended or adjusted under 35 U.S.C. 154(b) by 863 days.

(21) Appl. No.: 13/003,490

(22) PCT Filed: Jul. 9, 2009

(86) PCT No.: PCT/US2009/050157
§ 371 (c)(1),
(2), (4) Date: May 17, 2011

(87) PCT Pub. No.: WO2010/044932
PCT Pub. Date: Apr. 22, 2010

(65) Prior Publication Data
US 2011/0227558 A1    Sep. 22, 2011

Related U.S. Application Data

(60) Provisional application No. 61/080,170, filed on Jul. 11, 2008.

(51) Int. Cl.
*H01L 29/66*    (2006.01)
*G01N 27/447*   (2006.01)
(Continued)

(52) U.S. Cl.
CPC .......... *G01N 27/4473* (2013.01); *B82Y 30/00* (2013.01); *G01N 33/48721* (2013.01);
(Continued)

(58) Field of Classification Search
CPC ....... B01L 2300/0896; B01L 3/502761; G01N 27/4146
See application file for complete search history.

(56) References Cited

U.S. PATENT DOCUMENTS 5,795,782 A    8/1998   Church et al.
6,123,819 A    9/2000   Peeters
(Continued)

FOREIGN PATENT DOCUMENTS

WO    WO 2008039579 A2 *    4/2008

OTHER PUBLICATIONS

Liang et al, Nanogap Detector Inside Nanofluidic Channel for Fast Real-Time Label-Free DNA Analaysis, Nano Letters, 2008 vol. 8, No. 5, p. 1472-1476.*
(Continued)

*Primary Examiner* — Son T Le
*Assistant Examiner* — Adam S Clarke
(74) *Attorney, Agent, or Firm* — Harris Beach PLLC; Laura W. Smalley

(57) ABSTRACT

An electrical detector is provided that comprises a nanofluidic channel with an integrated nanoscale charge sensor. The charge sensor can be an unfunctionalized nanowire, nanotube, transistor or capacitor and can be of carbon, silicon, carbon/silicon or other semiconducting material. The nanofluidic channel depth is on the order of the Debye screening length. Methods are also provided for detecting charged molecules or biological or chemical species with the electrical detector. Charged molecules or species in solution are driven through the nanofluidic channel of the electrical detector and contact the charge sensor, thereby producing a detectable signal. Methods are also provided for detecting a local solution potential of interest. A solution flowing through the nanofluidic channel of the electrical detector
(Continued)

Figure 1:
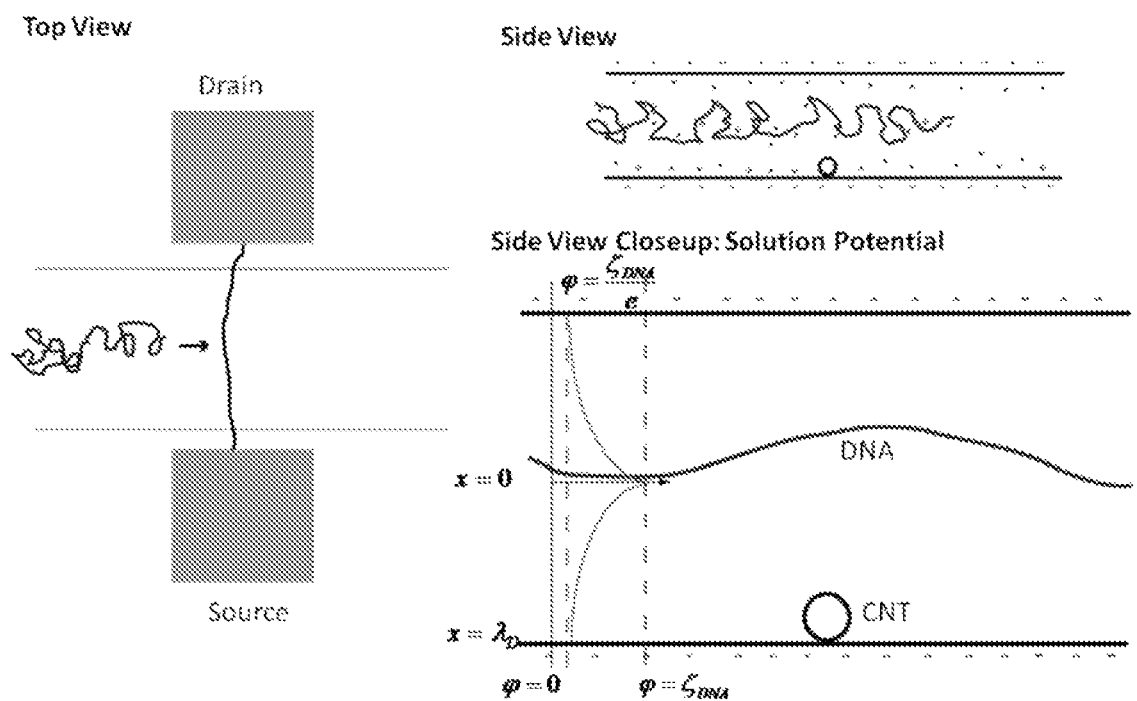

contacts the charge sensor, thereby producing a detectable local solution potential signal.

15 Claims, 35 Drawing Sheets

(51) Int. Cl.
| | | |
|---|---|---|
| *G01N 33/487* | (2006.01) | |
| *B82Y 30/00* | (2011.01) | |
| *B01L 3/00* | (2006.01) | |
| *G01N 27/414* | (2006.01) | |

(52) U.S. Cl.
CPC . *B01L 3/502761* (2013.01); *B01L 2300/0896* (2013.01); *G01N 27/414* (2013.01)

(56) References Cited

U.S. PATENT DOCUMENTS

| | | | |
|---|---|---|---|
| 6,325,904 B1 | 12/2001 | Peeters | |
| 6,362,002 B1 | 3/2002 | Denison et al. | |
| 6,413,792 B1 | 7/2002 | Sauer et al. | |
| 6,627,067 B1 | 9/2003 | Branton et al. | |
| 6,673,615 B2 | 1/2004 | Denison et al. | |
| 6,790,671 B1 | 9/2004 | Austin et al. | |
| 6,953,958 B2* | 10/2005 | Baxter et al. | 257/253 |
| 7,001,792 B2 | 2/2006 | Sauer et al. | |
| 7,235,184 B2 | 6/2007 | Dugas et al. | |
| 7,279,337 B2 | 10/2007 | Zhu | |
| 7,416,911 B2 | 8/2008 | Heath et al. | |
| 2002/0117659 A1* | 8/2002 | Lieber | B82Y 10/00 257/14 |
| 2003/0141189 A1* | 7/2003 | Lee | B01L 3/502761 204/600 |
| 2003/0231531 A1* | 12/2003 | Baxter | B82Y 10/00 365/200 |
| 2005/0212014 A1* | 9/2005 | Horibe et al. | 257/213 |
| 2006/0011862 A1 | 1/2006 | Bernstein | |
| 2006/0246497 A1 | 11/2006 | Huang et al. | |
| 2006/0275778 A1 | 12/2006 | Wu et al. | |
| 2006/0275779 A1 | 12/2006 | Li et al. | |
| 2007/0054276 A1 | 3/2007 | Sampson | |
| 2007/0122313 A1 | 5/2007 | Li et al. | |
| 2007/0161028 A1 | 7/2007 | Schwartz et al. | |
| 2007/0178507 A1 | 8/2007 | Wu et al. | |
| 2007/0190543 A1 | 8/2007 | Livak | |
| 2007/0238112 A1 | 10/2007 | Sohn et al. | |
| 2007/0259331 A1 | 11/2007 | Abeygunaratne | |
| 2007/0264623 A1 | 11/2007 | Wang et al. | |
| 2007/0292877 A1 | 12/2007 | Dimitrov | |
| 2008/0025875 A1* | 1/2008 | Martin et al. | 422/82.01 |
| 2008/0032290 A1 | 2/2008 | Young | |
| 2008/0063566 A1* | 3/2008 | Matsumoto | G01N 33/5438 422/68.1 |
| 2008/0171316 A1 | 7/2008 | Golovchenko et al. | |
| 2008/0242556 A1* | 10/2008 | Cao et al. | 506/9 |
| 2008/0247908 A1* | 10/2008 | Kahlman | B01L 3/502715 422/68.1 |
| 2008/0283939 A1* | 11/2008 | Choi et al. | 257/410 |
| 2009/0136958 A1 | 5/2009 | Gershow et al. | |
| 2009/0294303 A1* | 12/2009 | Fischer | B82Y 15/00 205/780.5 |
| 2010/0096268 A1* | 4/2010 | Ling et al. | 204/549 |
| 2010/0152057 A1* | 6/2010 | Lieber | B82Y 15/00 506/9 |

OTHER PUBLICATIONS

International Bureau of WIPO/Patent Cooperation Treaty, Notification Concerning Transmittal of International Preliminary Report on Patentability along with International Preliminary Report on Patentability for corresponding PCT Application No. PCT/US09/050157, dated Jan. 20, 2011, (6 pgs.).

International Searching Authority, PCT/ISA/220, Notification of Transmittal of the International Search Report and the Written Opinion of the International Searching Authority, or the Declaration, dated May 11, 2010 (4 pgs.).

Patent Cooperation Treaty, PCT/ISA/210 Interntional Search Report, dated May 11, 2010, (3 pgs.).

Patent Cooperation Treaty, PCT/ISA/237, Written Opinion of the International Searching Authority, dated May 11, 2010, (4 pgs.).

Kasianowicz, John J. et al., "Characterization of individual polynucleotide molecules using a membrane channel," Nov. 1996 Proc. Natl. Acad. Sci. USA, Biophysics, vol. 93 (pp. 13770-13773).

Meller Amit et al., "Rapid nanopore discrimination between single polynucleotide molecules," http://www.pnas.org/content/97/3/1079.full (pp. 1-10).

Menard, Jr., Laurent D. et al., "DNA Transport Characteristics in Focused Beam-Milled Nanofluidic Devices," Abstract, http://aiche,confex.com/aiche/2009/webprogrampreliminary/Paper160572.html (pp. 1-2).

Vartanian, Armand et al., "DNA Directed Construction of High Yield 2-D Nanowire Arrays," 2004, www.cs.caltech.edu/cbsss/finalreport/index.html (7 pages).

* cited by examiner

1. Fused Silica Wafer with Alignment Marks

2. Platinum Electrode Deposition

3. Co Catalyst Deposition

5. Carbon Nanotube Growth

6. Protective Nitride Layer

7. Cr Sacrificial Layer Deposition

8. Thick Nitride Capping Layer

10. Wet Etch of Cr Sacrificial Layer

11. Wet Etch of Protective Nitride

NANOFLUIDIC CHANNELS WITH INTEGRATED CHARGE SENSORS AND METHODS BASED THEREON

CROSS-REFERENCE TO RELATED APPLICATIONS

This application claims priority to and the benefit of U.S. provisional patent application Ser. No. 61/080,170, entitled "Nanofluidic Channels with Integrated Nanowires," filed Jul. 11, 2008, which is incorporated herein by reference in its entirety.

STATEMENT REGARDING FEDERALLY SPONSORED RESEARCH OR DEVELOPMENT

This invention was made with government support under grant number HG001506 awarded by the National Institutes of Health and grant number 9876771 awarded by the National Science Foundation. The government has certain rights in the invention.

1. TECHNICAL FIELD

The present invention relates to nanofluidic channels ("nanochannels") with integrated charge sensors such as nanotubes, nanowires, transistors or capacitors. The invention also relates to methods for detecting biological or chemical species in nanofluidic channels with charge sensors. The invention further relates to detecting local solution potential in nanofluidic channels with charge sensors. The invention also relates to methods for measuring conformation, length, speed or fluorescence intensity of charged molecules, in particular, biological or chemical species.

2. BACKGROUND OF THE INVENTION

2.1 Nanofluidic Channels as Detectors of Molecules of Interest

In recent years, nanofabricated, fluid-filled channels ("nanofluidic channels" or "nanochannels") and apertures have been investigated as tools for single biomolecule manipulation and detection. Nanochannels and nanoslits in particular have been used for the elongation and observation of fluorescently labeled DNA molecules. Fragment length analysis, restriction site mapping (Riehn, R., et al., Restriction mapping in nanofluidic devices. Proceedings of the National Academy of Sciences of the United States of America, 2005. 102(29): p. 10012-10016), and physical mapping of target motifs using bound probes (Phillips, K. M., et al., Application of single molecule technology to rapidly map long DNA and study the conformation of stretched DNA. Nucleic Acids Research, 2005. 33(18): p. 5829-5837) have all been demonstrated as a result of single molecule elongation. Much effort has been invested into understanding the physics of confinement induced elongation. DNA extension in such environments occurs because critical intramolecular length scales such as radius of gyration (commonly several 100s of nm) and persistence length (typically 60 nm) are comparable to the nanochannel diameter or the nanoslit depth (10-100 nm) (Tegenfeldt, J. O., et al., The dynamics of genomic-length DNA molecules in 100-nm channels. Proceedings of the National Academy of Sciences of the United States of America, 2004. 101(30): p. 10979-10983). The similarity in the size of the biomolecule and the length scale of the nanofabricated manipulator allows for single molecule control. Additionally, hydrodynamic coupling between DNA molecules and channel boundaries becomes more significant as channel size decreases. Greater hydrodynamic friction stabilizes molecules as they are being probed. This is an improvement as compared to the electrical detection of DNA molecules travelling through nanopores (Healy, K., B. Schiedt, and A. P. Morrison, Solid-state nanopore technologies for nanopore-based DNA analysis. Nanomedicine, 2007. 2(6): p. 875-897) for which thermal agitation is a major factor in limiting length measurement resolution.

2.2 Nanotubes and Nanowires as Charged Molecule Sensors

In addition to improvements in single molecule manipulation using nanochannels, much work has been done in a related area, detection of single molecules using nanotubes and nanowires.

Semiconducting nanowires have the ability to sense nearby, charged molecules in a solution. This is thought to occur either through field effect gating or through charge injection both of which cause a shift in the conductivity in the nanowire. Thus if a charged molecule is close enough to the nanowire, its presence will be noted by observing the nanowire conductivity. If the target molecule is far from the nanowire, however, then ions in solution can completely screen its charge from the point of view of the nanowire.

Nanotubes and nanowires have been shown to serve in the detection of biomolecules, even at the level of single protein binding and dissociation events (Patolsky, F., G. Zheng, and C. M. Lieber, Nanowire sensors for medicine and the life sciences. Nanomedicine, 2006. 1(1): p. 51-65; Patolsky, F., G. F. Zheng, and C. M. Lieber, Nanowire-based biosensors. Analytical Chemistry, 2006. 78(13): p. 4260-4269). The sensitivity of nanowires and nanotubes is attributed to the fact that they are commonly of the same size or even smaller than the molecules which they are detecting. Therefore, single charged and bound biomolecules can cause a shift in charge carrier concentration throughout the entire cross section of the wire. Additionally, for the case of single walled carbon nanotubes (SWCNTs) and DNA, the diameter of the nanotube can be nearly as small as the inter-base spacing in DNA (0.7 and 0.34 nm respectively) and smaller than the width of double stranded molecules (2 nm).

The length scale over which that charge is masked by ions in solution is called the ionic screening length. One of the key challenges in utilizing nanowires for detection, therefore, has been to force a molecule to be a distance from the nanowire that is roughly equal to, or less than, the ionic screening length. In the past, this has been achieved by causing the target molecule to chemically adhere to the nanowire surface, through functionalization of the surface, or some other means. If adhesion to the surface occurs, the target molecule is often within the screening length and may cause a shift in nanowire conductivity through the electric field effect. There are disadvantages to this, including but not limited to the fact that a nanowire may need to be functionalized with a specific chemical for each target molecule, or that it is difficult to functionalize certain types of nanowires at all.

2.3 Detection of Single DNA Molecules

Fluorescent observation of single DNA molecules elongated in nanochannels is well known in the art. It is possible, using fluorescent detection, to perform length measurements on single DNA fragments. Currently available "lab on chip" devices (e.g., from US Genomic Corporation) are designed to measure DNA fragment length. Such devices achieve this through an alternate route of fluorescence detection. No nanowires are used in these devices, nor are nanoscale channels used: only microscale channels are used.

There are several physical limitations to optical length detection measurements. First, to use optical detection, large pieces of optical equipment must be employed (microscopes, lamps or lasers, CCD detectors, etc.). In its standard state, this equipment often consumes the space on an entire optical table and much of it cannot be miniaturized, even in its most advanced and costly form. This severely limits product designers who would like to make portable, and low cost "lab-on-chip" devices. Second, the spatial resolution provided by optical systems is limited. Owing to the wave nature of light and the typical wavelengths used in fluorescent microscopy, the spatial resolution available using even the best optical systems is limited to around 200 nm. There are many interesting features in DNA molecules that are closer than 200 nm. The spacing between adjacent base pairs, for example, is 0.3 nm. The location of multiple hybridized probes on a DNA strand (a quantity which devices currently produced by U.S. Genomics determine), may be within a few nanometers of each other.

There is therefore a need in the art for a portable, low cost, and accurate "lab-on-chip" detector with spatial resolution for detecting the length of single molecules of interest. There is also a need for a detector comprising a charge sensor that detects molecules of interest at distances from the charge sensor that are roughly equal to, or less than, the ionic screening length. There is also a need in the art for a sensor in which molecules of interest do not chemically adhere to the sensor. There is further a need for a microchip or microdevice for the label-free electronic profiling of molecules of interest, e.g., microRNA expression in a single cell, with all processing steps integrated on the microchip.

Citation or identification of any reference in Section 2, or in any other section of this application, shall not be considered an admission that such reference is available as prior art to the present invention.

3. SUMMARY OF THE INVENTION

An electrical detector is provided comprising a nanofluidic channel and a charge sensor, wherein:
  the charge sensor is selected from the group consisting of nanowire, nanotube, transistor and capacitor, and
  a portion of the charge sensor is integrated in the nanofluidic channel, whereby the charge sensor is contacted by fluid in the nanofluidic channel.

In one embodiment, the portion of the charge sensor is disposed within, or on the surface of, the nanofluidic channel.

In another embodiment, the entire charge sensor is disposed within, or on the surface of, the channel.

In another embodiment, the electrical detector comprises charge sensor electrodes disposed within, or on the surface of, the channel.

In another embodiment, the electrical detector comprises a plurality of nanofluidic channels.

In another embodiment, the plurality of nanofluidic channels is 2-10, 10-50, 50-100, 100-500, 500-1000, or 1000-5000 channels.

In another embodiment, a portion of each of the plurality of charge sensors is integrated in the nanofluidic channel.

In another embodiment, the plurality of charge sensors is 2-10, 10-50, 50-100, or 100-500 sensors.

In another embodiment, the nanofluidic channel depth is on the order of the Debye screening length.

In another embodiment, the nanofluidic channel depth is smaller than the Debye screening length.

In another embodiment, the nanofluidic channel depth is 2-10 times the Debye screening length.

In another embodiment, the nanofluidic channel depth is 0.1 nm to 1 mm.

In another embodiment, the Debye screening length is 0.1 nm to 1000 nm.

In another embodiment, the Debye screening length is 10 nm.

In another embodiment, the width of the nanofluidic channel is 0.1 nm-1 nm, 1 nm-5 nm, 5 nm-10 nm, 10 nm-50 nm, 50 nm-100 nm, 100 nm-500 nm, 500 nm-1 μm, 1 μm-5 μm or 5 μm-10 μm.

In another embodiment, the nanotube is a p-type or n-type nanotube.

In another embodiment, the nanowire or nanotube comprises a semiconducting material.

In another embodiment, the nanowire or nanotube comprises carbon or silicon.

In another embodiment, the transistor is a field effect transistor (FET).

In another embodiment, the FET is a film disposed on a surface of the nanofluidic channel.

In another embodiment, the electrical detector comprises a microfluidic or macrofluidic structure fluidically connected to the nanofluidic channel.

In another embodiment, the microfluidic or macrofluidic structure is a reservoir or channel.

In another embodiment, the microfluidic or macrofluidic structure is selected from the group consisting of a cell sorting area, a filtering area, a separating area, a nucleic acid amplification area, a reaction area and a storage area.

In another embodiment, a molecule of interest (e.g., in solution or in the fluid in the nanofluidic channel) contacts the charge sensor.

In another embodiment, the molecule of interest does not contact the charge sensor.

In another embodiment, the molecule of interest is restrained or confined in close proximity to a sensing range of the charge sensor.

In another embodiment, the molecule of interest is label-free or unlabeled.

In another embodiment, the charge sensor is an addressable semiconducting charge sensor that behaves as an electrolyte gated field effect transistor.

In another embodiment, the charge sensor is nonfunctionalized.

In another embodiment, the charge sensor is functionalized.

In another embodiment, the charge sensor is functionalized with a molecule selected from the group consisting of an antibody (or portion thereof) and an oligonucleotide.

In a specific embodiment, the charge sensor is functionalized with a probe oligonucleotide that binds to a miRNA.

In another embodiment, the electrical detector comprises a substrate.

In another embodiment, the substrate is a semiconducting or insulated substrate.

In another embodiment, the substrate is comprises germanium or is germanium-based.

In another embodiment, the substrate comprises silicon (or a derivative thereof) or is silicon-based.

In another embodiment, the silicon-based substrate is selected from the group consisting of silicon, silica (silicon dioxide) and glass (e.g., borosilicate glass).

In another embodiment, the silica substrate is fused.

In another embodiment, the substrate is electrically insulated or comprises at least one electrically insulated surface.

In another embodiment, the substrate is transparent.

In another embodiment, the transparent substrate has a thickness compatible for use with a desired microscope objective for optical observation of a molecule of interest in the nanofluidic channel.

In another embodiment, the transparent substrate has a thickness of about 170 nm.

In another embodiment, optical observation of a molecule of interest in the nanofluidic channel is conducted in addition to electrical detection.

In another embodiment, change in charge sensor conductance is observed by applying a constant source-drain bias voltage with a constant source-drain bias voltage applicator (e.g., a voltage source and an ammeter) and monitoring the current through the charge sensor.

In another embodiment, the electrical detector comprises the constant source-drain bias voltage applicator.

In another embodiment, the bias voltage is selected from the group consisting of AC bias, periodic signal and non-periodic signal.

In another embodiment, the electrical detector comprises a source and drain electrode pair electrically connected to the charge sensor by electrical contacts.

In another embodiment, the electrical detector comprises an insulator insulating the electrical contacts of the source and drain electrode pair to the charge sensor.

In another embodiment, the electrical contacts are platinum.

In another embodiment, the insulator is silicon nitride.

In another embodiment, dimensions of the nanofluidic channel constrain or confine a molecule or particle of interest to within a sensing range of the charge sensor.

In another embodiment, the charge sensor is disposed in the channel in sufficiently close proximity to the constrained or confined molecule or particle of interest so as to avoid significant charge screening.

In another embodiment, the sensing range of the charge sensor is the diameter of the charge sensor plus twice the ionic screening length.

In another embodiment, the molecule or particle of interest is a charged molecule or particle.

In another embodiment, the charged molecule or particle is unassociated or free.

In another embodiment, the charged molecule or particle is bound to another entity.

In another embodiment, the charged molecule or particle is labeled or unlabeled (label-free).

In another embodiment, the molecule or particle of interest is a biological species, e.g., a virus, nucleic acid (e.g., DNA, RNA, miRNA), protein, cell, cell fragment or organelle, or is a fibrous particle, metal particle, or quantum dot.

In another embodiment, the molecule or particle of interest is detected, controlled or manipulated.

A method is also provided for detecting a biological or chemical species of interest or a tag associated with the species comprising:

providing the electrical detector;

flowing the species or an entity comprising the species through the nanofluidic channel of the electrical detector; and contacting the charge sensor with the species or the tag, thereby producing a detectable signal indicative of the presence of the biological or chemical species of interest.

In another embodiment, the species is in solution or the entity is a solution.

In another embodiment, the species is driven through the nanofluidic channel electrokinetically.

In another embodiment, the detectable signal is change in charge sensor conductance.

In another embodiment, the method comprises monitoring the charge sensor conductance.

In another embodiment, the method comprises visualizing the species near the charge sensor.

In a specific embodiment, the molecule of interest (or tag associated with the molecule of interest) is associated with a disease or disorder (e.g., cancer) and the method is used for screening for the disease or disorder.

In another embodiment, the method is used to carry out rapid length measurements and/or screening of nucleic acid (e.g., DNA) fragments.

A method is also provided for detecting a local solution potential of interest comprising:

providing the electrical detector;

flowing the solution through the nanofluidic channel of the electrical detector; and contacting the charge sensor with the solution, thereby producing a detectable local solution potential signal.

In one embodiment, the detectable signal is change in charge sensor conductance.

In another embodiment, the method comprises monitoring the charge sensor conductance.

A method is also provided for measuring conformation, length, speed or optically detectable feature, label or tag intensity of a single charged molecule or particle of interest comprising:

providing:
  a charged molecule or particle of interest with an optically detectable label (or feature, tag or modification),
  a nanoslit,
  a nanofluidic channel, and
  two spatially separated focal volumes defined by lasers focused sequentially on the nanochannel;

driving electrophoretically the charged molecule or particle from the nanoslit into the nanofluidic channel;

transporting the elongated charged molecule or particle through the two spatially separated focal volumes, thereby generating a first optically detectable signal and a second optically detectable signal shifted in time relative to each other;

detecting photon bursts (or photon count signals) from the first and second optically detectable signals;

measuring the photon bursts (or photon count signals) from the first and second optically detectable signals;

performing a speed or a cross correlation measurement using the measurement from the photon bursts (or photon count signals) from the first and second optically detectable signals; and calculating the conformation, length, speed or label intensity of the molecule or particle of interest from the speed or cross correlation measurement.

In one embodiment, the charged molecule or particle is confined and dynamically elongated beyond its equilibrium length in the nanochannel.

In another embodiment, the method comprising providing the electrical detector, wherein the electrical detector comprises the nanoslit and the nanofluidic channel.

In another embodiment, the optically detectable label is a fluorescent label.

In another embodiment, the method comprises:

providing a first optical fiber connected to a first photodiode and a second optical fiber connected to a second photodiode;

projecting an image from the first optically detectable signal on the first optical fiber;

projecting an image from the second optically detectable signal on the second optical fiber;

detecting the image from the first optically detectable signal with the first photodiode;

detecting the image from the second optically detectable signal with the second photodiode;

determining a number of emitted photons per channel length and time along the nanofluidic channel axis;

determining a resulting image at each optical fiber position; and measuring each optically detectable signal by determining a number of photons arriving at each photodiode.

In another embodiment, the method comprises analyzing the cross correlation function of the two measured optically detectable signal signals.

In another embodiment, the method comprises performing single-molecule burst analysis.

In another embodiment, calculating the conformation, length, speed or label intensity of the charged molecule or particle of interest comprises performing Gaussian fitting of logarithmic distributions.

In another embodiment, the electrical detector is a "lab on chip" device that is used to isolate, confine and otherwise manipulate molecules of interest.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

FIG. 1. An embodiment of the electrical detector comprising a nanofluidic channel with integrated charge sensor. Charge sensors such as nanowires, nanotubes, transistors or capacitors can be integrated into the nanofluidic channel. FIG. 1 (left side) is a top down view showing source and drain electrodes as grey squares. Thin horizontal lines indicate channel side walls. Dark black line indicates the charge sensor, in this embodiment, a carbon nanotube. The squiggled line depicts a DNA molecule that is moving along the nanofluidic channel in the direction of the channel axis, and will soon be on top of the nanotube. FIG. 1 (right side, top) is a side view of the device. In this particular embodiment, a nanowire charge sensor is disposed on the "floor" of the channel. The device can be flipped, however, so that the charge sensor is positioned on the "roof." Charged ions floating in the solution are shown as positive or negative signs. FIG. 1 (right side, bottom) shows that for sensing purposes, one parameter to be considered is the relation between the total depth of the nanochannel and the ionic screening length, i.e. the distance over which charged molecules are screened by other ions in solution.

Figure 2:
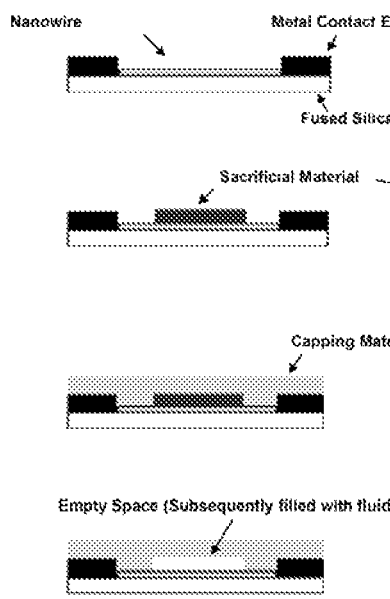
Figure 2:
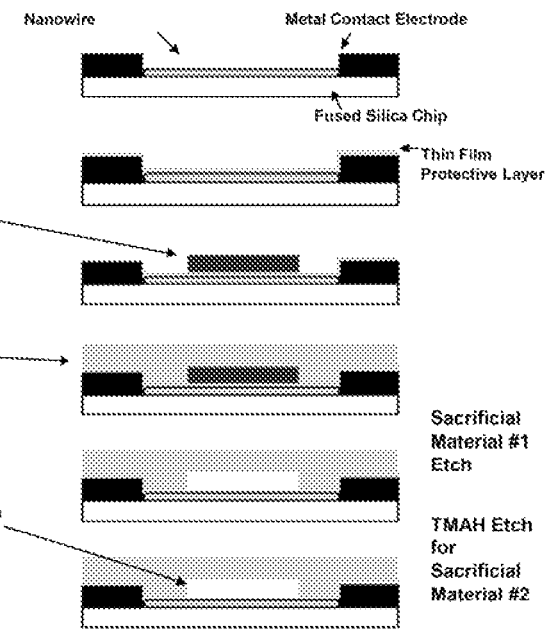
Figure 2:
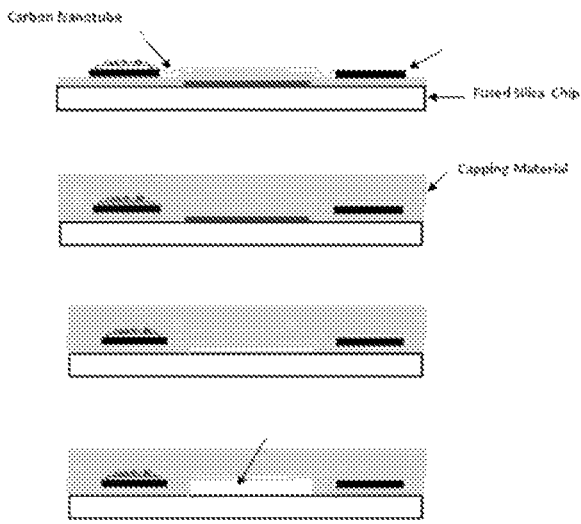

FIG. 2. Overview of the process by which charge sensors, e.g., nanowires, can be integrated into a nanofluidic channel.

Figure 3:
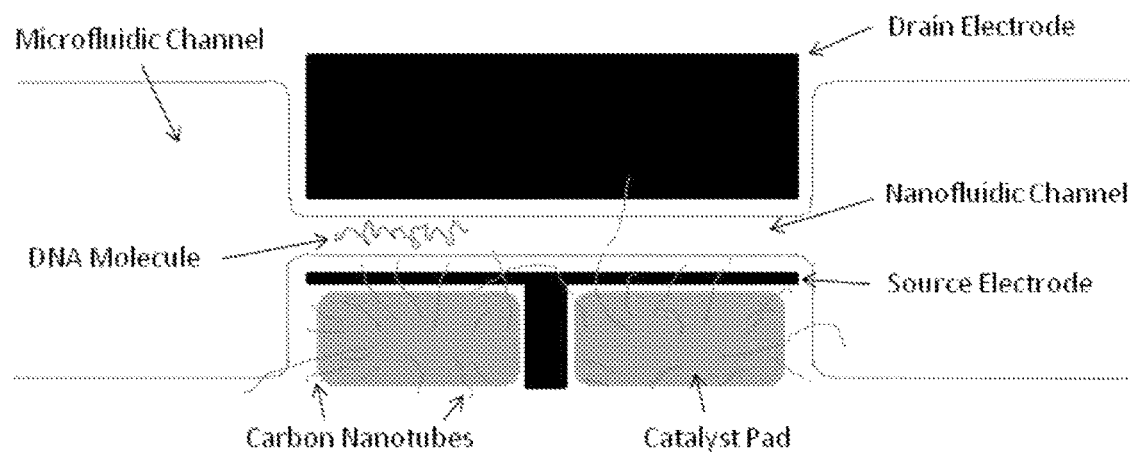

FIG. 3. Schematic diagram showing a top down view of the electrical detector and experimental procedure disclosed in Section 6.1.

Figure 4:
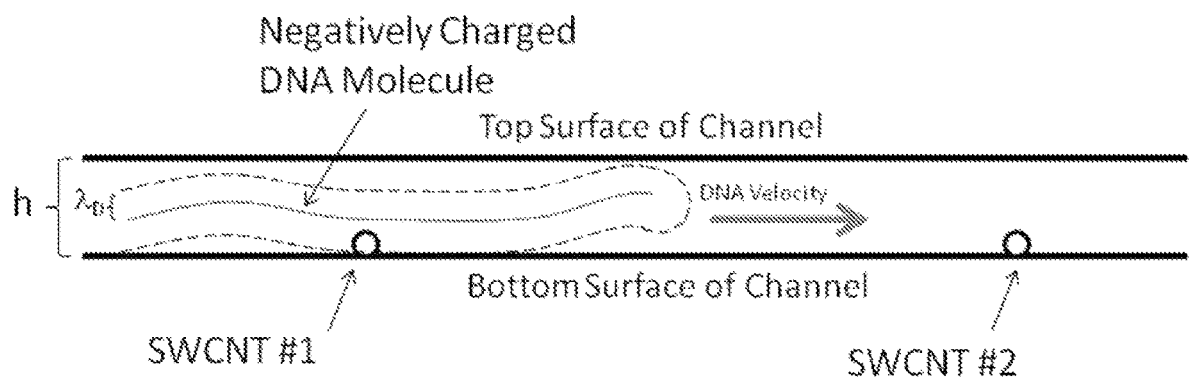

FIG. 4. Side view of electrical detector with a schematic of an elongated DNA molecule in the nanochannel. Two single walled carbon nanotubes (circular cross section shown) run perpendicular to the axis of the nanochannel and the image plane. A DNA molecule travelling through the nanochannel moves from left to right in the image. The negatively charged DNA molecule (curved solid line in middle of nanochannel) is surrounded by a cloud of positively charged ions. See Section 6.1 for details.

FIGS. 5A-B. A) Cross sectional diagram of a nanofluidic channel with integrated nanotube charge sensor. B) Band diagram of a p-type nanotube integrated into the electrical detector. See Section 6.1 for details.

FIGS. 6A-B. Diagrams illustrating the setup for electrolyte gate sweeps of carbon nanotubes and the resulting effects on band structure. The upper (black) band diagrams indicate an ungated, p-type nanotube. The lower (gray) band diagrams depict a shift (arrow) toward depletion as the gate voltage is made more positive relative to the source and drain. A) Unprotected nanotube source-drain contacts. B) Nanotube source drain contacts electrically isolated from the solution by some insulating layer. See Section 6.1 for details.

Figure 7:
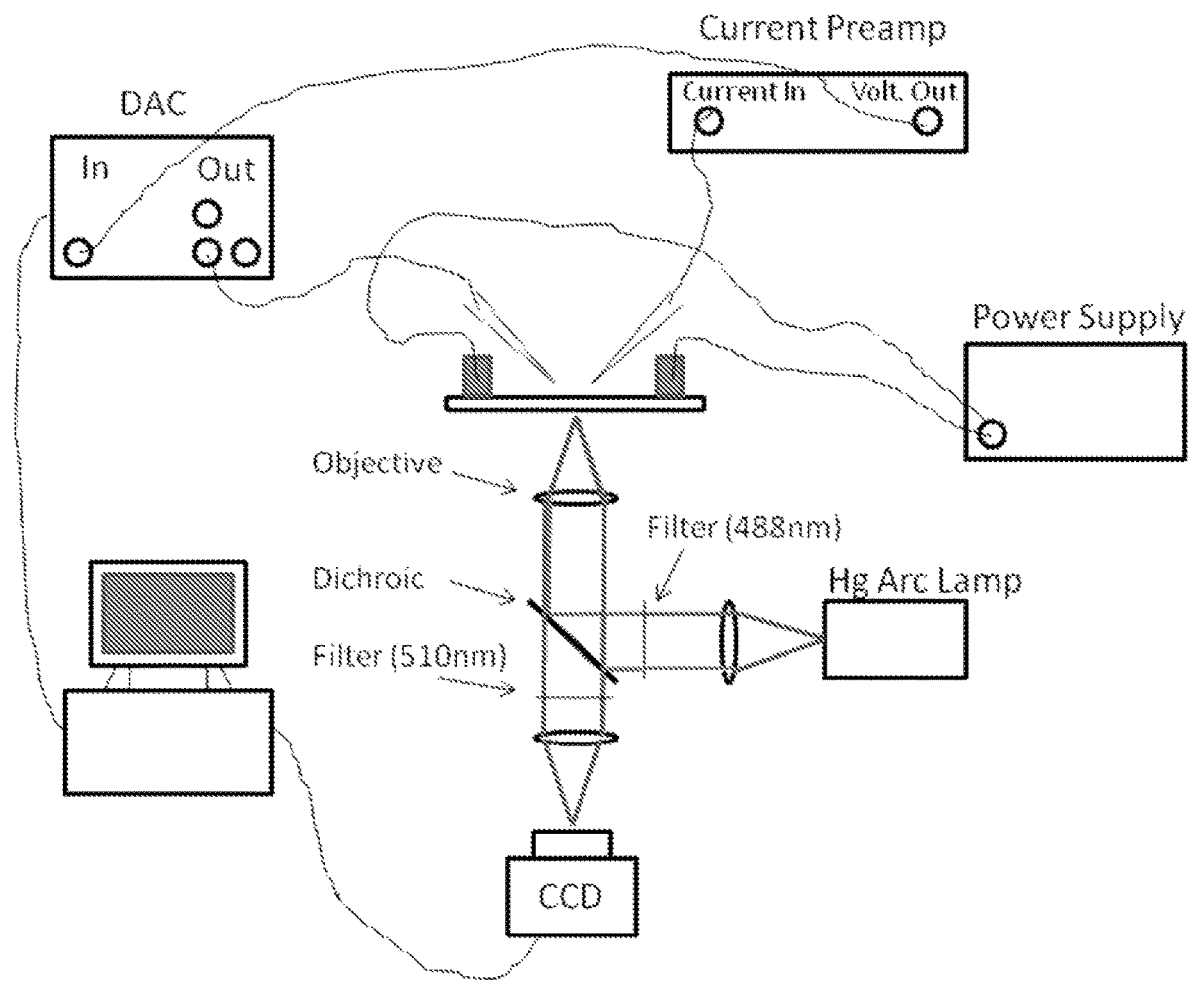

FIG. 7. Experimental setup for simultaneous optical and electrical detection. See Section 6.1 for details.

Figure 8A:
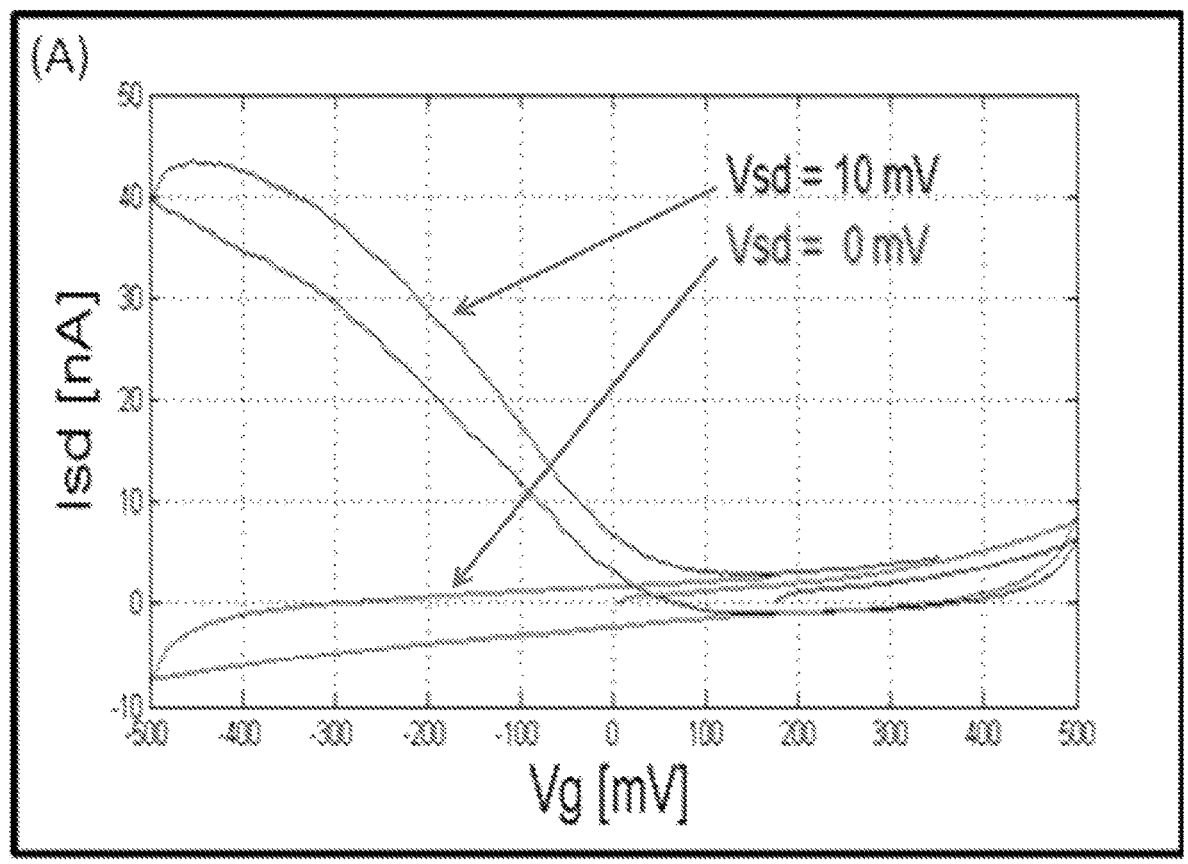
Figure 8B:
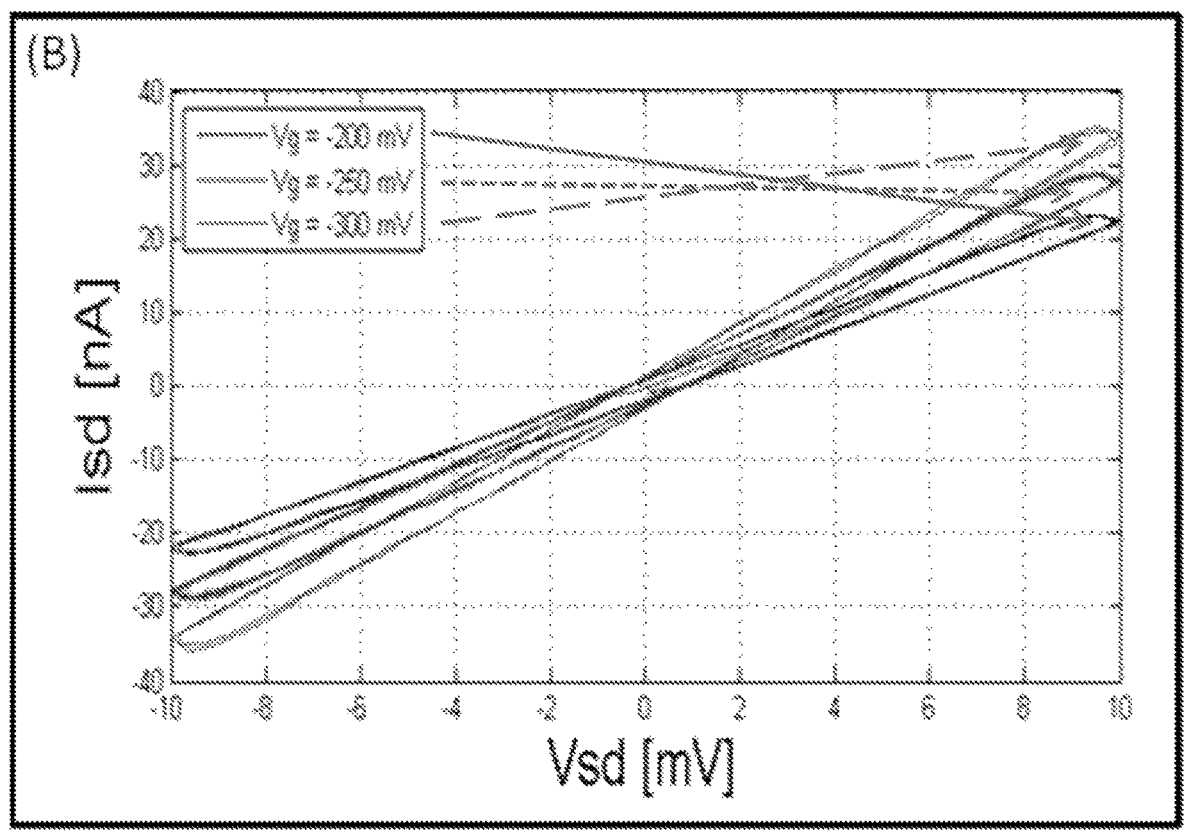

FIGS. 8A-B. A) Source drain current versus electrolyte gate sweep for two source drain voltages. B) Plot of current versus source-drain voltage for three different gate potentials. See Section 6.1 for details.

Figure 9:
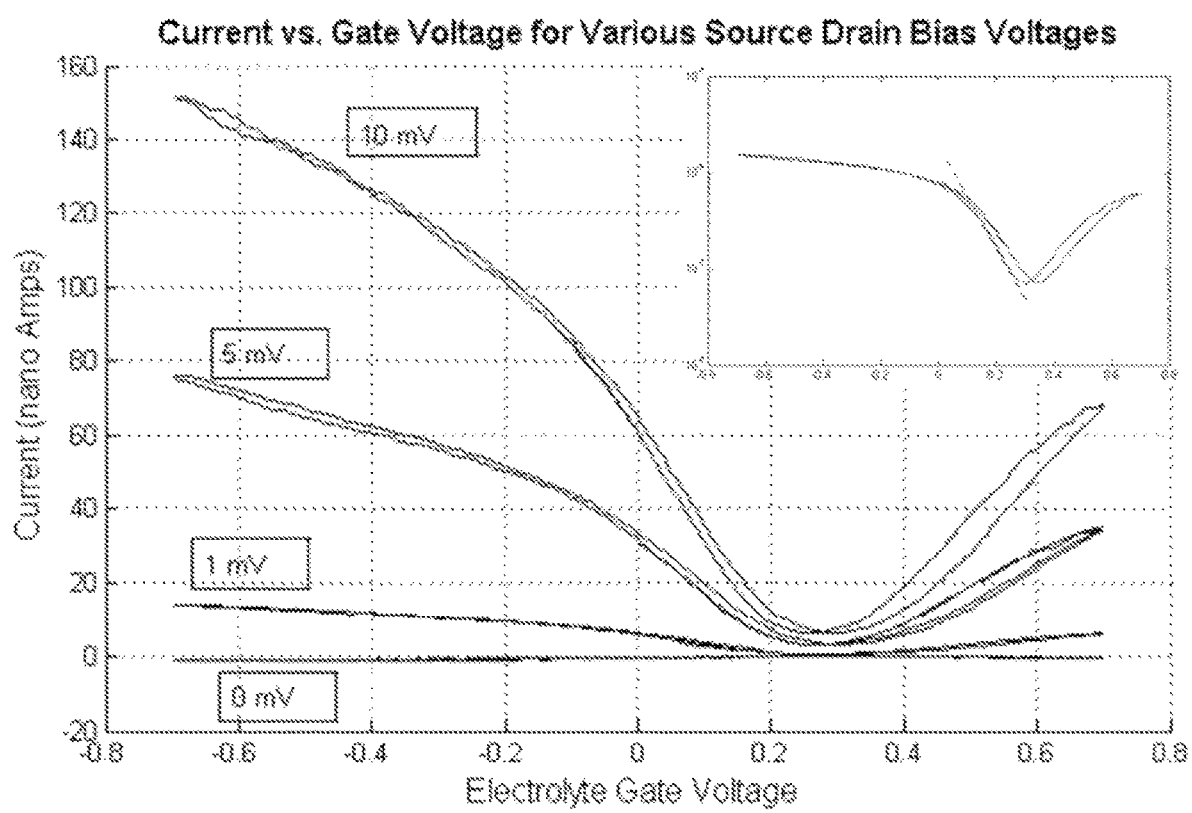

FIG. 9. Main panel: current versus electrolyte gate voltage at a variety of source-drain biases for a nanotube integrated into a nanofluidic channel of the electrical detector. Inset: semilog plot of current versus gate at 100 mV source drain bias. See Section 6.1 for details.

Figure 5:
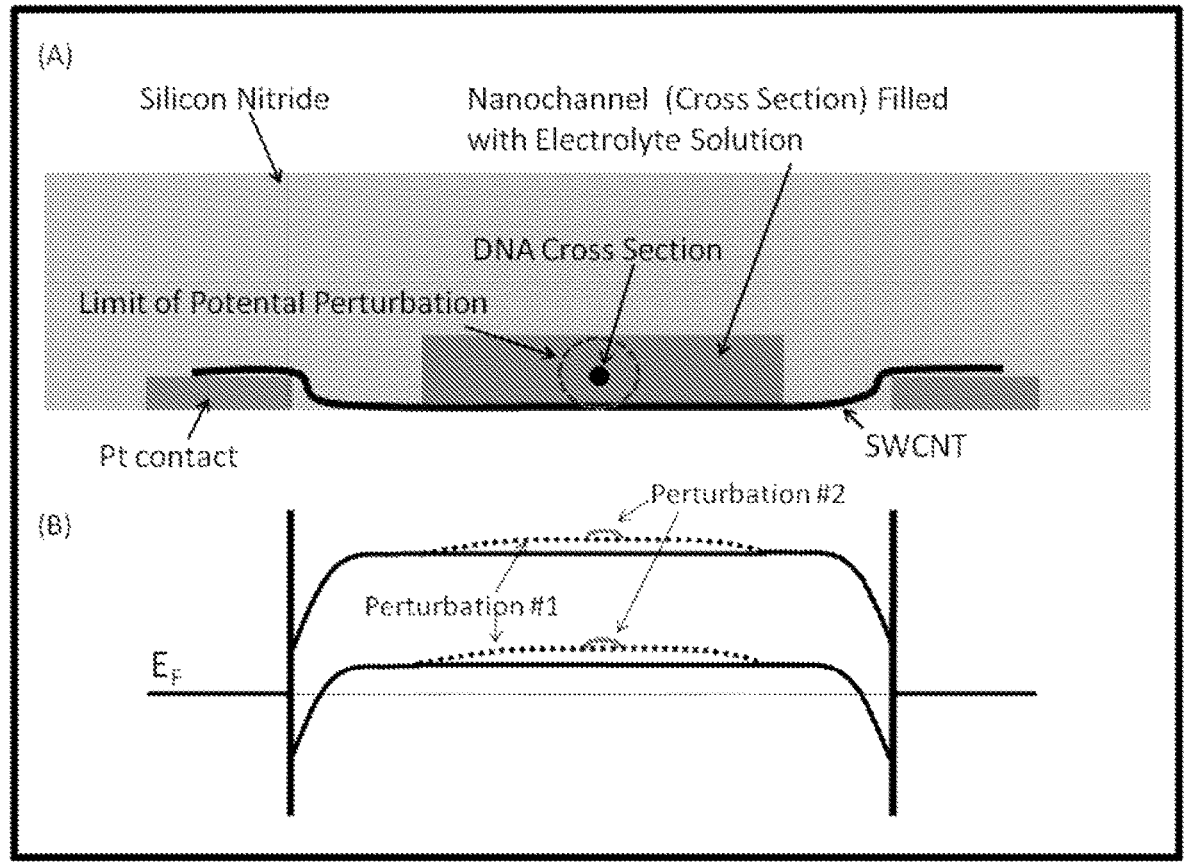
Figure 10:
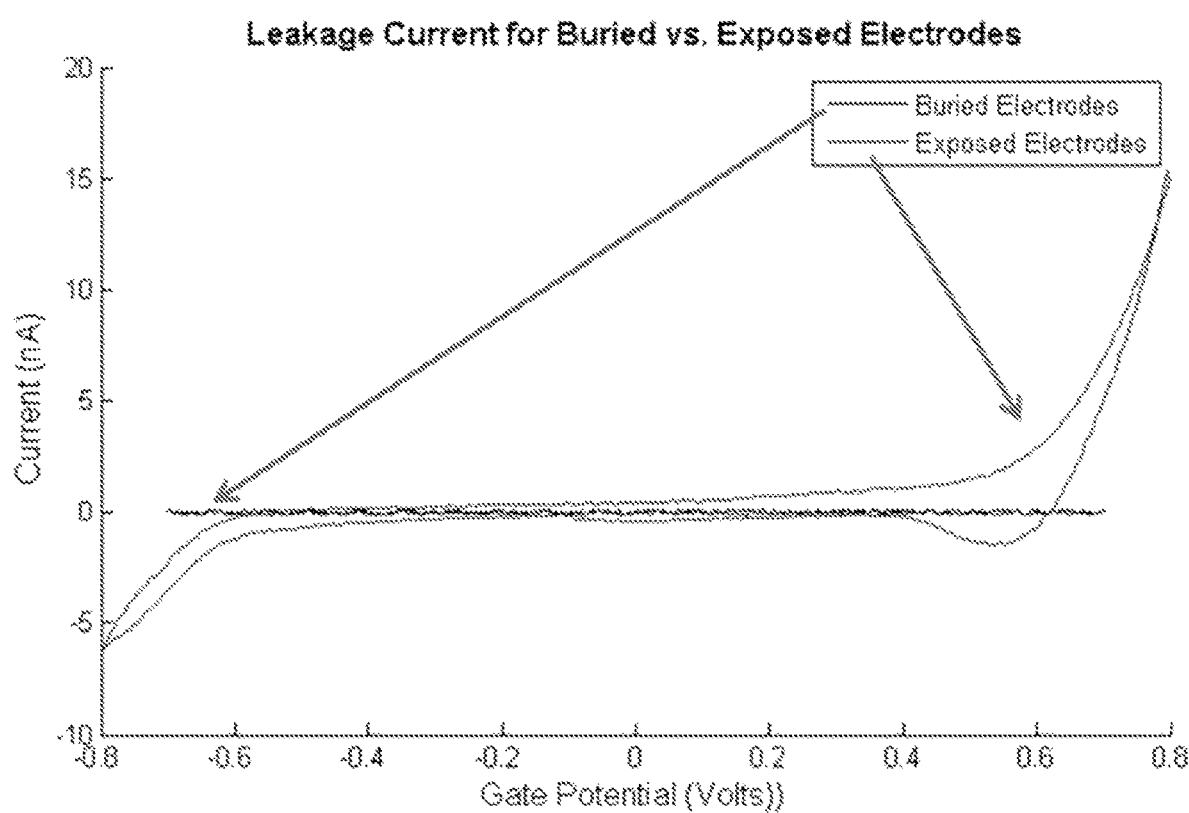
Figure 11A:
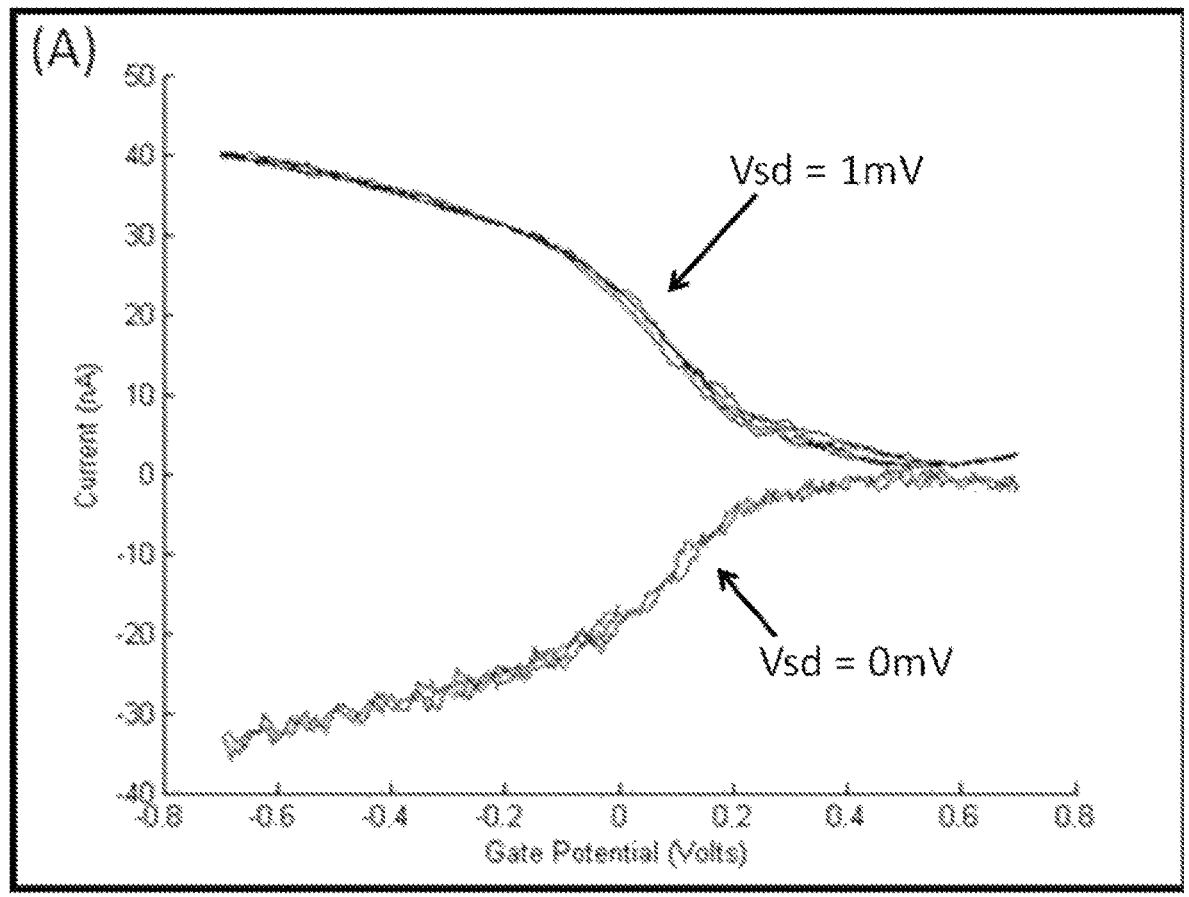
Figure 11B:
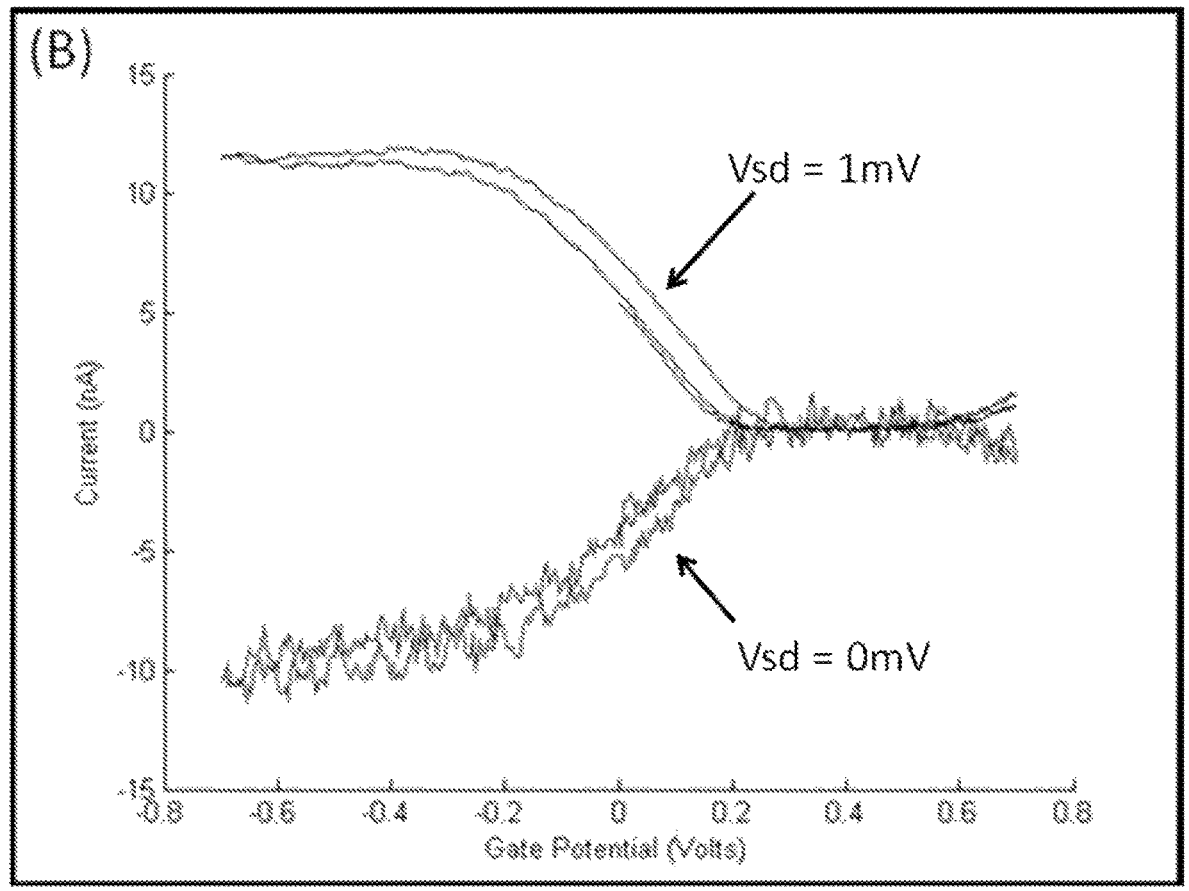
Figure 11C:
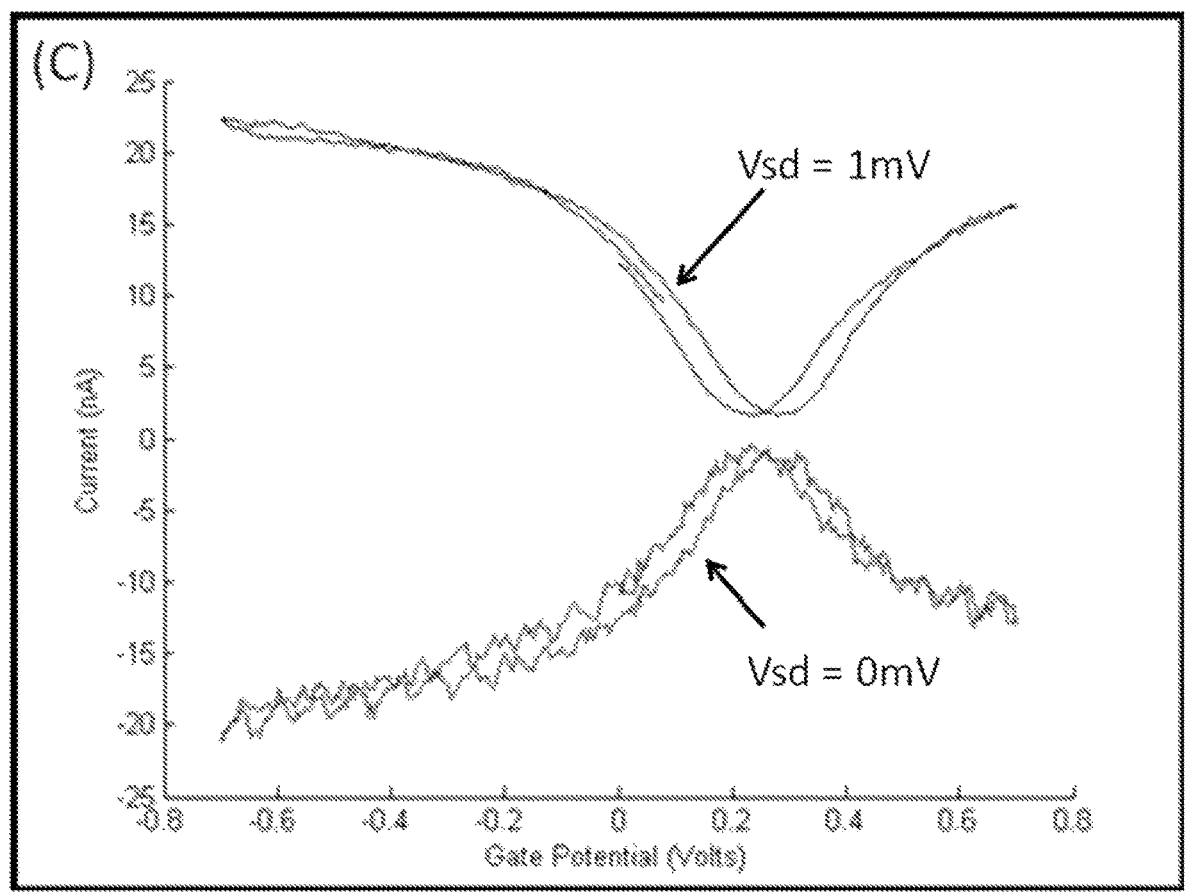
Figure 11D:
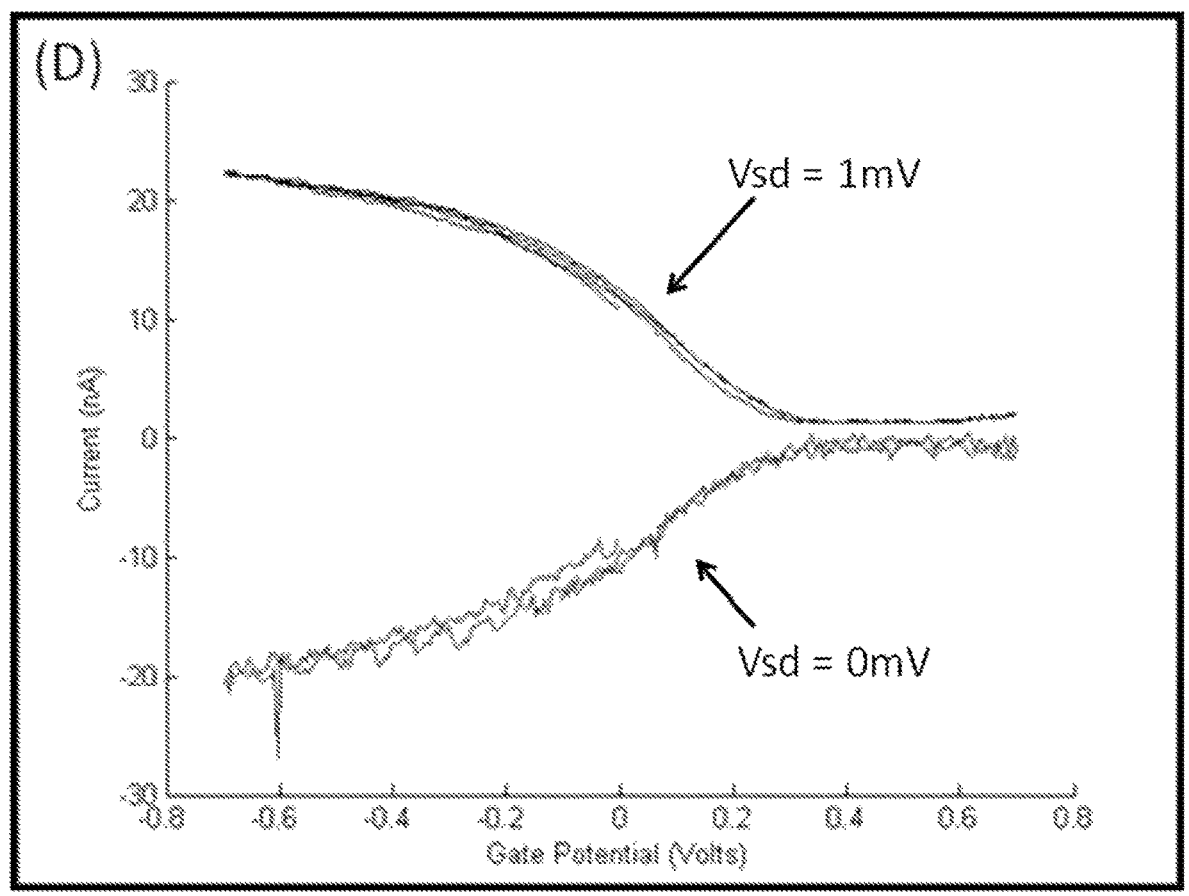

FIG. 10. Graph of leakage currents for buried versus exposed electrodes. Leakage currents between the gate and drain electrodes for two separate devices are graphed. As indicated in the figure, one data set is for a partially fabricated electrical detector, in which the source and drain electrodes were exposed and in contact with the electrolyte as in the diagram of FIG. 6A. The other data set is for a fully fabricated electrical detector, in which the source and drain electrodes were buried under silicon nitride and were separated from the electrolyte solution, as depicted in FIG. 5. See Section 6.1 for details.

FIGS. 11A-D. Plots of current versus gate potential for four different source drain electrode pairs for a fully fabricated electrical detector (i.e., contact electrodes covered by nitride). See Section 6.1 for details.

Figure 12:
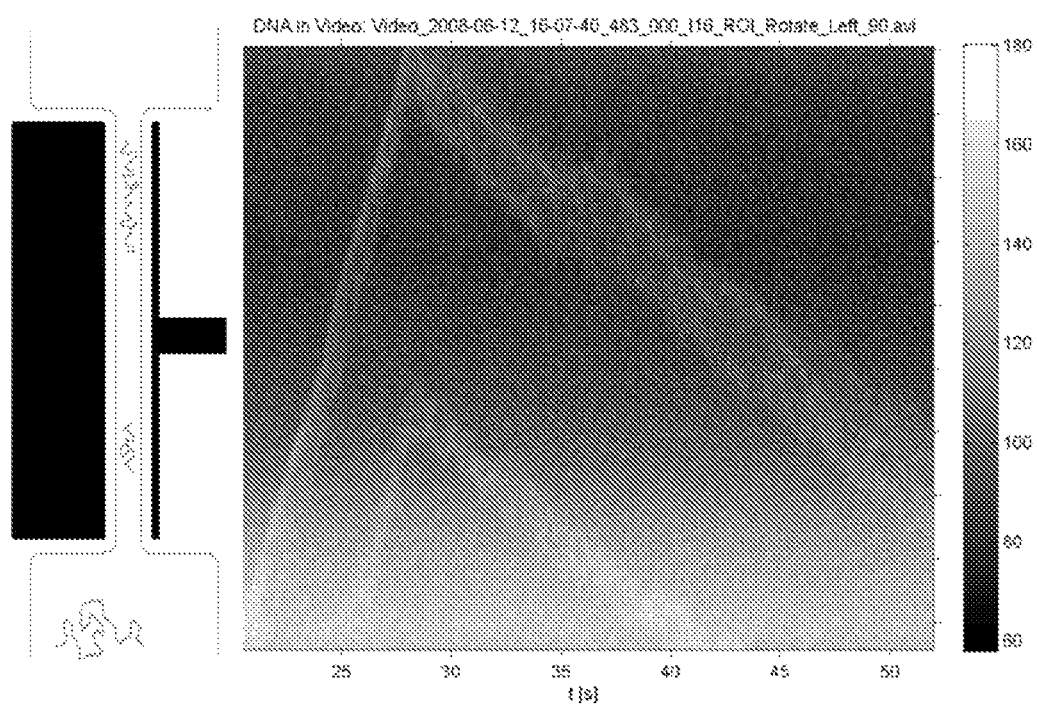

FIG. 12. Left: Schematic diagram of DNA molecules in and near the nanofluidic channel region of the electrical detector. In this diagram, two molecules are in the channel at the same time. By applying a small voltage (~1V), the molecules may be slowly driven up or down in the channel. Right: Time trace diagram of two DNA molecules in a nanochannel of an electrical detector comprising a carbon nanotube charge sensor. The first molecule enters the channel at time t=0 sec and the second molecule enters at t=25 sec. At t=29 sec, the direction of the electric field is reversed, causing the two molecules to change their direction of migration. See Section 6.1 for details.

Figure 13:
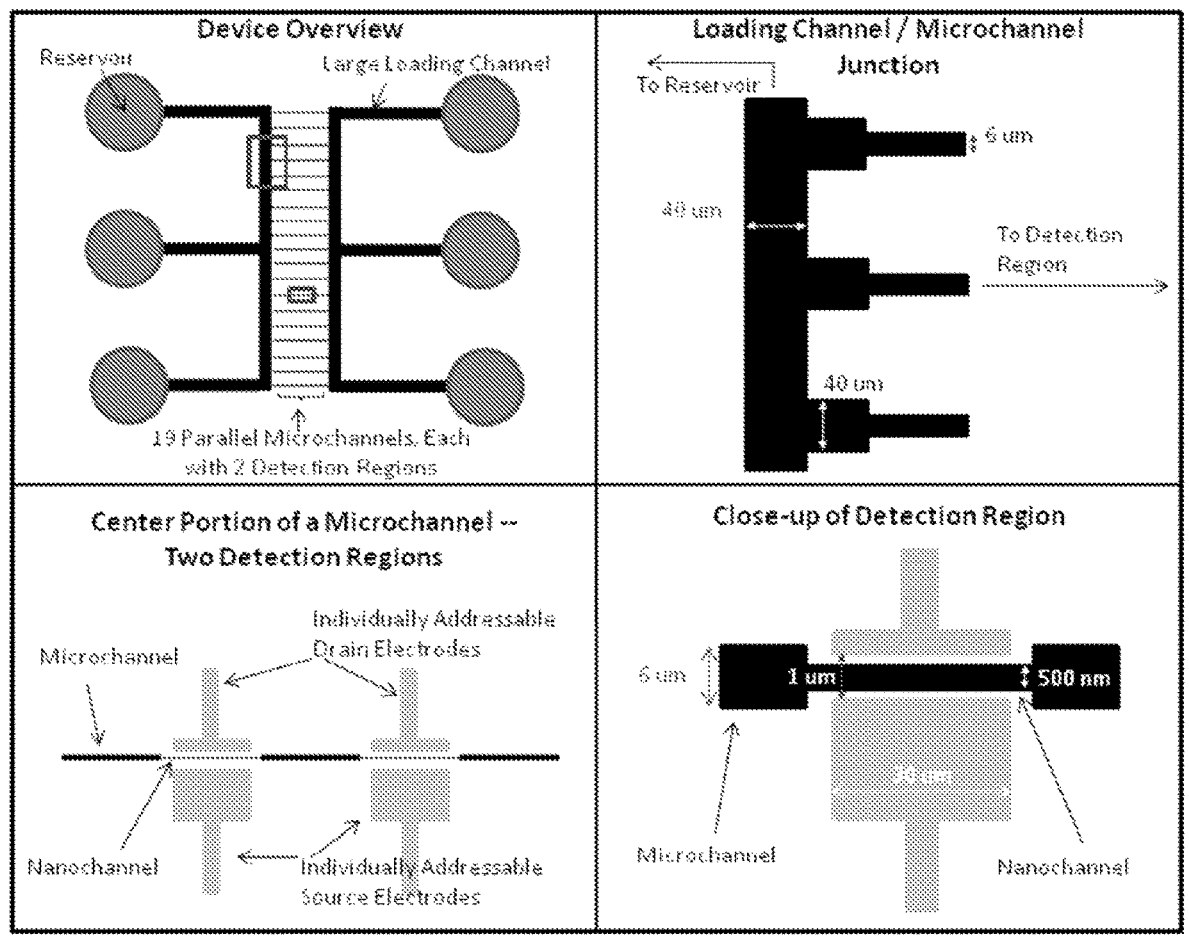

FIG. 13. Device diagrams of certain embodiments of the electrical detector. For ease of viewing, not all features within each image are drawn to scale relative to one another. Certain dimensions are indicated by arrows and labels. Top left panel: View of full fluidic network. Large circles represent the six macroscopic reservoirs for loading fluid and DNA. Thick black lines represent fluidic channels used for transporting DNA into the device from the reservoirs. Top right panel: Close-up of region where 3 microchannel branches connect to the larger loading channel. This corresponds to the large rectangle in A. Bottom left panel: Close up on middle portion of a microchannel branch. This corresponds to the small rectangle in A. As is drawn, two detection regions are present in each microchannel branch. Bottom right panel: Close-up of a detection region. Two platinum electrodes (a source and drain) are separated by a gap of 1 µm. See Section 6.2 for details.

Figure 14:
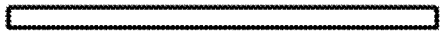
Figure 14:
Figure 14:
Figure 14:
Figure 14:
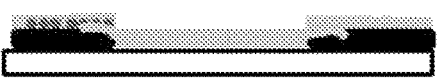
Figure 14:
Figure 14:
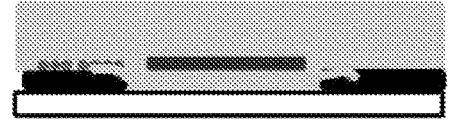
Figure 14:
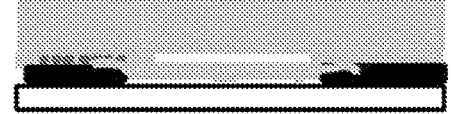
Figure 14:
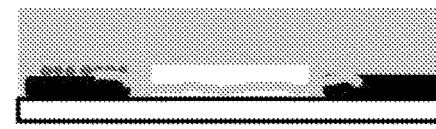

FIG. 14. Selected steps of the fabrication process described in Section 6.2. Each cross sectional image is labeled with its corresponding step number and name. See Section 6.2 for details.

Figure 15:
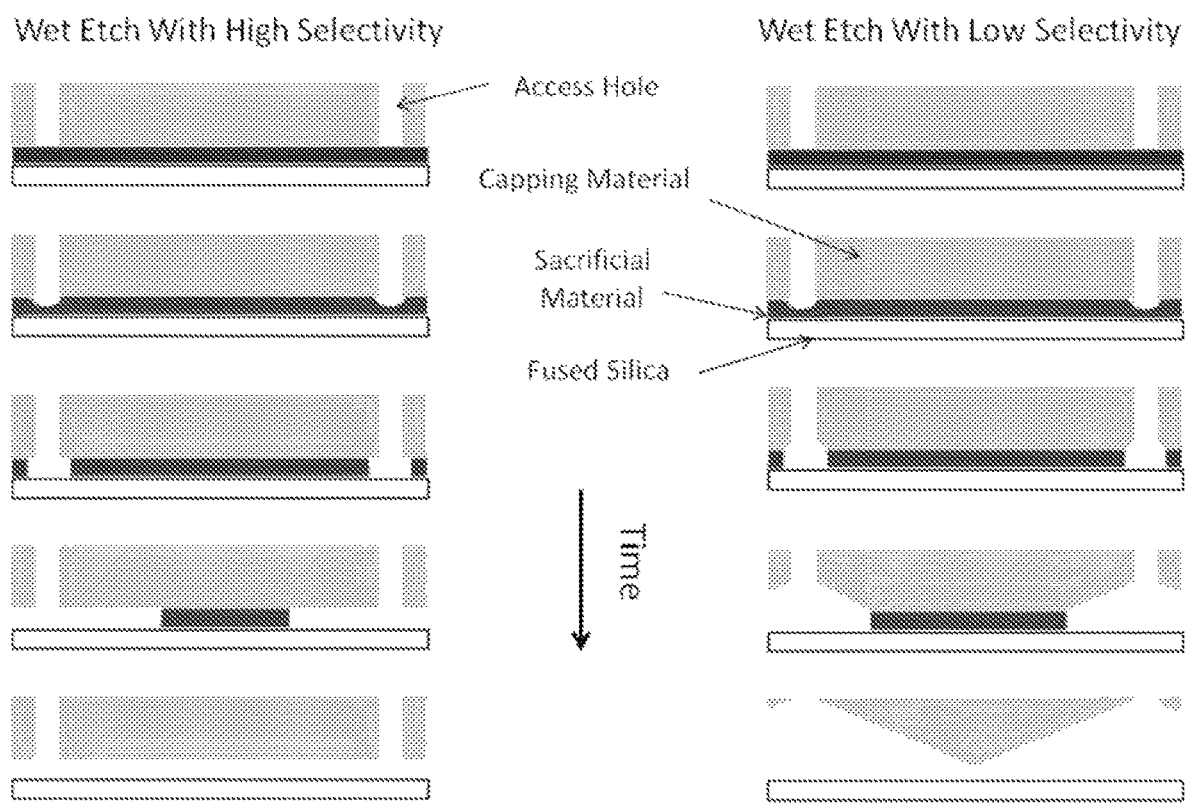

FIG. 15. Schematic diagram illustrating the importance of selectivity in sacrificial layer removal. Left Column) Channel depth is determined by sacrificial layer thickness only. Right Column) Channel depth is determined by sacrificial layer thickness plus amount of capping material etched. See Section 6.2 for details.

Figure 16:
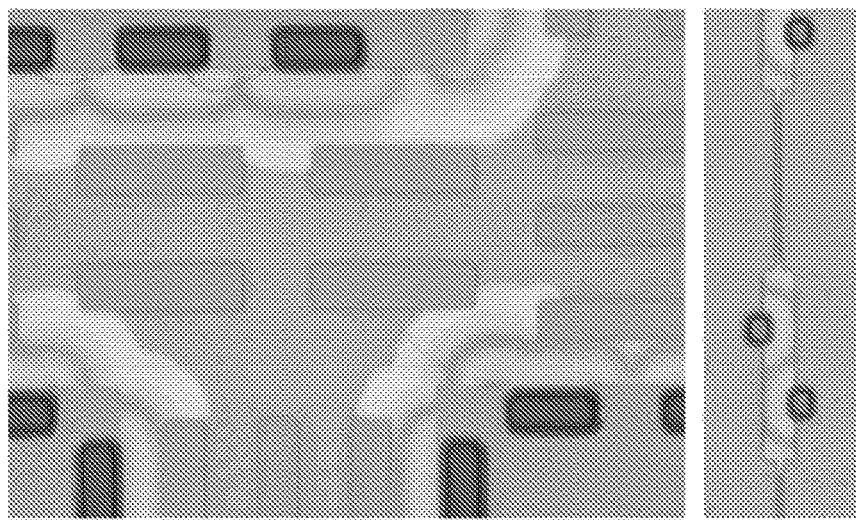

FIG. 16. Images of a-Si/Nitride based channels after partial removal of a-Si with TMAH etch. Access holes are the dark rectangles. The light gray areas are places where the a-Si sacrificial layer has not yet been etched away. See Section 6.2 for details.

Figure 17:
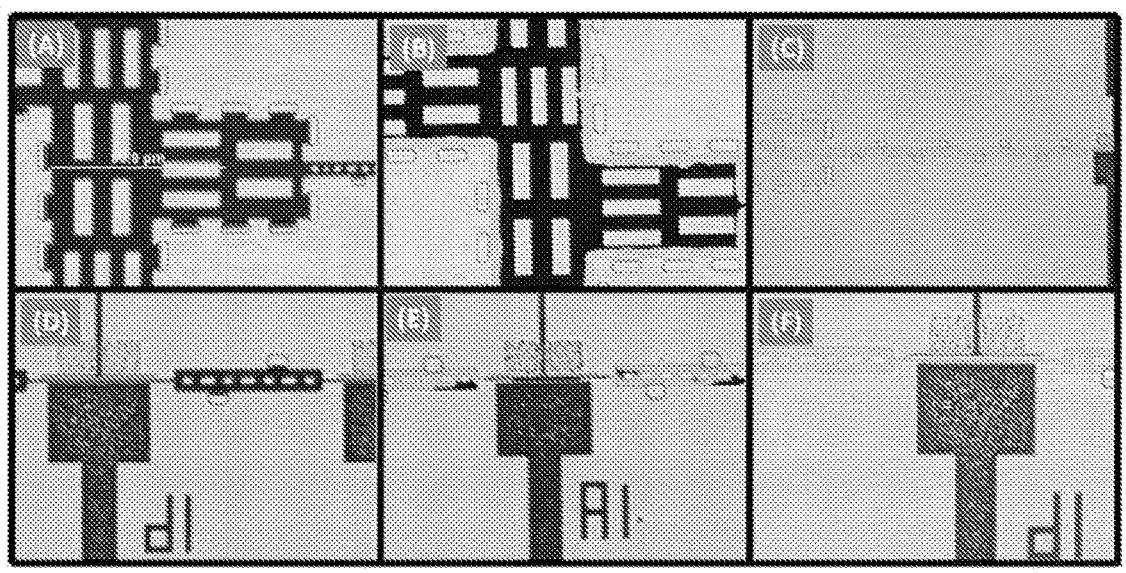

FIG. 17. Images of Cr/Nitride based channels after partial removal of Cr with Cr-14 Chromium Etchant. A-C) Images of microchannel region before etch, after 25 min, and after 3 hours. D-F) Close up of nanochannel region before etch, after 25 min, and after 3 hours. See Section 6.2 for details.

Figure 18:
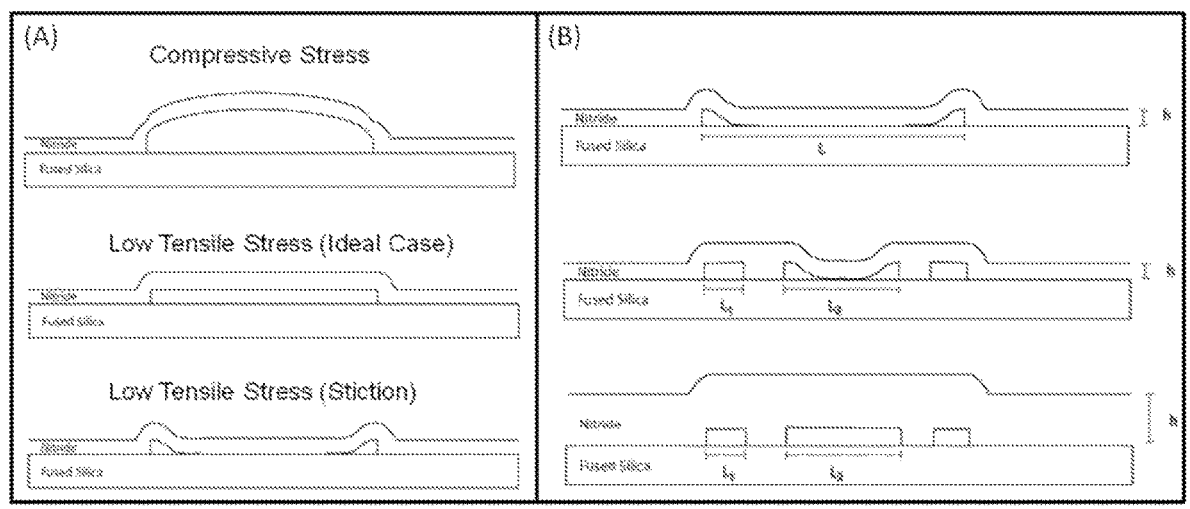

FIG. 18. Deformation of channel ceiling structure. A) Effect of stress on deformation. B) Effect of nitride thickness and width of channel spanned on deformation under a uniform load. See Section 6.2 for details.

Figure 19A:
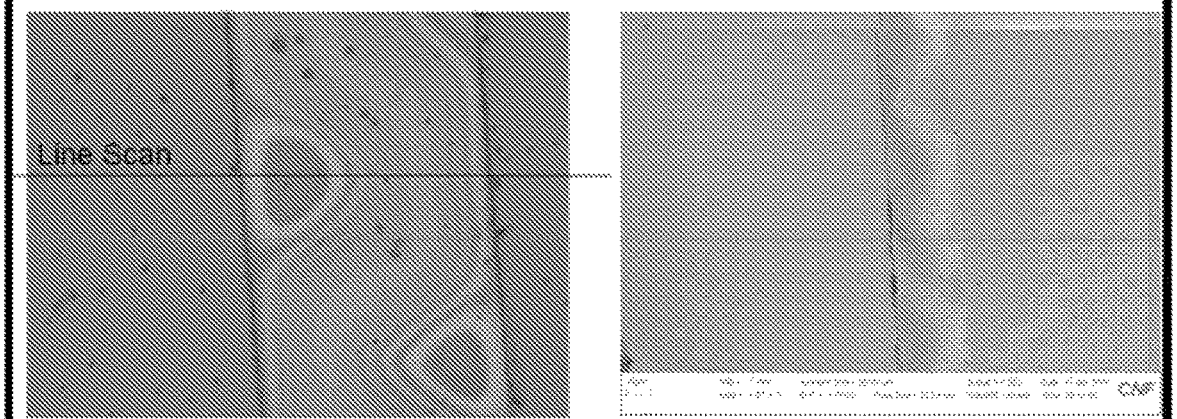
Figure 19B:
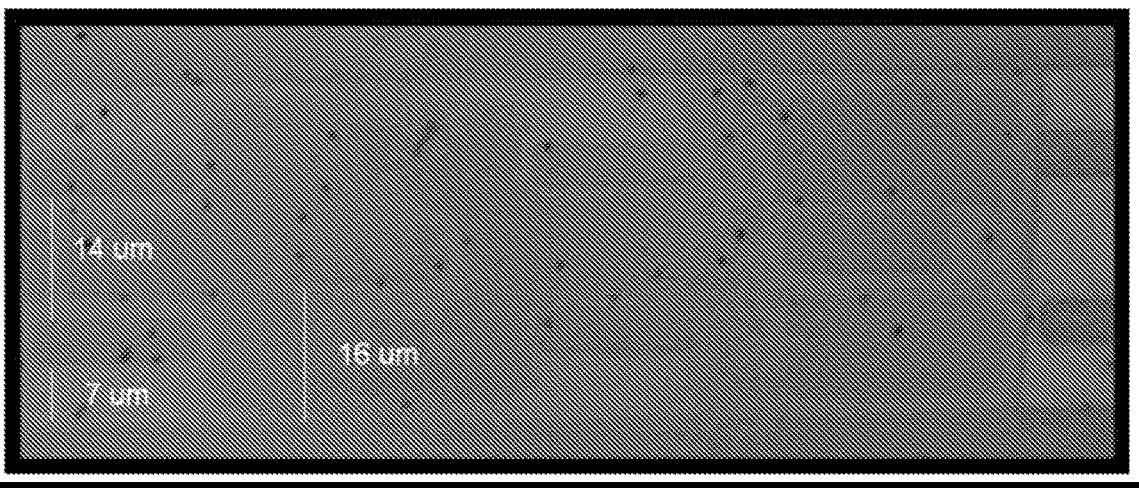
Figure 19C:
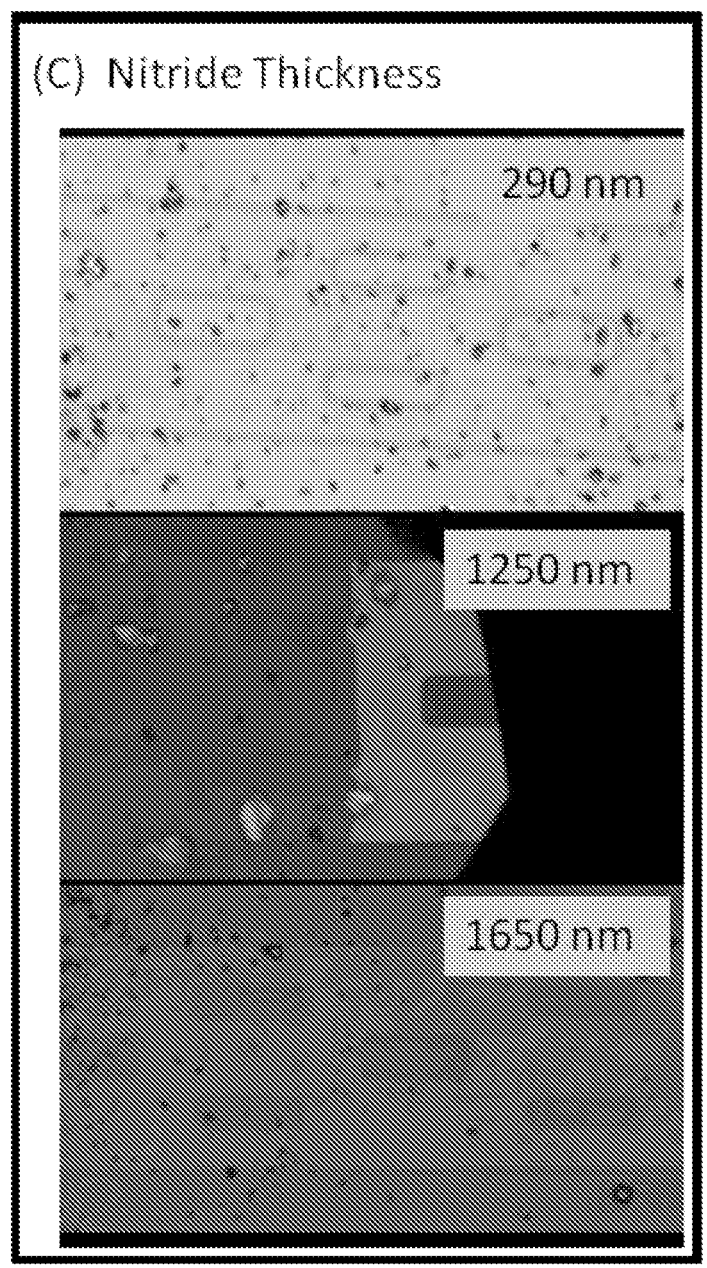

FIGS. 19A-C. Micrographs illustrating the effects of film stress, thickness and channel width on channel integrity. A) A 40 µm wide channel with no support columns. The left hand micrograph is an optical image in which variation in intensity results from variations in cavity height. The right hand image is an SEM micrograph of the same channel. The black line over the left image represents the location of a profilometry scan. B) Single image of a channel with various amounts of space between the walls and the support columns. C) The three channels shown illustrate the effect of nitride thickness on probability of collapse. See Section 6.2 for details.

FIGS. 20A-D. Variations of the micro (µ) DFAS mark pattern available for use with the Autostep mask aligner. A) Snapshot of CAD image for "solid rectangle." micro DFAS mark in positive tone. B) Snapshot of CAD image for "segmented line" microDFAS mark in positive tone. C) Snapshot of CAD image for "solid rectangle" micro DFAS mark in negative tone. D) Bright field image of a micro DFAS mark etched into a fused silica wafer. See Section 6.2 for details.

FIGS. 21A-D. A) dark field image of µDFAS mark pattern 1 etched into fused silica. B) dark field image of µDFAS mark pattern 1 under SPR 955 0.9 photresist. C) dark field image of µDFAS mark pattern 2 etched into fused silica. D) dark field image of µDFAS mark pattern 2 under SPR 955 0.9 photoresist. See Section 6.2 for details.

FIGS. 22A-I. Photoresist and Lift-off Resist (LOR) profiles for two different thicknesses of LOR. The left column shows the profile of 100 nm thick LOR during various stages. A) a fused silica wafer is prepared with 100 nm LOR and 900 nm photoresist. B) After exposure, the wafer is placed into 300 MIF developer. Initially the exposed pattern in photoresist dissolves. C) Over the course of the development process, LOR is isotropically etched at a much slower rate than the exposed photoresist, but at a faster rate that the unexposed photoresist. D) A thin layer of metal is deposited by e-beam evaporation. E) fused silica wafer is prepared with 500 nm LOR and 900 nm photoresist. F-I) photoresist is developed and LOR is isotropically etched. See Section 6.2 for details.

Figure 23:
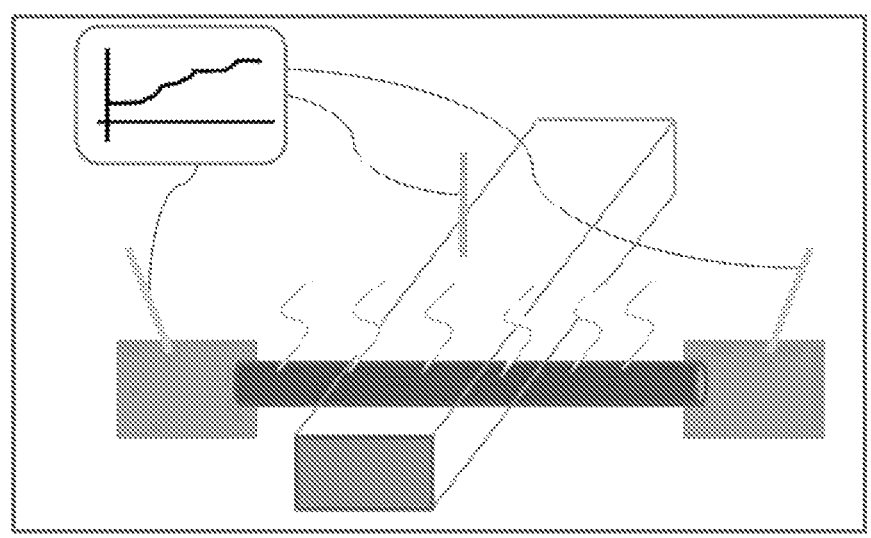

FIG. 23. Schematic representation of an electrical detector comprising a nanowire. See Section 6.4 for details.

Figure 24:
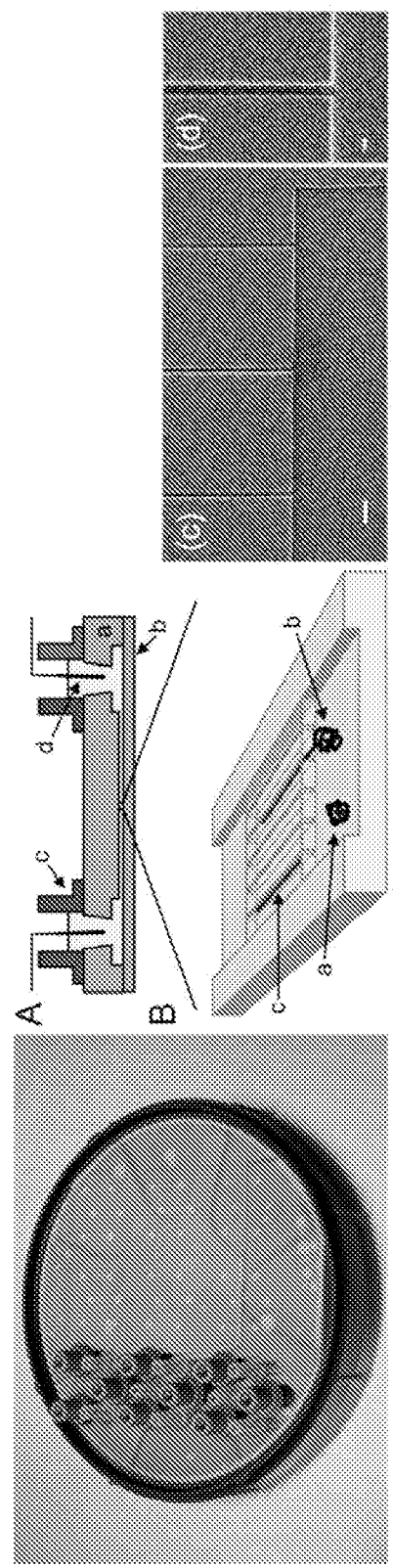

FIG. 24. (Left) Photograph of a 100 millimeter diameter fused silica wafer containing 27 devices, each consisting of a parallel array of 16 fluidic channels for single molecule analysis. (Middle) Schematic of an electrical detector with a nanochannel array. (Right) Top down scanning electron micrograph of nanochannel array (c) and magnified image of a single nanochannel (d). See Section 6.4 for details.

Figure 25:
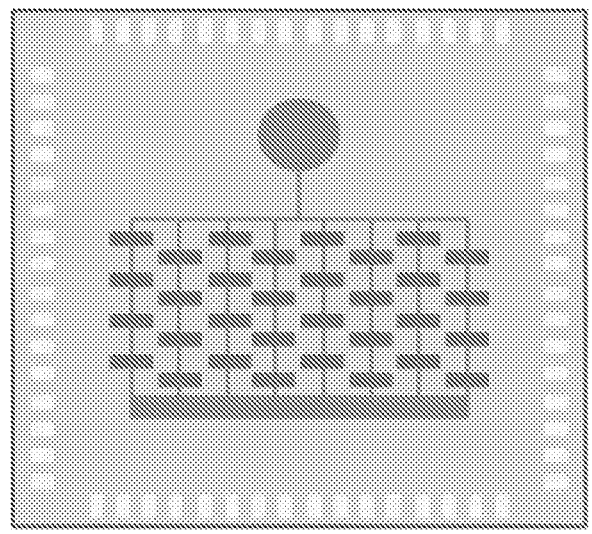

FIG. 25. Schematic representation of an embodiment of the microfluidic network on an electrical detector. See Section 6.4 for details.

Figure 26:
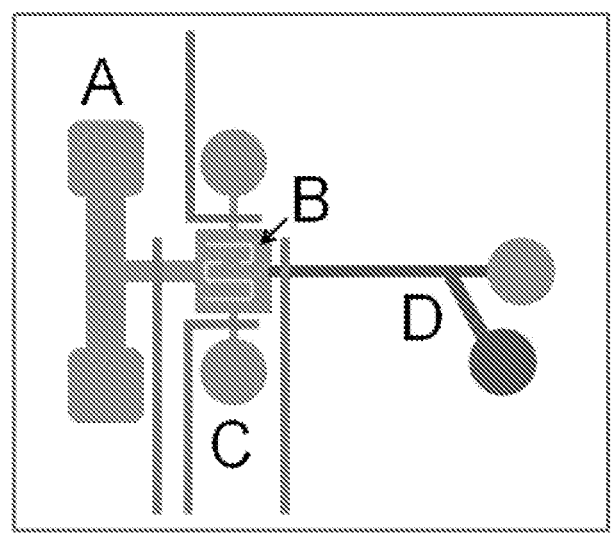

FIG. 26. Schematic illustration of PDMS microfluidic channels for cell manipulation, lysing, reverse transcription, and capillary electrophoresis of cDNA. See Section 6.4 for details.

Figure 27:
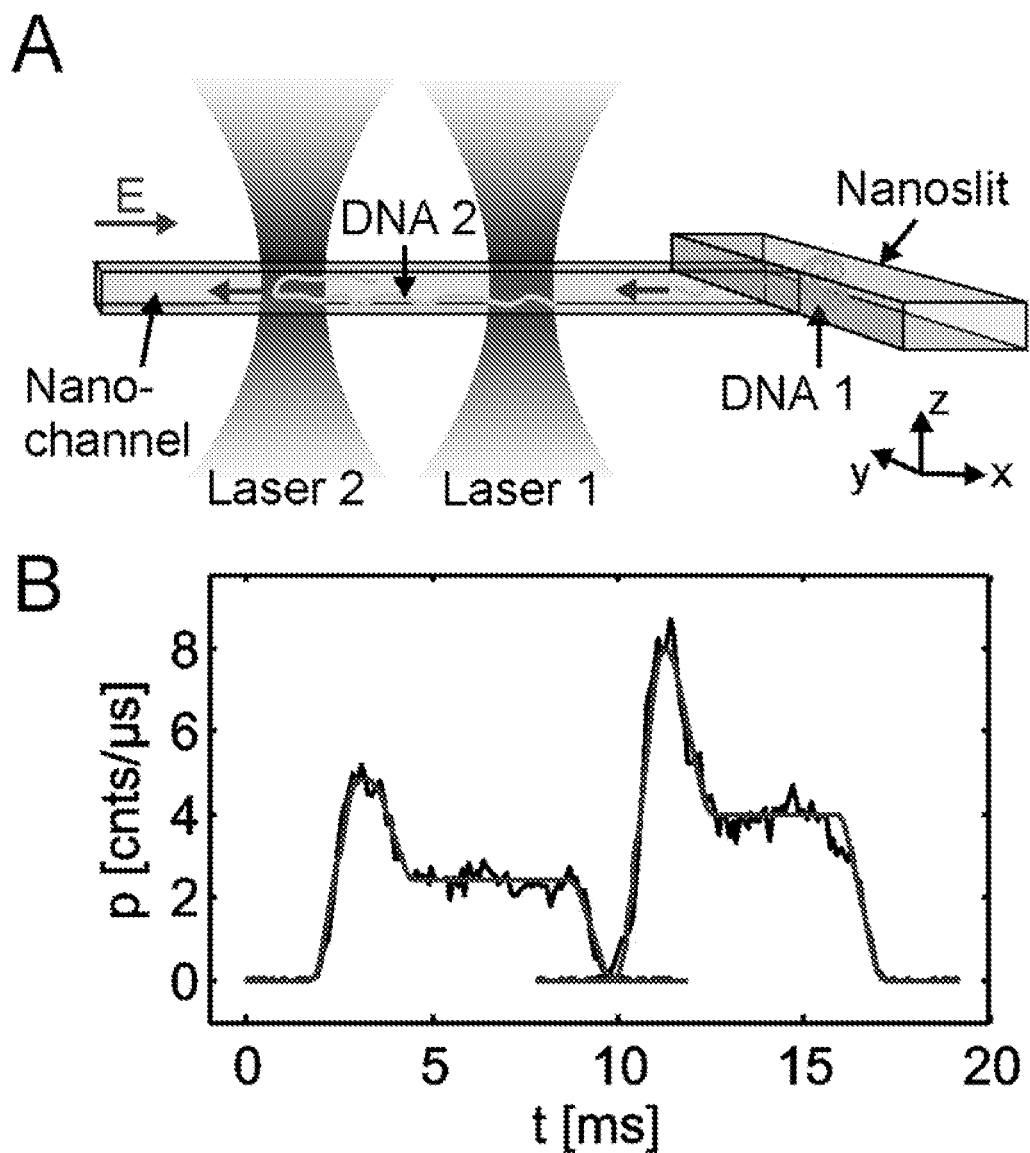

FIGS. 27A-B. Experimental Schematic. (A) Fluorescently labeled DNA molecules are dynamically elongated by driving them electrophoretically from a nanoslit into a nanofluidic channel (DNA 1). The nanochannel is probed by two sequentially focused lasers. DNA molecules driven through the resulting focal volumes generate two similar fluorescent signals which are shifted in time relative to each other (DNA 2). These signals can be used to determine single molecule statistics for the sample such as speed, length, folding conformation and fluorescence intensity, and are used in the presented work to illuminate several aspects of the physics of DNA translocation through nanofluidic channels. (B) Two photon count signals p resulting from the two focal volumes and fits versus time t with a 100 µs bin time at a device bias of 50V. The fits result in an apparent DNA length $l_A$=9.10±0.05 µm, speed $v_S$=1315±3 µm/s and ratio of folded length to apparent length $l_L/l_A$=22.3±0.4%. See Section 6.5 for details.

FIGS. 28A-D. Optical Setup and Devices. (A) Two lasers are directed into the back of a microscope objective and focused at different positions along the length of a single nanochannel. The two fluorescent signals are collected, split and focused on optical fibers coupled to Avalanche Photo Diodes (APDs). (B) An optical micrograph of the chromium etch mask shows the structure of the nanochannel device. The white arrows mark the entrances to one of the eight nanochannels in the array. The mask consists of a coarse layer for the nanoslit made with optical lithography, and a fine layer for the nanochannels made with electron beam lithography. The electron beam layer was designed to reduce write times and proximity exposure effects. (C) An electron micrograph shows the interface between the nanoslit and a nanochannel. The etch depth is 100 nm and the nanochannels are 90 nm wide. (D) An electron micrograph shows the entrance to a nanochannel. The device floor roughness of 10-20 nm is attributed to the etching process. See Section 6.5 for details.

Figure 29:
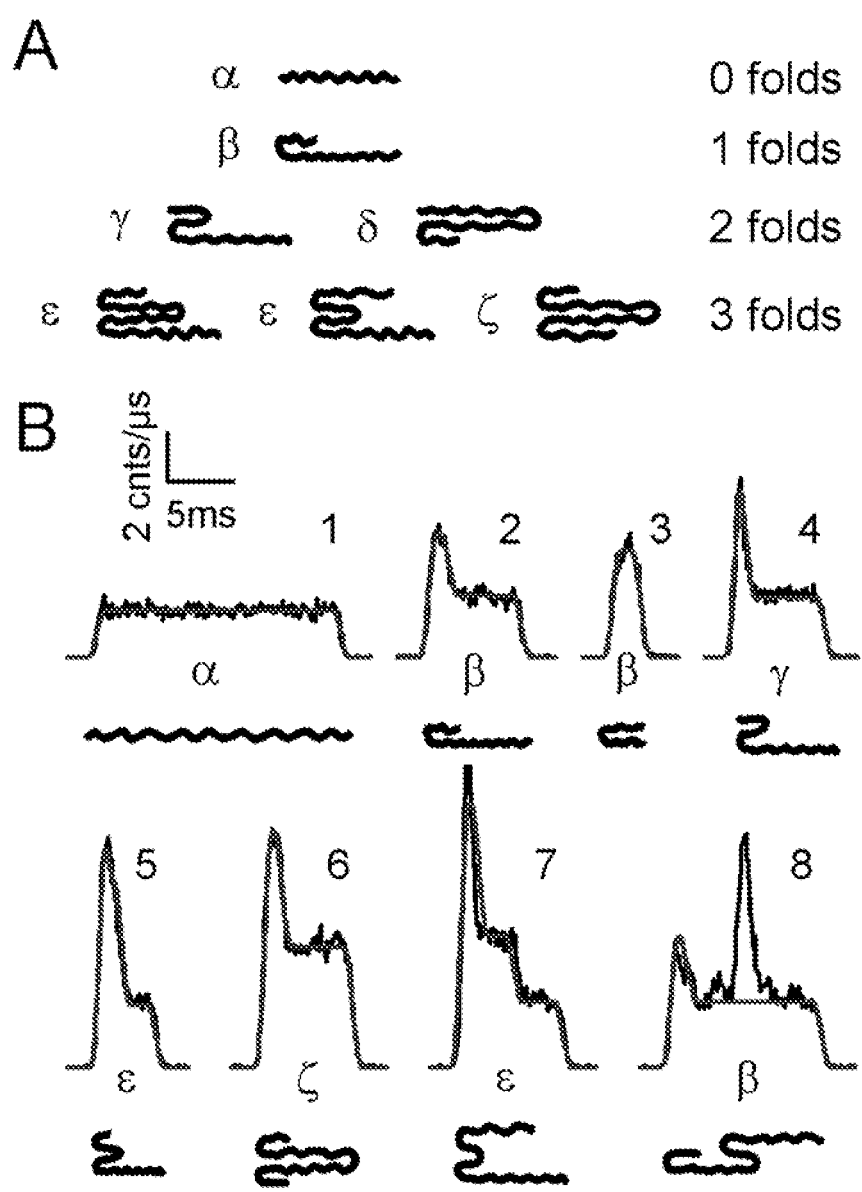

FIGS. 29A-B. Single Molecule Analysis. (A) Seven theoretical molecular conformations with up to three folds were used to describe electrodynamically stretched DNA molecules in a nanochannel. Six analytical models, denominated a–ζ, were developed from these conformations to fit bursts of fluorescence, with model ε covering two shapes. (B)

Observed bursts of fluorescence and fits from the first focal volume (signal 1) are shown. Fluorescence bursts are interpreted with the folding model and conformation drawn underneath (fits shown in red). Burst 8 shows a rare fold, knot or overlapping fragment in the middle of the molecule and is fitted using model β. The most frequently observed burst shapes were shapes 2, 4 and 5, while the others were rare. See Section 6.5 for details.

FIGS. 30A-F. λ-bacteriophage DNA. 416 molecules from a λ-bacteriophage DNA sample are analyzed in a one minute run. The average molecule speed is $\bar{v}_S$=1.33±0.07 mm/s at a device bias of U=50V. (A) Distribution of the apparent length $l_A$. (B) Distribution of the real length $l_R$. (C) Schematic defining apparent length $l_A$, real length $l_R$, free length $l_F$ and folded (looped) length $l_L$ for a molecule with a single loop. (D) Photon counts (cnts) per molecule versus apparent length $l_A$. (E) Photon counts per molecule versus real length $l_R$. The linear fit passing through the origin has a slope of 4,430±20 cnts/μm. (F) Distribution of the photon counts per molecule. A comparison of (D) and (E) shows that folding explains the distribution of molecules with the same photon count over different apparent length. Fitting the photon counts (F) and the real length distribution (C) with Gaussians leads to a mean photon count of 48,000±2,000 photons and a real length of 10.7±0.3 μm for intact λ-DNA molecules. All molecules within two standard deviations of the mean photon counts and the mean real length are considered to be intact (horizontal and vertical arrows indicate region). This accounts for 52% of the molecules analyzed, while the rest of the molecules are interpreted as fragments or concatemers. (E Inset) Distribution of the ratio of free length to real length $l_F/l_R$ for all intact molecules. 79% of the intact molecules have $l_F/l_R$>0.5. See Section 6.5 for details.

Figure 30:
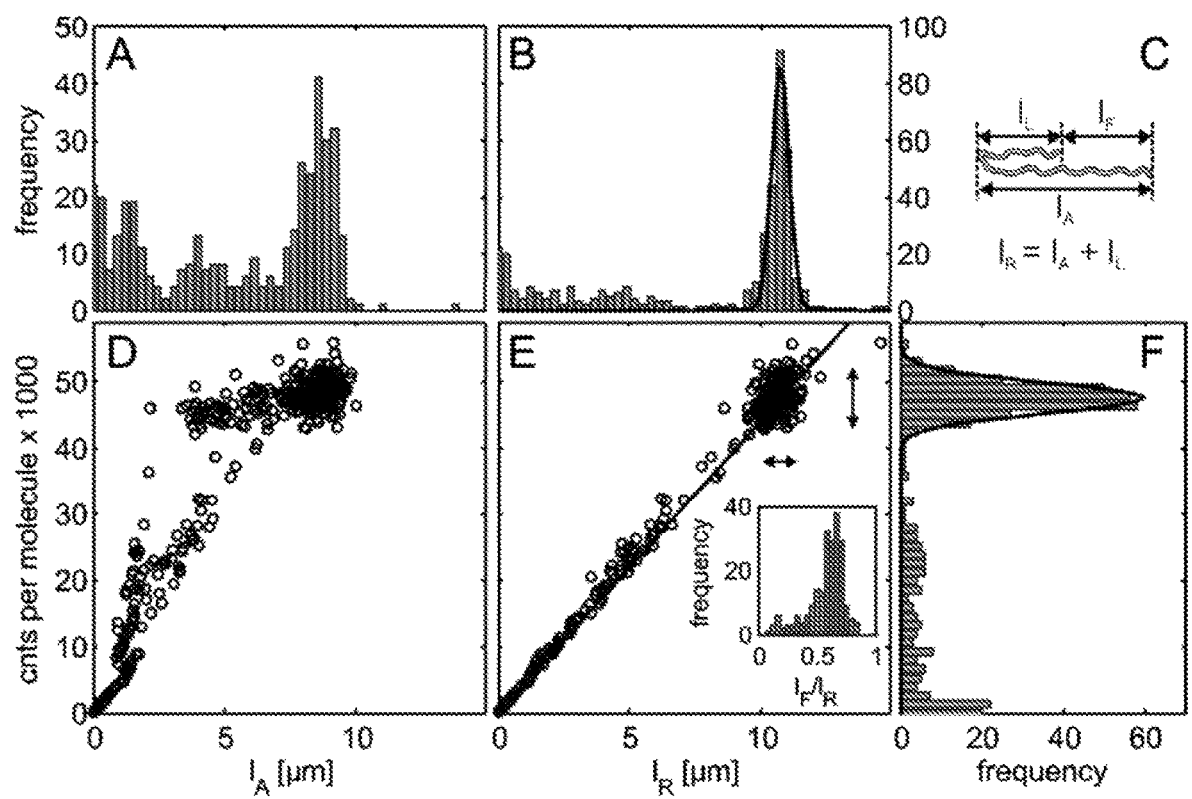
Figure 31:
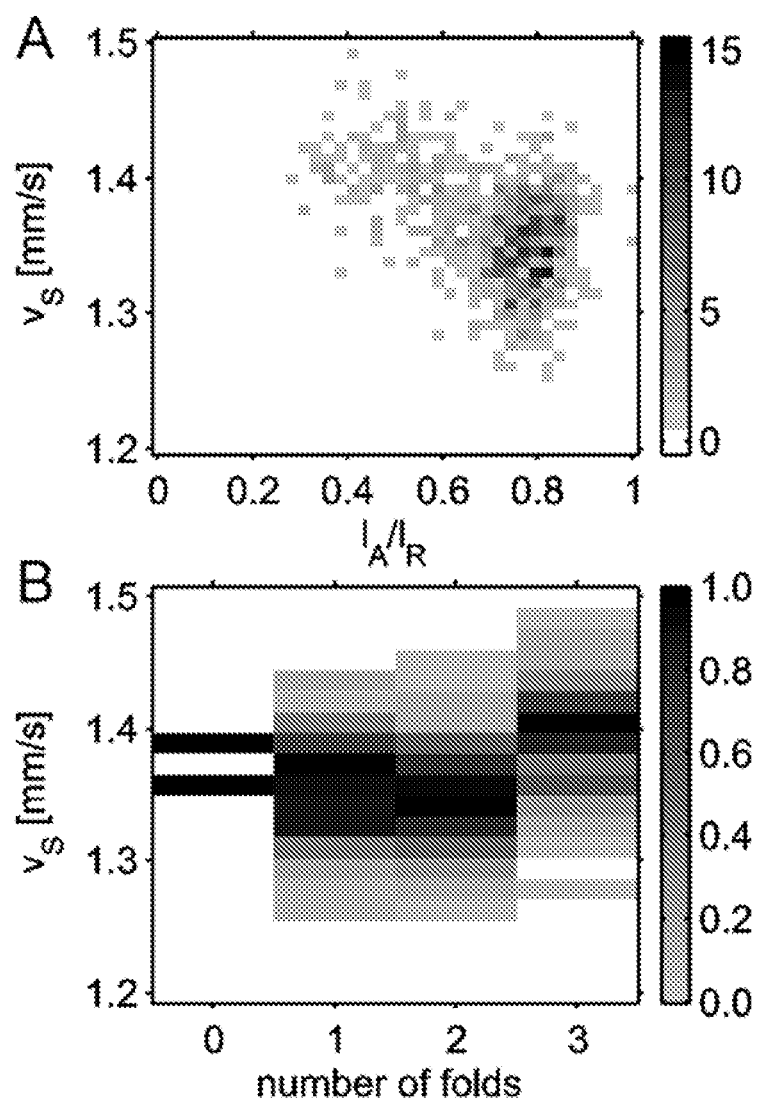

FIGS. 31A-B. Speed and Folding. (A) Distribution of speed $v_S$ versus ratio of apparent length to real length $l_A/l_R$ for 752 λ-bacteriophage DNA molecules. Intact λ-bacteriophage molecules from three subsequent one minute runs (including the experiment in FIGS. 30A-F at a device bias of U=50V are presented. DNA molecules with increased folding and smaller $l_A/l_R$ have a slightly higher speed $v_S$. (B) Normalized distribution of speed $v_S$ versus number of folds for the same molecules shown above. The number of folds is determined by the analytical model (see FIG. 29B) chosen to analyze each molecule and is a measure of the number of parallel strands in the channel. DNA molecules with three folds in the molecule confirmation have slightly higher speed $v_S$. See Section 6.5 for details.

Figure 32:
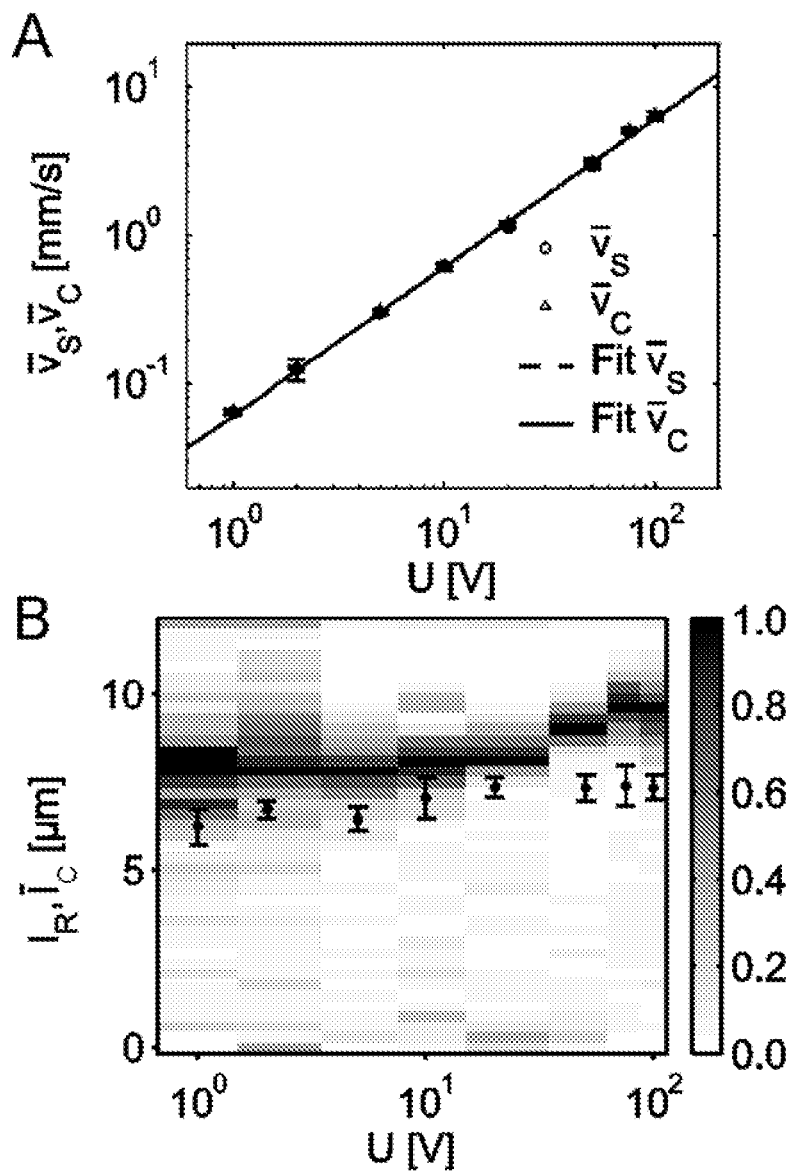

FIGS. 32A-B. Speed, Length and Device Bias. The dependence of DNA speed and length on device bias for a λ-bacteriophage sample is shown. Five continuous runs were performed for each bias, and the cross-correlation functions as well as the single molecule photon bursts are analyzed. (A) Average single molecule speed $\bar{v}_S$ and average cross-correlation speed $\bar{v}_c$ versus device bias U. Linear fitting of $\bar{v}_S(U)$ yields a slope of $m_S$=60.9±1.4 μm/(Vs), while a linear fit of $\bar{v}_c(U)$ gives a slope of $m_c$=61.0±0.7 μm/(Vs). The plots overlap with each other. (B) Normalized distribution of real length $l_R$ versus device bias U. The maximum of the length distribution shows up in black and corresponds to the majority of intact DNA molecules, which increase in real length $l_R$ as the device bias increases. This behavior is not as evident for the average length $\bar{l}_C$ (black dots) resulting from cross-correlation curves, probably because this analysis neglects folding and fragmentation. The number of molecules n for the different device biases U was 263 at 1V, 381 at 2V, 226 at 5V, 144 at 10V, 270 at 20V, 417 at 50V, 1217 at 75V and 868 at 100V. See Section 6.5 for details.

FIGS. 33A-F. Length, Velocity and Size. Analysis of a sample containing a mixture of λ-bacteriophage DNA and its HindIII digest. 15,144 molecules were detected in two minutes with an average speed $\bar{v}_S$=3.6±0.2 mm/s. (A) Distribution of the real length $l_R$. The peaks are shown fitted to nine modified Gaussians (red). (B) Real length $l_R$ versus number of base pairs. (C) Photon count cnts per molecule versus the number of base pairs. (D) Distribution of photon counts cnts per molecule versus real length $l_R$. (E) Distribution of the photon counts per molecule. (F) Color coded intensity histogram (here shown in gray scale) of the number of molecules against the molecule speed $v_S$ and the real length $l_R$. See Section 6.5 for details.

Figure 34:
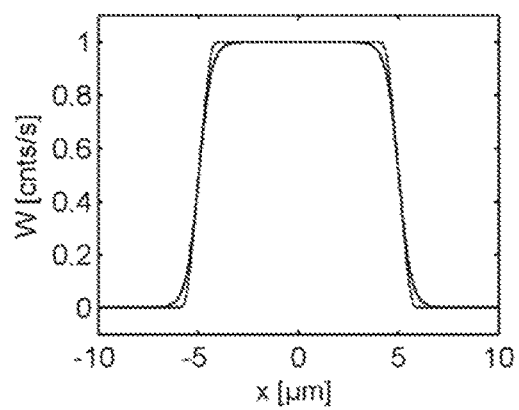

FIG. 34. Comparison between the calculated Molecular Detection Efficiency (MDE) function p(x) (gray) from Eq. 7 and its modified sigmoidal replacement W(x) (black) from Eq. S-2. Both curves are calculated assuming a fiber diameter of 50 um, an objective magnification of 40×, and Gaussian radius of the Airy disk of o=140 nm and a normalized amplitude $p_0$=1 cnts/s. Although W(x) does not reproduce the curved parts of p(x), it matches the side slopes and the plateau. See Section 6.5 for details.

5. DETAILED DESCRIPTION OF THE INVENTION

An electrical detector is provided comprising a nanofluidic channel and a charge sensor integrated in the nanofluidic channel, wherein the charge sensor is a nanowire, nanotube, transistor or capacitor. Methods for detecting charged species, such as biological or chemical species, in the nanofluidic channel with the charge sensor are also provided. Methods are also provided for optically detecting charged, labeled or tagged species in the nanofluidic channel. Methods for fabricating the electrical detector are also provided. In one embodiment, the fabrication methods comprise a combination of nano/micro-fabrication processes. In another embodiment, the electrical detector is a "lab on chip" device that can be used to isolate, confine and otherwise manipulate species, e.g., molecules or particles, of interest.

The integration of nanoscale charge sensors into nanofluidic channels ("nanochannels") as disclosed hereinbelow represents a significant step forward in terms of device performance. It can also lead to more compact, portable and cheaper products.

For clarity of disclosure, and not by way of limitation, the detailed description of the invention is divided into the subsections set forth below.

5.1 Electrical Detector

An electrical detector is provided comprising a nanofluidic channel and a charge sensor, wherein:

the charge sensor is selected from the group consisting of nanowire, nanotube, transistor and capacitor, and a portion of the charge sensor is integrated in the nanofluidic channel, whereby the charge sensor is contacted by fluid in the nanofluidic channel.

In one embodiment, the portion of the charge sensor is disposed within, or on the surface of, the nanofluidic channel.

In another embodiment, the entire charge sensor is disposed within, or on the surface of, the channel.

In another embodiment, the electrical detector comprises charge sensor electrodes disposed within, or on the surface of, the channel.

In another embodiment, the electrical detector comprises a plurality of nanofluidic channels.

In another embodiment, the plurality of nanofluidic channels is 2-10, 10-50, 50-100, 100-500, 500-1000, or 1000-5000 channels.

In another embodiment, a portion of each of the plurality of charge sensors is integrated in the nanofluidic channel.

In another embodiment, the plurality of charge sensors is 2-10, 10-50, 50-100, or 100-500 sensors.

In another embodiment, the nanofluidic channel depth is on the order of the Debye screening length.

In another embodiment, the nanofluidic channel depth is smaller than the Debye screening length.

In another embodiment, the nanofluidic channel depth is 2-10 times the Debye screening length.

In another embodiment, the nanofluidic channel depth is 0.1 nm to 1 mm.

In another embodiment, the Debye screening length is 0.1 nm to 1000 nm.

In another embodiment, the Debye screening length is 10 nm.

In another embodiment, the width of the nanofluidic channel is 0.1 nm-1 nm, 1 nm-5 nm, 5 nm-10 nm, 10 nm-50 nm, 50 nm-100 nm, 100 nm-500 nm, 500 nm-1 µm, 1 µm-5 µm or 5 µm-10 µm.

The electrical detector with nanofluidic channel and nanoscale charge sensor can be used to isolate, confine or otherwise manipulate species of interest, such as molecules or particles, thereby enabling the species to be detected, measured, characterized, or otherwise assessed.

In one embodiment, the charge sensor (e.g., nanotube or nanowire) comprises a semiconducting material.

The charge sensor can comprise carbon, silicon, carbon and silicon or any other type of FET known in the art.

In another embodiment, the transistor is a field effect transistor (FET).

In another embodiment, the FET is a film disposed on a surface of the nanofluidic channel.

In a specific embodiment, the nanotube is a p-type or n-type nanotube.

FIG. 1 shows one embodiment of a nanofluidic channel with an integrated charge sensor. FIG. 1 (left side) is a top down view showing source and drain electrodes as grey squares. Thin horizontal lines indicate channel side walls. The dark black line indicates a carbon nanotube, although any nanotube or nanowire (e.g., carbon, silicon, carbon and silicon) connecting the source and drain electrodes in this manner is suitable. The squiggled line depicts a DNA molecule that is moving along the nanofluidic channel in the direction of the channel axis, and will soon be on top of the nanotube. Any charged molecule (for example, nucleic acids (e.g., DNA, RNA, miRNA), proteins, virus particles, cells, cellular components, cell fragments) can be sensed with this electrical detector.

FIG. 1 (right side, top) is a side view of a nanofluidic channel with integrated nanowire. In this particular embodiment, the nanowire is disposed on the floor of the channel. In other embodiments, it may be attached to the ceiling or may even be suspended in the middle of the channel (in the z-plane). Charged ions floating in the solution are shown as positive or negative signs.

FIG. 1 (right side, bottom) shows that for sensing purposes, one parameter to be considered is the relation between the total depth of the nanochannel and the ionic screening length, i.e., the distance over which charged molecules are screened by other ions in solution. In a specific embodiment, the relation between the total depth of the nanochannel and the ionic screening length is roughly equivalent or the same order of magnitude. In one embodiment, the nanofluidic channel is filled with fluid and the target molecules are caused to flow through the channel. If the channel depth is made roughly equal to or less than the ionic screening length, all target molecules that flow through the channel will pass close enough to the nanowire sensor so as to affect its conductivity, and therefore, to be detected.

This is less preferred in some circumstances where picking one chemical species from many in solution is in that all charged molecules close to the nanotube, regardless of their chemical structure can trigger a detection event. However, this is preferred in other situations. One such advantageous situation is in the detection of single DNA molecules. In one embodiment, a single DNA molecule is detected, as described below in Section 6.1.

The electrical detector comprising a nanofluidic channel and a charge sensor integrated in the nanofluidic channel can be used, in certain embodiments, as a "lab-on-a-chip" device.

In one embodiment, the electrical detector has a charge sensor element that is enclosed inside of, or integrated into, a nanoscale fluidic ("nanofluidic") channel as depicted in FIG. 1. The electrical detector can be used by filling the nanochannels with solution and monitoring the electrical current that conducts through the charge sensor (e.g., nanowire or nanotube) as adjustments are made to the solution potential or as molecules of interest pass near the charge sensor.

Any molecular species of interest can be detected by the electrical detector. In one embodiment, the solution contains a biological or a chemical species of interest to be detected.

In another embodiment, the electrical detector comprises a microfluidic or macrofluidic structure fluidically connected to the nanofluidic channel.

In another embodiment, the microfluidic or macrofluidic structure is a reservoir or channel.

In another embodiment, the microfluidic or macrofluidic structure is selected from the group consisting of a cell sorting area, a filtering area, a separating area, a nucleic acid amplification area, a reaction area and a storage area.

In another embodiment, the molecule of interest contacts the charge sensor.

In another embodiment, the molecule of interest does not contact the charge sensor.

In another embodiment, the molecule of interest is in close proximity to the charge sensor.

In another embodiment, the molecule of interest is label-free or unlabeled.

In another embodiment, the charge sensor is an addressable semiconducting charge sensor that behaves as an electrolyte gated field effect transistor.

In another embodiment, the charge sensor is nonfunctionalized.

In another embodiment, the charge sensor is functionalized.

In another embodiment, the charge sensor is functionalized with a molecule selected from the group consisting of an antibody (or portion thereof) and an oligonucleotide.

In another embodiment, the electrical detector comprises a substrate.

In another embodiment, the substrate is a semiconducting or insulated substrate.

In another embodiment, the substrate is germanium or comprises germanium.

In another embodiment, the substrate is silicon, silicon-based, or comprises silicon (or a derivative thereof).

In another embodiment, the silicon-based substrate is selected from the group consisting of silicon, silica (silicon dioxide) and glass (e.g., borosilicate glass).

In another embodiment, the silica substrate is fused.

In another embodiment, the substrate is electrically insulated or comprises at least one electrically insulated surface.

In another embodiment, the substrate is transparent.

In another embodiment, the transparent substrate has a thickness compatible for use with a desired microscope objective for optical observation of a molecule of interest in the nanofluidic channel.

In another embodiment, the transparent substrate has a thickness of about 170 nm.

In another embodiment, optical observation of a molecule of interest in the nanofluidic channel is conducted in addition to electrical detection.

In another embodiment, the electrical detector comprises a constant source-drain bias voltage applicator (e.g., voltage source and ammeter) wherein change in the charge sensor conductance is observed by applying a constant source-drain bias voltage with the applicator and monitoring the current through the charge sensor.

In another embodiment, the bias voltage is selected from the group consisting of AC bias, periodic signal and non-periodic signal.

In another embodiment, the electrical detector comprises a source and drain electrode pair electrically connected to the charge sensor by electrical contacts.

In another embodiment, the electrical detector comprises an insulator insulating the electrical contacts of the source and drain electrode pair to the charge sensor.

In another embodiment, the electrical contacts are platinum.

In another embodiment, the insulator is silicon nitride.

In another embodiment, dimensions of the nanofluidic channel constrain or confine a molecule or particle of interest to within a sensing range of the charge sensor.

In another embodiment, the charge sensor is disposed in the channel in sufficiently close proximity to the constrained or confined molecule or particle of interest so as to avoid significant charge screening.

In another embodiment, the sensing range is the diameter of the charge sensor plus twice the ionic screening length.

In another embodiment, the molecule or particle of interest is a charged molecule or particle.

In another embodiment, the molecule or particle of interest is unassociated or free.

In another embodiment, the molecule or particle of interest is bound to another entity.

In another embodiment, the molecule or particle is labeled or unlabeled (label-free).

In another embodiment, the molecule or particle of interest is a biological species, e.g., a virus, nucleic acid (e.g., DNA, RNA, miRNA), protein, cell, cell fragment or organelle, a chemical species, or a fibrous particle, metal particle, or quantum dot.

In another embodiment, the molecule or particle of interest is detected, controlled or manipulated.

5.2 Methods for Fabricating the Electrical Detector

Methods are provided for manufacturing the electrical detector comprising employing standard photolithographic and MEMs processing techniques and carbon nanotube growth processes known in the art.

The electrical detector can be constructed using a combination of nano/micro-fabrication processes. Those include but are not limited to photolithography, reactive ion etching, wet chemical etching, chemical vapor thin film deposition, evaporative thin film deposition, chemical vapor growth of nanowires.

In one embodiment, the electrical detector is manufactured by a combination of microfabrication processes known in the art. An overview of the process, with three specific embodiments, is set forth below. The Examples in Sections 6.2-6.4 set forth additional embodiments of methods for fabricating the electrical detector.

The initial substrate may be a blank fused silica wafer, a blank silicon wafer, or some other flat, suitable substrate known in the art that can survive all of the processing steps. For example, an electrically insulating substrate or a substrate that has a non-conducting surface can be used. The following layers are created on the substrate to create the nanochannel-nanowire device:

Alignment Mark Layer
Metal Contact Pad Layer
Nanowire Catalyst Layer
Sacrificial Material Layer
One (or more) Dielectric Layers
Various Access Hole (or Via) Layers In this notation a "Layer" is defined to mean that one or more of the following actions has been performed: lithography based patterning, wet or dry etching, metal deposition through evaporation, and or chemical vapor deposition.

In one embodiment ("Fabrication process Version 1"), the fabrication process is as follows:

Photolithographically define alignment marks on wafer and transfer marks to wafer using a wet or dry etch.

Photolithographically define pattern for source and drain metal electrodes on wafer and deposit metal.

Photolithographically define pattern for catalyst particle pads and deposit catalyst particles.

Grow nanowires on chips using chemical vapor growth process

Photolithographically define pattern for nanochannel sacrificial material and deposit sacrificial material.

Deposit thin film dielectric material (which will become the ceiling of the channel).

Photolithographically define etch holes on wafer and transfer marks to etch holes into thin film dielectric using wet or dry etching.

Remove sacrificial material using a wet or dry etch.

Enclose etch holes using a thin film dielectric deposition process.

In another embodiment ("Fabrication process Version 2"), the fabrication process is as follows:

Photolithographically define alignment marks on wafer and transfer marks to wafer using a wet or dry etch.

Photolithographically define pattern for source and drain metal electrodes on wafer and deposit metal.

Photolithographically define pattern for catalyst particle pads and deposit catalyst particles.

Grow nanowires on chips using chemical vapor growth process

Deposit a protective ultrathin layer of dielectric on chip. This reduces the probability that nanowires suffer an electrical short during the remaining fabrication steps.

Photolithographically define pattern for nanochannel sacrificial material and deposit sacrificial material.

Deposit thin film dielectric material (which will become the ceiling of the channel).

Photolithographically define etch holes on wafer and transfer marks to etch holes into thin film dielectric using wet or dry etching.

Remove sacrificial material using a wet or dry etch.

Etch ultra thin film protective dielectric using a wet or dry etch, thereby exposing the nanowires to the channel.

Enclose etch holes using a thin film dielectric deposition process.

In yet another embodiment ("Fabrication process Version 3"), the fabrication process is as follows:

Photolithographically define alignment marks on wafer and transfer marks to wafer using a wet or dry etch.

Photolithographically define pattern for nanochannel sacrificial material and deposit sacrificial material.

Deposit a protective ultrathin layer of dielectric on chip. This reduces the probability that the sacrificial material reacts with process gases during any subsequent high temperature step (such as nanowires growth).

Photolithographically define pattern for source and drain metal electrodes on wafer and deposit metal.

Photolithographically define pattern for catalyst particle pads and deposit catalyst particles.

Grow nanowires on chips using chemical vapor growth process

Deposit thin film dielectric material (which will become the ceiling of the channel).

Photolithographically define etch holes on wafer and transfer marks to etch holes-into thin film dielectric using wet or dry etching.

Remove sacrificial material using a wet or dry etch.

Etch ultra thin film protective dielectric using a wet or dry etch, thereby exposing the nanowires to the channel.

Enclose etch holes using a thin film dielectric deposition process.

FIG. 2 depicts an overview of the method for fabricating the electrical detector, by which charge sensors such as nanowires can be integrated into a nanofluidic channel. FIG. 2 shows sacrificial layer processes for nanowire integration. The left side of FIG. 2 shows an overview of the process by which nanowires can be integrated into a nanofluidic channel. The right side illustrates a double sacrificial layer process in which the nanowires are protected during fabrication by a thin film of silicon nitride. The double sacrificial layer will only needed in some cases, as can be determined readily by the ordinarily skilled artisan.

In certain embodiments, the electrical detector can exhibit spatial resolution 2 to 3 orders of magnitude better than the optical diffraction limit. Whereas for optical detection methods known in the art, the "optical probe" is defined as the illuminated region of solution, in the case of nanochannel-nanowire, the resolution is determined by the diameter of the electrical probe. This diameter is defined as the diameter of the nanowire plus twice the ionic screening length. Using commonly grown nanowires or nanotubes and solutions of reasonably high ionic strength, an electrical probe of roughly 1 nm can be readily obtained using the methods disclosed herein and known in the art.

Owing to the highly advanced state of microelectronics technology, all of the elements needed to control the electrical detector, transduce and amplify signals, and even analyze signals can be readily miniaturized because the detection method is purely electrical, in contrast to the case in which there is first an optical transduction that is then followed by an electrical transduction (as is the case for standard fluorescence microscopy). In addition to the possibility of making a truly portable lab on a chip device, the electrical detector can be manufactured at a far lower cost by employing the economies of scale inherent in microfabrication methodology.

5.3 Methods for Using the Electrical Detector

The electrical detector can be used to detect molecules or species of interest, such as charged molecules and biological or chemical species. In one embodiment, a method is provided for detecting a biological or chemical species of interest or a tag associated with the species comprising:

providing the electrical detector;

flowing an entity comprising the species or the tag associated with the species through the nanofluidic channel (e.g., a molecule of interest in solution); and contacting the charge sensor with the species or the tag, thereby producing a detectable signal indicative of the presence of the biological or chemical species of interest.

According to this method, the electrical detector can be used as an analytic tool in the fields of biological analytics and chemical analytics. It also has utility as a research tool in the area of nanofluidic science. The electrical detector can be used to analyze virtually any charged molecule or species, e.g., biological or chemical species including, but not limited to: virus, nucleic acid (e.g., DNA, RNA, miRNA), protein, cell, cell fragment, cell organelle, fibrous particle, metal particle, or quantum dot.

A method is also provided for detecting a local solution potential of interest comprising:

providing the electrical detector;

flowing the solution through the nanofluidic channel; and contacting the charge sensor with the solution, thereby producing a detectable local solution potential signal.

According to this method, the electrical detector can be used to accurately measure the local solution potential inside a nanofluidic channel. The electrical detector can have utility as a single molecule (e.g., DNA) detector. Such a utility has application for obtaining DNA fragment length information. Such information is sought and can be provided by using the electrical detector while performing a wide variety of commercially relevant biological tests.

The electrical detector has utility in a wide variety of biological and chemical tests (e.g., clinical diagnostics, drug development, pathogen detection, basic life science research. The electrical detector can be used, as disclosed above, for nucleic acid (or nucleic acid fragment) length measurement. Indeed many tests involving detection of charged macromolecules in solution can benefit from direct electrical sensing in a confined environment using the electrical detector. The electrical detector can also be used as a general sensing element in nanofluidic devices for determination of a local solution potential in a microchannel or nanochannel, e.g., for the study of ion distributions and fluid movement in such channels.

A method is also provided for measuring conformation, length, speed or optically detectable feature, label or tag intensity of a molecule or particle of interest comprising:

providing:

a molecule or particle of interest (e.g., a charged molecule or particle) with an optically detectable feature, label, or tag, a nanoslit, a nanofluidic channel, and two spatially separated focal volumes defined by lasers focused sequentially on the nanochannel;

driving electrophoretically the charged molecule or particle from the nanoslit into the nanofluidic channel, thereby confining and dynamically elongating the charged molecule or particle beyond its equilibrium length in the nanochannel;

transporting the elongated charged molecule or particle through the two spatially separated focal volumes, thereby generating a first optically detectable signal and a second optically detectable signal shifted in time relative to each other;

detecting photon bursts (or photon count signals) from the first and second optically detectable signals;

measuring the photon bursts (or photon count signals) from the first and second optically detectable signals;

performing a speed or a cross correlation measurement using the measurement from the photon bursts (or photon count signals) from the first and second optically detectable signals; and calculating the conformation, length, speed or label intensity of the molecule or particle of interest from the speed or cross correlation measurement.

In certain embodiments, the charged molecule or particle of interest is a nucleic acid such as DNA or RNA, or a derivative or fragment thereof. In a specific embodiment, the nucleic acid (or fragment thereof) is fluorescently labeled.

In a specific embodiment, the molecule of interest (or tag associated with the molecule of interest) is associated with a disease or disorder (e.g., cancer) and the method is used for screening for the disease or disorder.

In other embodiments, the nucleic acid can be hybridized to a nucleic acid probe, covalently linked to a probe or tag, or can be locally modified by other mechanisms known in the art (e.g., base methylation). Such modifications may alter the charge of the nucleic acid, and hence be detectable by the electrical detector, without the need for a linked probe or tag.

Section 6.5 (Example 5) discloses several preferred embodiment of the method.

In another embodiment, the method comprising providing the electrical detector, wherein the electrical detector comprises (and provides) the nanoslit and the nanofluidic channel. According to this embodiment, both optical detection and electrical (charge) detection can be conducted in the electrical detector if desired.

In another embodiment, the optically detectable label is a fluorescent label.

In another embodiment, the method comprises:

providing a first optical fiber connected to a first photodiode and a second optical fiber connected to a second photodiode;

projecting an image from the first optically detectable signal on the first optical fiber;

projecting an image from the second optically detectable signal on the second optical fiber;

detecting the image from the first optically detectable signal with the first photodiode;

detecting the image from the second optically detectable signal with the second photodiode;

determining a number of emitted photons per channel length and time along the nanofluidic channel axis;

determining a resulting image at each optical fiber position;

measuring each optically detectable signal by determining a number of photons arriving at each photodiode.

In another embodiment, the method comprises analyzing the cross correlation function of the two measured optically detectable signal signals. In another embodiment, the method comprises performing single-molecule burst analysis. In yet another embodiment, calculating the conformation, length, speed or label intensity of the charged molecule or particle of interest comprises performing Gaussian fitting of logarithmic distributions. Exemplary methods for such analyses and calculations are set forth in Example 6.5.

5.4 Methods for Detecting DNA and Other Nucleic Acids

A DNA molecule is a linear polymer that is very flexible and that can be stretched by many methods well known in the art, including confinement induced elongation in nanochannels. Furthermore, the charge along a DNA molecule's backbone is roughly homogenous, so that if an elongated DNA strand, confined to a nanochannel, is run by a charge sensitive detector, the resulting output of the detector is a pulse train of roughly constant height, with a duration that depends on the length and velocity of the DNA strand.

If the velocity of a DNA through-molecule is known or can be measured, then its length can be determined based on the duration of time of the pulse train. When used in this mode, the electrical detector comprising a nanofluidic channel and a charge sensor can provide rapid measurements of DNA fragment lengths for a number of different biological assays (e.g., post-restriction digestion analysis, miRNA analysis, cancer screening).

In a specific embodiment, the electrical detector is employed in label-free electronic profiling of microRNA expression in a single cell.

In yet another embodiment, all nucleic acid processing steps commonly known in the art (e.g., amplification, filtration or optionally, labeling or tagging) are integrated with the electrical detector on a chip.

Other methods known in the art for observing, measuring or characterizing nucleic acids such as DNA or RNA can be used in conjunction with the electrical detector to rapidly and precisely confirm or augment the electrical detector's measurement of conformation, length, speed, and fluorescence intensity of single nucleic acid molecules constrained by a nanofluidic channel in the electrical detector. Such additional data could be used, for example, to support conclusions drawn from length measurements and probe position measurements made electrically. Though such information could be used in conjunction with electrical detection, it would not provide the same spatial resolution afforded by the electrical detector.

For example, if the substrate or the floor or ceiling of the nanochannel of the electrical detector is transparent, fluorescent detection can be used simultaneously with electrical detection. Length measurements provided by optical detection are effective and convenient methods to rapidly confirm the length measurements made using electrical detection. While such optical measurements are not likely to have as high resolution as electrical measurements, the additional data they generate could be correlated with electrical measurement data and would increase confidence in any conclusions drawn from electrical measurement data. It may not be desirable to utilize the option of optical detection in every detection situation, however. For example, if portability is important, then bulky optical systems are not ideal.

In one embodiment, as described in Section 6.5, charged molecules can be driven electrophoretically from a nanoslit into a nanochannel to confine and dynamically elongate them beyond their equilibrium length for repeated detection via laser-induced fluorescence spectroscopy. A single-molecule analysis algorithm can be used to analytically model bursts of fluorescence and determine the folding conformation of each stretched molecule.

6. EXAMPLES

6.1 Example 1: Nanofluidic Channels with Integrated Carbon Nanotube Charge Sensors

6.1.1 Introduction

This example demonstrates that a electrical detector comprising a nanofluidic channel and a carbon nanotube sensor integrated in the nanofluidic channel can be used as means for electronically detecting charged molecules in a highly confined environment while allowing for simultaneous fluorescent observation. Subsequent Examples (Sections 6.2-6.4) describe methods for fabricating electrical detectors comprising a nanofluidic channel and a charge sensor integrated in the nanofluidic channel, wherein the charge sensor is a nanowire or nanotube.

Individually addressable, semiconducting, single-walled carbon nanotubes were incorporated into fluid-filled channels with depths of 15-100 nm and widths of 500 nm. Given appropriate buffer conditions, channels of this size are comparable in depth to the length scale of ionic screening. Thus, charged DNA molecules travelling through the nanochannel will gate the semiconducting nanotube, causing a shift in current at constant source drain bias. This electrical detector, employing fluid filled channels of this size is also useful because it allows for confinement induced partial elongation of genomic length DNA molecules.

This example describes an electrical detector in which a single wall carbon nanotube (SWCNT) is integrated into a nanoscale fluidic (nanofluidic) channel. Diagrams depicting the electrical detector geometry and experimental procedure are shown in FIG. 3. A SWCNT sensor, contacted by source and drain electrodes, was incorporated into a nanofluidic channel in such a way that only the middle segment of the nanotube was disposed within, i.e., inside of, the channel and in contact with the electrolyte solution of interest.

The nanofluidic channel can also be used to elongate and confine DNA molecules so that, as the DNA molecules are driven through the channel, they are forced to pass within close proximity to the nanotube sensor. The nanotube can be used in a field effect transistor (FET) mode to detect the perturbation in solution potential caused by the passage of DNA. The change in nanotube conductance was observed by applying a constant source-drain bias voltage and monitoring the current through the nanotube.

FIG. 3 is a schematic diagram showing top down view of the electrical detector and method disclosed in this example. The electrical detector comprised single-walled carbon nanotubes integrated into a nanofluidic channel such that the current through a nanotube could be monitored while DNA molecules were driven through the channel. During fabrication, a chemical vapor deposition method was used to grow nanotubes from metal catalyst pads.

As is depicted in FIG. 3, nanotubes grow with a distribution of lengths and directions and in some cases a nanotube lands such that it connects the source and drain electrodes. A combination of microfluidic and nanofluidic channels was used to guide single DNA molecules toward the connected nanotube.

In one embodiment, a molecule can be slowly driven through the nanofluidic channel. When its position coincides with an electrically connected semiconducting nanotube, the nanotube conductance will be altered by means of field effect gating.

Unlike other nanotube or nanowire biosensing experiments, this approach employs nanotube detectors for the purpose of sensing unbound biomolecules, as opposed to prior art reports that demonstrate gating of chemically functionalized nanotubes (Katz, E. and I. Willner, Biomolecule-functionalized carbon nanotubes: Applications in nanobioelectronics. Chemphyschem, 2004. 5(8): p. 1085-1104).

It has also been shown in the literature that carbon nanotubes integrated into micrometer-sized PDMS channels can be used to detect shifts in local solution potential induced either by redox reactions at an electrode interface (Larrimore, L., et al., Probing electrostatic potentials in solution with carbon nanotube transistors. Nano Letters, 2006. 6(7): p. 1329-1333), or by streaming potential caused by pressure driven flow of an electrolyte through the channel (Bourlon, B., et al., A nanoscale probe for fluidic and ionic transport. Nature Nanotechnology, 2007. 2(2): p. 104-107). In the embodiment described in this example, only a change in the solution potential is responsible for gating the nanotube.

6.1.2 Theory

Double-stranded DNA in physiological solution is a highly charged macromolecule, with an estimated surface potential of order −100 mV (Wagner, K., et al., Analytical Debye-Huckel model for electrostatic potentials around dissolved DNA. Biophysical Journal, 1997. 73(1): p. 21-30). In an ionic solution, rearrangement of mobile charge carriers serves to screen the large surface potential of DNA over a characteristic length scale termed the Debye screening length. It may be for this reason that previous attempts to detect DNA with nanotubes or nanowires have focused on cases in which the DNA molecules are bound to the surface of the detector.

In this example, an electrical detector was designed and fabricated in which DNA molecules driven through a nanofluidic channel were forced to pass close enough to the nanowire detector such that the solution potential at the location of the detector was perturbed (FIG. 4).

FIG. 4 shows a side view of an electrical detector with a schematic of an elongated DNA molecule in the channel. Two single walled carbon nanotubes (circular cross section shown) run perpendicular to the axis of the nanofluidic channel and the image plane. They are contacted by two source and drain electrode pairs that are not shown here. A DNA molecule travelling through the channel moves from left to right in the image. The negatively charged DNA molecule (red) is surrounded by a cloud of positively charged ions. At a distance y from the DNA backbone, the solution potential is perturbed by an amount $\Delta\varphi_{DNA} = \zeta \cdot \exp(-y/\lambda_D)$ from its bulk value. A perturbation of potential at the nanotube surface gates the electrical detector, affecting its conductance. This is measured as a change in current at constant source drain voltage.

In an electrolyte solution, near the surface of a charged object, the electric potential transitions from the zeta potential (electric potential of the immobile ions fixed to the surface) to the bulk solution potential over a distance that depends on the ionic strength of the solution. A convenient parameter for describing that drop in potential is the Debye screening length, $\lambda_D$, which is defined by the expression $\lambda_D =$ $\sqrt{(\varepsilon RT)/2F^2(\Gamma/2)}$ where $\Gamma/2$ is the ionic strength of the solution. Using the Debye-Huckel approximation, the shift in electrolyte potential a distance, y, from the DNA surface is then given by $\Delta\varphi_{DNA}=\zeta \cdot \exp(-y/\lambda_D)$.

In the embodiments of the electrical detector disclosed in this example, carbon nanotubes were located close enough to the backbone of confined DNA molecules so as to avoid significant charge screening. For a carbon nanotube fixed to the bottom surface of the nanofluidic channel, and a DNA molecule elongated in the channel and positioned above the nanotube, the average nanotube/DNA separation distance is roughly half of the height of the channel. Given a DNA zeta potential of 100 mV, an ionic screening length of 10 nm, and a channel depth of 50 nm a perturbation in solution potential on the order of 10 mV was expected at the location of the nanotube. In theory, fluctuations in the conformation and vertical position of the DNA molecule owing to thermal agitation may cause fluctuations in potential near the nanotube sensors. It was assumed, however, that such fluctuations occur on a timescale that is short compared with the duration of the measurement, thus they can be ignored.

Having estimated the magnitude of the potential shift caused by a DNA molecule, the change in nanotube conductance that results was calculated. For semiconducting carbon nanotubes (CNTs) in solution high mobilities, low contact resistances, and good gate coupling are possible (double layer capacitance of $4\times10^{-9}$ F·m$^{-1}$), leading to an electrolyte gated transconductance of $\sim e^2/h/V$ (Rosenblatt, S., et al., High performance electrolyte gated carbon nanotube transistors. Nano Letters, 2002. 2(8): p. 869-872). Applying an electrolyte gate voltage of 10 mV should result in a conductance change of order $0.01V \cdot e^2/h/V = 387$ nAmp·$V_{SD}^{-1}$.

This is an upper bound, however, as it assumes the potential along the entire length of the nanotube has been shifted by $\Delta\varphi_{DNA}$. Given the device design and a ionic screening length of roughly 10 nm, only a fraction of the length of the nanotube will be affected by the DNA potential. Even so, according to theoretical calculations it is likely that such a perturbation in solution potential could be detected.

Much work has been done on scanning gate microscopy of carbon nanotubes (Bachtold, A., et al., Scanned probe microscopy of electronic transport in carbon nanotubes. Physical Review Letters, 2000. 84(26): p. 6082-6085; Freitag, M., et al., Controlled creation of a carbon nanotube diode by a scanned gate. Applied Physics Letters, 2001. 79(20): p. 3326-3328; Kim, Y., et al., Mapping potential landscapes of semiconducting carbon nanotubes with scanning gate microscopy. Nanotechnology, 2007. 18(47); Zhang, L. M. and M. M. Fogler, Scanned gate microscopy of a one-dimensional quantum dot. Nano Letters, 2006. 6(10): p. 2206-2210), which supports this notion. The results presented in this example suggest that local gating of nanotubes from scanning probe AFM tips can affect nanotube conductance even when the affected length of the nanotube is on the order of tens of nanometers (Freitag, M., et al., Controlled creation of a carbon nanotube diode by a scanned gate. Applied Physics Letters, 2001. 79(20): p. 3326-3328). While it was reported by Freitag et al. that the strongest gate coupling effects occurred near the contacts, the nanotube may also be gated to varying degrees anywhere along its length. For the embodiment of the electrical detector disclosed in this example, the way in which DNA gating is expected to modulate nanotube band structure is illustrated in FIG. 5.

FIG. 5A shows a cross-sectional diagram of an electrical detector comprising a nanofluidic channel with integrated nanotube charge sensor. The source and drain contacts to the carbon nanotube are buried under an insulating layer of silicon nitride. The nanofluidic channel confines the electrolyte solution over the central part of the nanotube only, and forces the DNA molecule to reside at a vertical position that is close to the nanotube. Since the channel width is larger than its depth, the DNA molecule has more freedom in the lateral dimension.

FIG. 5B shows a band diagram of a p-type nanotube integrated into the nanofluidic channel of the electrical detector. If the solution potential is more negative relative to the source and drain electrodes, then a first perturbation (dotted line, broad curve) to the band diagram results. If the potential from the DNA molecule is significant enough, a second perturbation (gray solid line, small curve) will exist in the conduction and valence bands.

Modulation of band structure and the mechanism of electrolyte gating for nanotubes has been previously investigated and is known in the art? Over the past several years, a number of theories have been proposed to explain the mechanism of nanowire transconductance in electrolyte solution, for a detector design such as the one shown in FIG. 6A. Schottky barrier modulation, electrostatic gating of nanotube carrier density, capacitance effects between the nanotube surface and the solution, and decreased electron mobility through the nanotube have all been proposed.

Heller et al. has argued that, according to theory, each of these mechanisms should affect the I·$V_{lg}$ (current vs. liquid gate) curve in a qualitatively distinct way (Heller, I., et al., Identifying the mechanism of biosensing with carbon nanotube transistors. Nano Letters, 2008. 8: p. 591-595). A comparison of experimental data with models for the four different mechanisms suggests that electrostatic gating of carrier density and Schottky barrier effects are primarily responsible for conductance changes upon biomolecule binding for the setup shown in FIG. 6A. Furthermore, when the contacts are covered as in FIG. 6B, and only a portion of the SWCNT is exposed to solution, the affect of biomolecule binding on I·$V_{lg}$ is shown to be consistent with the model for gating of carrier density in the nanotube. The latter situation is most similar to the electrical detector, for which the nanotube/platinum contacts are imbedded under a silicon nitride film and only a central portion of the nanotube is in contact with the solution. Eventually, DNA molecules, as they are driven through the channel, will also be confined to interact with the exposed central segment of the nanotube only.

Figure 6:
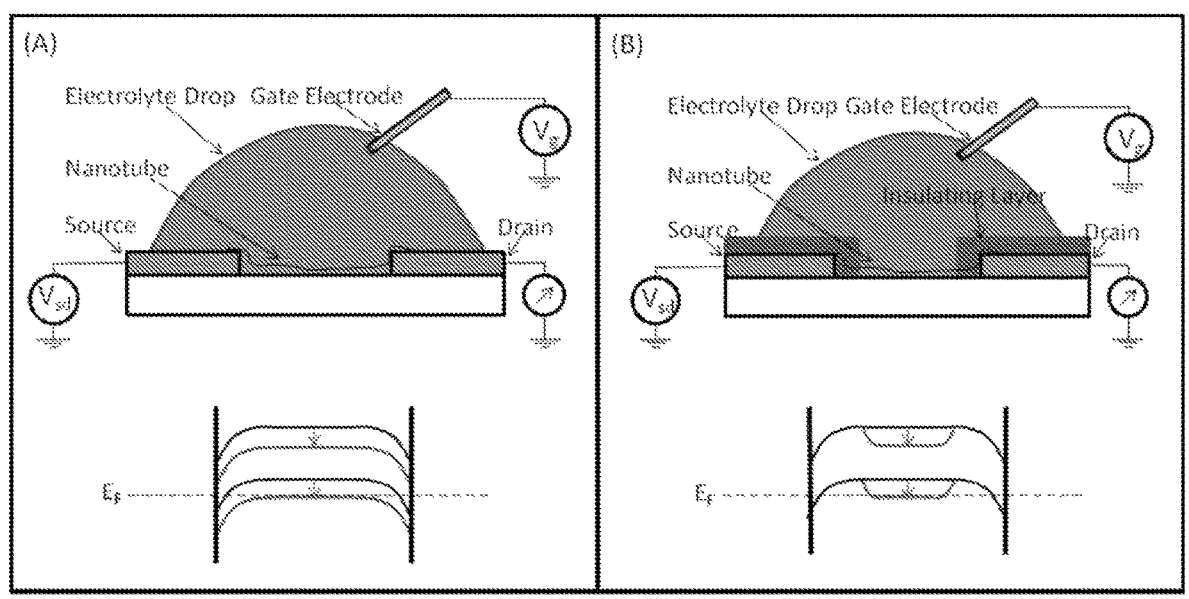

FIG. 6 illustrates the setup for electrolyte gate sweeps of carbon nanotubes, and the resulting effects on band structure, adapted from results reported by Heller et al. (Identifying the mechanism of biosensing with carbon nanotube transistors. Nano Letters, 2008. 8: p. 591-595). The black band diagrams indicate an ungated, p-type nanotube. The light gray diagrams depict a shift toward depletion as the gate voltage is made more positive relative to the source and drain. FIG. 6A shows unprotected nanotube source-drain contacts. In this case, both Schottky barrier modulation and carrier density gating were found to be responsible for modulating the nanotube conductance. FIG. 6B shows nanotube source drain contacts electrically isolated from the solution by some insulating layer. In this case, the Schottky barrier modulation may be eliminated as a possible mechanism of nanotube conductance modulation.

6.1.3 Materials and Methods

Electrical Detector Fabrication

To combine leak-free, nanoscale fluidic channels with functioning carbon nanotube transistors, a fabrication process was developed that employed standard photolithographic and MEMs processing techniques and carbon nanotube growth processes known in the art. An overview of electrical detector fabrication is given here. Further details are available in Section 6.2-6.3. For the embodiment of the electrical detector described in this example, a sacrificial layer method was used to create channels with integrated electronic elements.

Initially, an alignment mark level was patterned and etched into 170 μm thick and 100 mm diameter fused silica wafers (Mark Optics). A patterned layer of chromium, 10-50 nm thick, was then deposited using a combination of photolithography, ebeam evaporation and lift off. This patterned chromium layer is the sacrificial material for what will be a network of micro- and nano-fluidic channels in the end. A thin layer (10-30 nm thick) of low stress nitride was conformally deposited on top of the chromium using a plasma enhanced chemical vapor deposition tool. This thin nitride layer protects the chromium from reaction with process gases during the carbon nanotube growth step. Next, patterned layers of Ti/Pt (thicknesses 4 nm/30 nm) for contact electrodes and $Al_2O_3$/Co (15 nm/3 Å thicknesses) for catalyst pads were deposited on separate layers using a combination of photolithography, ebeam evaporation and lift off. The wafers were then diced into chips using a KS 7100 Wafer Saw.

Next, carbon nanotube growth was performed on individual chips using a chemical vapor deposition (CVD) process at 800° C. with ethylene as the carbon source precursor. Following growth, a second layer of low stress nitride of thickness~2 μm was deposited using PECVD. Access holes were then created along the length of the channels, and over the Pt pads for needle contact using photolithography and dry etching ($CHF_3/O_2$) in an Oxford 80 Reactive Ion Etch (RIE) Machine (Oxford). After photoresist stripping, chips were submerged in CR-14 Chrome Etchant (Cyantek) for 3-6 hrs, during which time the liquid etchant travelled through the access holes and removed the sacrificial layer of chromium. Chips were soaked in dH2O and then IPA (15 min in each) and then dried with $N_2$. At this point CNT conductances were checked.

The thin layer of protective nitride separating the CNTs from the channel was etched away by submerging chips in MF 312 (5% TMAH) at 70° C. for anywhere from 15 to 45 min, depending on the protective nitride layer thickness. Following this, chips were soaked in $dH_2O$ and then IPA (15 min in each) and dried again with $N_2$. A third and final layer of low stress silicon nitride of thickness 500 nm was deposited. This layer served to seal the etchant access holes along the length of the micro- and nanofluidic channels.

Finally, the newly deposited 500 nm thick nitride film above the Pt pads was removed using a combination of photolithography and dry etching to allow for probe needle contact. After stripping resist off of the chip surface, entrances were created at the end of the six microchannels by lightly scratching the nitride with a diamond scribe, and macroscopic reservoirs were aligned by eye and affixed to the chip above the microchannel entrances.

Observation Setups

Optical setup. Fluorescfence observation of single DNA molecules in nanofluidic channels was performed with an IX71 inverted microscope (Olympus, Melville, N.Y.), equipped with a 100x/1.35 NA oil immersion objective (Olympus). Images were acquired using a Cascade 512b EMCCD (Photometrics) at 10 frames per second using software written in Labview (National Instruments). Videos were saved as a series of .tif files and analyzed using a MATLAB program.

Electrical setup. To simultaneously monitor nanotube conductances while visualizing DNA molecules near the nanotubes, an electrical setup was assembled with the optics as shown in FIG. 7. Pt electrodes were placed in the fluid reservoirs and were used to electrokinetically drive DNA molecules through the channels. In another embodiment, the Pt electrodes can be replaced by Ag/AgCl reference electrodes during detection, as described in Section 6.1.4 (Results and Discussion). Two to four probe manipulators (Quarter Research, Bend, Oreg.) were attached to the stage using vacuum mounts, and these were used to place probe needles in contact with the source and drain electrode pads. Source electrode voltage was interfaced to a DAC and controlled using a freely available freeware LABVIEW program MeasureIt.vi. Current between the drain electrode and ground was monitored using an Ithaco 1211 current preamplifier (DL Instruments, Ithaca, N.Y.), the output of which was fed to an ADC and recorded using the same LABVIEW program. The current preamplifier gain was set between $10^7$ and $10^9$ and the time constant between 3 ms and 100 ms. Sampling rates were set to be equal to or less than the inverse of the time constant, ensuring statistical independence of recorded measurements. FIG. 7 shows the experimental setup for simultaneous optical and electrical detection.

6.1.4 Results and Discussion

Measurement of Carbon Nanotubes in Air

To verify the presence of carbon nanotubes (CNTs) throughout the fabrication process, electrical detector conductances were recorded after initial CNT growth while the nanotubes were still exposed to air. Each of the 38 source and drain electrode pairs on each chip could be individually addressed and tested for nanotubes. Because of the random nature of carbon nanotube growth with CVD, it was not known a priori how many nanotubes bridged the gap between each source and drain electrode. Immediately after growth, some electrode pairs exhibited no current in response to a source drain bias, and these were considered to have no nanotube bridging the gap between the electrodes. Although it is conceivable that in those cases an SWCNT was there but was simply depleted of charge carriers, this is believed to only rarely have been the case. This is based on many subsequent measurements in which water gates were used. Most of the time, if a nanotube was present, at least some small current could be detected at large source drain bias. If a current existed, it was assumed that at least on nanotube bridged the gap. For most of the chips, more detailed information was not obtained regarding nanotube growth at this stage. Each chip was simply characterized by the number of connected source drain electrode pairs. If at least a few were connected, then processing steps were continued on that chip. Depending on the wafer or CVD growth run, the majority of chips in a run had between 5 and 30 connected electrode pairs, out of a possible 38. The I-Vsd curves for the majority of connected electrode pairs showed electrical detector resistances ranging from 100 kΩ to 10 MΩ, with mean square current noise densities of $10^{-17}$ $Amp^2/Hz$ to $10^{-15}$ $Amp^2/Hz$ at a source drain bias of 10 mV.

Following deposition of the nitride capping layer on the nanotubes, the conductances were observed to change. This was attributed to charges associated with the nitride/nanotube interface (Chen, B. H., et al., A carbon nanotube field effect transistor with tunable conduction-type by electrostatic effects. Solid-State Electronics, 2006. 50(7-8): p. 1341-1348; Kojima, A., et al., Air stable n-type top gate carbon nanotube filed effect transistors with silicon nitride insulator deposited by thermal chemical vapor deposition. Japanese Journal of Applied Physics Part 2—Letters & Express Letters, 2005. 44(8-11): p. L328-L330; Mizutani, T., et al., Effects of fabrication process on current-voltage characteristics of carbon nanotube field effect transistors. Japanese Journal of Applied Physics Part 1—Regular Papers Short Notes & Review Papers, 2005. 44(4A): p. 1599-1602). Additionally, the noise level for many nanotubes appeared to go down. This was also attributed to the direct contact between nitride and nanotubes.

Electrolyte Gated Measurements

Because no metal gate existed on the chips, the shifts in conductance were analyzed as follows. While a water gate could be used before nitride deposition, water gating appeared to be ineffective, even after a small amount of nitride had been deposited. Nevertheless, a comparison of water gating response could be made between tubes that were just grown, and those that were in fully fabricated electrical detectors (where the protective nitride layer had been removed and part of the tube was in contact with the nanofluidic channel buffer). CNT devices with exposed surfaces could be investigated using an electrolyte gate as was first demonstrated for multiwalled nanotubes (Kruger, M., et al., Electrochemical carbon nanotube field-effect transistor. Applied Physics Letters, 2001. 78(9): p. 1291-1293) and later for single walled nanotubes (Rosenblatt, S., et al., High performance electrolyte gated carbon nanotube transistors. Nano Letters, 2002. 2(8): p. 869-872). Source and drain electrodes were contacted in the normal way, but a drop of salty water was placed directly on top of the nanotubes and this electrolyte solution was then gated with a Pt or Ag electrode, as shown in FIG. 6A. The electrolyte potential was swept between −800 mV and +800 mV relative to the drain potential. Gate potentials beyond about ±1V were observed to destroy the electrical detectors, an effect which is attributed to electrochemical oxidation or reduction of the electrodes, or of the nanotube itself.

Typical I-V curves for a semiconducting device are shown in FIG. 8.

FIG. 8A shows source drain current vs. electrolyte gate sweep for two source drain voltages. For $V_{SD}=0$, the measured I is entirely owing to $I_{GD}$, the electrochemical leakage current between gate and drain electrodes. A gate sweep which goes from a positive to a negative value and loops is equivalent to a cyclic voltamogram in the electrochemistry literature. The shape of the curve is determined by either mass transport or electron transfer kinetics and is a function of sweep rate among other parameters (Bard, A. and L. Faulkner, *Electrochemical Methods*. 2001: John Wiley & Sons). For a given sweep rate and electrode surface area, the leakage current may be measured, as is shown above, and later subtracted. FIG. 8B is a graph plotting current versus source-drain voltage for three differed gate potentials. It is apparent from these curves that a shift in gate potential on the order of 50 mV can be measured easily.

It was common for an electrical detectors with a single carbon nanotube to exhibit ambipolar behavior. At zero and negative gate voltage, these nanotubes were often p-type. The application of a large positive gate voltage resulted in n-type behavior. In accordance with previously defined metrics for characterization of semiconducting nanotubes, the electrical detector disclosed in this example can be characterized by a transconductance value for both the n-type and p-type regions.

For electrolyte gate sweeps, the measured current, I, is a sum of the current between the source and the drain $I_{SD}$ and the leakage current between the gate and drain electrodes $I_{GD}$. Each of these components can be broken down further. The source drain current is the sum of the electrical current passing through the nanotube and the ionic current between the source and drain electrodes. The gate-drain current is the sum of the current between the gate and the exposed area of the drain electrode surface, and the gate and nanotube. Depending on the values of $V_G$ and $V_{SD}$, and the electronic properties of the nanotube, one of the possible contributions to total current may dominate at a given time.

When initially analyzing the data for completed electrical detectors with nanotubes, it was believed that there was a small leakage current caused by either: 1) electrolytic current between the gate and drain that was travelling through inter dielectric layer spaces caused by nanotube topology, or 2) a leakage current between the gate the carbon nanotube surface directly. Analysis of the $V_{SD}=0$ data in FIG. 9 revealed some small negative current at large gate values. This appeared to support the notion of a small leakage current.

FIG. 9 (main panel) shows current versus electrolyte gate voltage at a variety of source-drain biases for a nanotube integrated into a nanofluidic channel of the electrical detector. This particular nanotube shows ambipolar behavior. At its highest the transconductance is approximately 25 $\mu S/V_G$. FIG. 9 (inset) shows a semilog plot of current versus gate at 100 mV source drain bias. The exponential decay is characterized by a subthreshold swing (inverse of slope of dashed line) of S=185 mV/decade.

In fully fabricated electrical detectors, the observed current at zero source drain bias current was not a leakage current at all. It appeared instead to have been the result of an ambient voltage difference between the source and drain electrodes. Although the source electrode was set to zero volts, it differed from the drain potential by some small negative voltage. The small bias then resulted in a current which was modulated by the gate potential, but which was not a result of leakage between the gate and the drain. Evidence for this is given in FIG. 10 and FIGS. 11A-D.

FIG. 10 shows the difference in gate-drain leakage current for buried versus exposed electrodes. FIG. 10 plots leakage currents for buried versus exposed electrodes. Leakage currents between the gate and drain electrodes for two separate electrical detectors are graphed. One data set (labeled) is for a partially fabricated device, where the source and drain electrodes were exposed, and in contact with the electrolyte as in the diagram of FIG. 6A. The other data set (labeled) is for a fully fabricated device, where the source and drain electrodes were buried under silicon nitride and are separated from the electrolyte solution, as depicted in FIG. 5. Both of electrical detectors measured here were believed to have no nanotube connecting the source and drain electrodes. While the plots shown are for a bias of 100 mV, the current response was nearly identical to this for biases of 0 mV, 1 mV, and 10 mV. The main result here was the difference in leakage current for buried versus exposed electrodes. No gate drain leakage current for the buried electrodes was apparent. For the exposed electrode, the leakage current took the form a cyclic voltammogram, as expected for mass transport limited heterogeneous reactions.

FIGS. 11A-D show the gate sweeps for four different electrical detectors where the nominal source drain biases were set to 0 mV and 10 mV. FIGS. 11A-D plot current versus gate potential for four different source drain electrode pairs for a fully fabricated electrical detector (i.e., contact electrodes covered by nitride). Each pair investigated here had either one or more semiconducting carbon nanotubes connected. The top data set in each graph corresponds to a nominal source drain bias of 1 mV. The magnitude of the current for these data sets is given on the y-axis.

The bottom data set in each graph corresponds to a nominal source drain bias of 0 mV. These data set values have been multiplied ten times for ease of viewing. Thus, the maximum currents recorded for these data sets in A, B, C, and D were −3.3 nA, −1 nA, −2 nA, and −2 nA. There was a small ambient offset source drain voltage of approximately −0.1 mV. Evidence suggests that there was little, if any, leakage current.

Fluorescence Video Monitoring of DNA Near Nanotube

Fluorescence video was taken of DNA molecules travelling through nanofluidic channels under electrophoretic motion. Single T4 molecules (120 kbp in length) and fragments were readily observed and quickly driven to the nanotube region of the electrical detector (FIG. 12). Once there, the molecules could be positioned using small voltages. This level of control allows for a DNA molecule to be positioned so that it rests directly above a nanotube for an extended period of time, while the nanotube conductance is monitored.

FIG. 12 (left) is a schematic diagram of DNA molecules in and near the nanofluidic channel region of the electrical detector. In this diagram, two molecules are in the channel at the same time. By applying a small voltage (~1V), the molecules may be slowly driven up or down in the channel. FIG. 12 (right) is a time trace diagram of two DNA molecules in a nanofluidic channel of an electrical detector with a carbon nanotube charge sensor. The first molecule enters the channel at time t=0 sec. and the second molecule enters at t=25 sec. At t=29 sec, the direction of the electric field is reversed, causing the two molecules to change their direction of migration.

Factors Contributing to Electronic Noise

As a first step in determining the noise floor of the system, the current noise inherent to liquid gated carbon nanotube transistors was estimated. Owing to the nature of the DNA detection approach, low frequency noise power (approximately 1 Hz and lower) was of most interest. Much research on the noise properties of SWCNTs has been performed and 1/f noise has been demonstrated.

The noise spectra of the source drain current, I, as a function of frequency, f, has typically been interpreted from the point of view of the Hooge model (Hooge, F. N., 1/F Noise Sources. IEEE Transactions on Electron Devices, 1994. 41(11): p. 1926-1935). In this model, noise is caused by independent scattering events of charge carriers. Recently Mannik et. al have interpreted 1/f noise in nanotubes differently, using a charge-noise model (Mannik, J., et al., Charge noise in liquid-gated single-wall carbon nanotube transistors. Nano Letters, 2008. 8: p. 685-688). In this model, low frequency noise is caused by charge fluctuations that are either near the nanotube or that transiently associate with the nanotube surface. Examples of such charge fluctuations may be dissociation of hydrogen from silanol groups on a substrate surface near the nanotube or adhesion of an ion in solution to the nanotube surface. This indicates that the current-noise power, $S_I(f)$, should be proportional to a factor describing the magnitude of charge fluctuations, $S_{input}$, multiplied by the square of the nanotube transconductance $(dI/dV_G)^2$.

In addition to showing that the low frequency noise spectra is governed by charge-noise phenomena, Mannik et al. demonstrate a dependence of noise power on nanotube length (Mannik, J., et al., Charge noise in liquid-gated single-wall carbon nanotube transistors. Nano Letters, 2008. 8: p. 685-688). Mannik et al. shows that $S_I(f) \propto 1/L$ holds for nanotubes of 2 nm diameter, with lengths ranging from 60 nm to 3.4 μm, a range of sizes within which our nanotubes fall. To obtain an order of magnitude estimate for the electrical detectors, Mannik et al.'s value for current noise spectral density for the 440 nm long CNT sensor was used for the estimate of device noise. For a 1 Hz bandwidth and a source drain voltage of 10 mV, Mannik et al. found a current noise spectral density at f=1 Hz which varied from $10^{-26}$ to $10^{-18}$ Amp$^2$/Hz as the liquid gate potential was swept. This corresponds to an RMS uncertainty in the current of between approximately 0.5 pA and 5 nA for a source drain bias of $V_{SD}$=10 mV 10 mV and a rise time of 30 msec.

The nanofluidic and microfluidic channel system connecting the macroscale fluidic reservoirs acted as a resistor and was considered as a second source of noise. The voltage variance per hertz of bandwidth attributed to Johnson noise is given by $v_n^2$=4 $k_H$TR. To calculate the voltage variance at the location of the nanotubes, resistances of the various parts of the fluidic system can be calculated using geometrical considerations and known values for buffer resistivity. A simple case was considered in which a single nanotube is located at the center of a nanochannel that is connected to microchannels in series only. A buffer resistivity ρ and a resistance for each channel segment given by ρ·g was assumed, where g=l/(d·w) is a geometrical factor with l, w and d equal to the channel segment's length, width and depth respectively.

All channels in the model are of the same depth, which is set to d=100 nm in this calculation. For purposes of the calculation, the first microchannel is approximated as 5 mm long and 30 μm wide. The second microchannel is approximated as 1 mm long and 5 μm wide, and the nanochannel is approximated as 5 μm from the end to its middle, and is 500 nm wide. Thus the geometrical factors are $g_1$=1.7×10$^9$ m$^{-1}$, $g_2$=2×10$^9$ m$^{-1}$ and $g_3$=1×10$^9$ m$^{-1}$.

At low ionic strength, the resistivity for an electrolyte in a nanoscale channel, $\rho_{nano}$, differs from the bulk resistivity, $\rho_{bulk}$, by an appreciable amount, as reported by Stein et al. (Stein, D., M. Kruithof, and C. Dekker, Surface-charge-governed ion transport in nanofluidic channels. Physical Review Letters, 2004. 93(3)). Stein et al. investigated channels with depths ranging from 70 nm to 1015 nm and observed that channel conductance decreases with depth and with ionic strength. It also reports a conductance saturation level at very low ionic strength, an effect that is explained by the dominance of surface charge governed ionic transport. It is in this concentration regime that the electrical detector operates.

The reported value of Stein et al. was used in the resistivity estimate. Given that saturation conditions are satisfied, $\rho_{nano}$·d≈2·10$^8$Ω·(width/length) regardless of channel height. Using this value, the total resistance for the channels was estimated, assuming that ionic strength was low enough that surface governed ionic transport dominates conductance. Given the channel geometry, R=(ρ·d)·L·w$^{-1}$= (2·10$^8$Ω)·(10$^{-3}$ m/10$^{-5}$ m)=2·10$^{10}$Ω. Thus, at the location of the nanotube, the voltage variance per hertz of bandwidth attributed to thermal motion of fluid in the channels is $v_n^2=4 k_H TR=3.3\times 10^{-10} V^2 Hz^{-1}$. Through field effect, this translates to a Johnson induced current noise of $S_J(f)=v_n^2 \cdot (dI/dV_{1g})^2=3.3\times 10^{-10} \cdot (3.87\times 10^{-5})^2 \approx 50\times 10^{-20}$ Amp$^2$/Hz at $V_{SD}=10$ mV, where the frequency dependence is trivial since thermal agitation across a resistor leads to a white noise spectrum. Note that the actual system of channels is more complicated in that there are six reservoirs as opposed to two (see Section 6.2). There are also six microchannel loading arms leading to each of the reservoirs, and nineteen nanofluidic channel branches in parallel. Nevertheless the simple case described here gives a rough estimate of the Johnson noise for this type of fluidic system, and from that an estimate was obtained of its contribution to nanotube current noise.

As a third contributor to current noise, the interface between the reservoir electrodes and the buffer was considered. Chemical interactions at an electrode interface can cause additional variations in solution potential. This has been examined by Minot et al. (Minot, E. D., et al., Carbon nanotube biosensors: The critical role of the reference electrode. Applied Physics Letters, 2007, 91). Minot et al. showed that, when performing biosensing measurements with carbon nanotubes, it is critical to use a reference electrode separated from the solution by a frit to accurately control the solution potential. It points out that many previously reported nanowire biosensing experiments employed bare electrodes in solution, which can lead uncertainty in knowledge of solution potential over time. For example, for a Pt electrode immersed in bovine serum albumin with target protein molecules, interactions at the electrode surface can cause shifts in global solution potential on the order of 20-40 mV.

In the present example, one might imagine that aggregates of DNA molecules, pieces of crystallized salt, or other particles diffusing in the macroscopic reservoir might interact with a bare electrode and cause a similar shift in global solution potential. Because the "signal" perturbation from the DNA molecule is only expected to be on the order of 10 mV, interactions between electrode surface and solution impurities should be avoided. To prevent this, Ag/AgCl reference electrodes can be used: immersed in a highly concentrated AgCl solution and separated from the bulk solution in the reservoir by a frit. Such a reference electrode can hold the solution potential steady to within 1 mV. Thus it was estimated that the effect of the reference electrode/solution-impurity interactions contribute 1 mV RMS fluctuations in background noise, leading to a current noise PSD of $S_E(f)=(1\text{ mV})^2 \cdot (dI/dV_{1g})^2 = 15\times 10^{-14}$ Amp$^2$/Hz at $V_{SD}=10$ mV.

As a final possible source of noise, the measurement equipment itself was considered. The preamp gain was selected to be significantly larger than the source dynamic impedance, $R_d$, to keep the preamp from adding substantially to the source noise. For a gain of $10^7$ and a rise time of 1 ms, the nominal preamp current noise was on the order of 50 fA (DL Instruments, Applying the Model 1211 Current Preamplifier to Tunneling Microscopy 1987; available from: http://www.dlinstruments.com/technotes/technotes.html). This was much smaller than the noise from any of the other sources. Other factors such as 60 Hz pickup and acoustic vibrations are also likely contributors to noise. However, these were not estimated as they depended largely on the details of the setup. It was assumed that, with effort, their noise contribution could be made smaller than that of other sources of noise considered above.

6.1.5 Conclusion

The integration of carbon nanotube sensors into nanofluidic channels represents a first step in electrical detection of unbound biomolecules. This example discloses the design and fabrication of a device for achieving this integration. Characterization of the optical and electrical properties of the device was also achieved.

Single DNA molecules were observed and manipulated in the detection region using a combination of electrokinetic driving forces and real time fluorescence video microscopy. SWCNTs built into a nanofluidic channel were gated through modulation of the solution potential. The gating characteristics differed from those of tubes on an open surface. Owing to insulation of the source and drain electrodes, leakage currents were reduced to a level that was below the noise.

6.2 Example 2: Fabrication of Device Comprising a Nanofluidic Channel with an Integrated Carbon Nanotube

6.2.1 Introduction

The electrical detector described in Section 6.1 was fabricated by a method that comprised a combination of standard micro-electro-mechanical (MEMS) processing techniques known in the art, as well as carbon nanotube growth techniques well known in the art. This example describes a preferred embodiment for a method for producing nanofluidic channel devices with integrated carbon nanotube sensors.

Section 6.3 sets forth a specific embodiment of the fabrication method.

6.2.2 Device Characteristics

Based on the concepts for electrical detection of charged DNA molecules in nanofluidic channels using integrated carbon nanotubes outlined in Section 6.1, an electrical detector comprising a nanofluidic channel and a charge sensor integrated in the nanofluidic channel preferably has the following characteristics:

(1) Nanofluidic channel depths are preferably on the order of the Debye screening length. For reasonably low ionic strength solutions, this screening length can be made as large as on the order of 10 nm.

(2) Nanofluidic channels are preferably connected to microchannels in such a way that it is possible to load DNA molecules into the channels and individually flow them over the integrated carbon nanotubes in a controllable way. Preferably, simultaneous optical observation of fluorescently labeled DNA molecules in the channels is conducted. Thus a fused silica substrate wafer with thickness of 170 μm is preferred.

(3) For the electrical detector to operate as intended, addressable semiconducting nanotubes that behave as electrolyte gated field effect transistors (FETs) are preferable. For the nanotubes to respond to small perturbations in solution potential, integrated carbon nanotubes are preferably in direct contact with the electrolyte solution in the channel.

There are several restrictions that these requirements place on the fabrication process.

(1) Some standard process for fabrication of nanoslits and nanochannels in fused silica cannot be employed. Processes that involve fusion bonding and high temperature annealing of two fused silica wafers to enclose the channels cannot be used. Fusion bonding requires that wafer surfaces are flat and clean (i.e. no bumps from electrodes or soot from nanotube growth). Typically, to sufficiently clean the surfaces, a wet chemical clean is used and this is followed by a high power oxygen plasma. After the oxygen plasma and touch bonding steps are performed, an overnight anneal in air at 1050° C. is used. Carbon nanotubes can survive neither oxygen plasma processes or a bake in atmosphere (specifically oxygen) at temperatures higher than ~300° C. Fusion bonding is of poor quality if structures such as electrodes are present on the wafer surface, and high temperature annealing would result in destruction of the nanotubes.

(2) To reliably drive molecules into the nanochannel detection regions, a network of loading channels preferably connects the detection region with a macroscopic fluidic reservoir. These channels should be leak free, and channel walls should be insulating. If photolithography is used, then the minimum aspect ratios required for channels with 10 nm depths necessitate that the channel wall and ceiling structures must be relatively stiff to avoid collapse. This, and the desire for leak free channels, discourages the use of PDMS as a channel structure, for example.

(3) The signal to noise ratio of the nanotube response to nearby DNA molecules will likely be low, perhaps even below unity. It is important then, that DNA molecules can be precisely positioned above the nanotubes and held in place for an extended period of time. This requires good visualization of the DNA molecules, in practice requiring that high numerical aperture objective lenses be used. It is therefore preferable to fabricate devices on 170 µm thick fused silica substrates. This permits the use of a 100×, 1.35 N.A., oil immersion lens, which is known to be adequate for visualizing single DNA molecules. In a preferred aspect, for single molecule fluorescent microscopy, the channel materials exhibit low autofluorescence.

(4) For nanotubes to be placed inside of the channel, growth preferably occurs before a number of other processing steps are performed. Growth of small diameter single wall carbon nanotubes typically requires the use of a catalyst such as Fe, or Co. Some thin film processing machines have sample restrictions. For example, samples with metals are banned from MOS furnaces. Such restrictions were necessary to consider during development of the fabrication method.

6.2.3 Methods

Device Fabrication Process Overview

This example describes one embodiment of the fabrication process. Other variations of this process will be apparent to the ordinarily skilled practitioner. This version was selected to optimize the yield and throughput of devices while meeting the basic requirements outlined above. While it is not necessary for the yield and throughput to meet the level of "high volume manufacturing," a phrase commonly used to describe industrial production levels, it is preferable to produce enough working devices that the device design can be thoroughly tested. Even a fully fabricated device with working nanotubes may easily be damaged during the experimental runs. That damage may take the form of electrolytic destruction of nanotubes contacting solution, or clogging of nanochannels, for example. By using the following process, the skilled practitioner can fabricate roughly 10-20 working devices within several weeks.

Device and its Geometry

The embodiment of the electrical detector disclosed in this example has a continuous system of microfluidic and nanofluidic channels that are connected to macroscopic fluidic reservoirs and to one or more nanofluidic channel detection regions, at which nanotube sensors are located. The fabrication method disclosed in this example produces one device per chip, where each chip is a 20 mm×20 mm piece of fused silica with various features constructed on one side. Each device contains 19 parallel nanochannel branches with a total of 38 separately addressable source/drain electrode pairs for contact with the imbedded carbon nanotubes. Diagrams of such an electrical detector are shown in FIG. 13.

FIG. 13 shows device diagrams. For ease of viewing, not all features within each image are drawn to scale relative to one another. When necessary, critical dimensions are indicated by red arrows and labels. Left top panel shows a view of a full fluidic network. Circles represent the six macroscopic reservoirs for loading fluid and DNA. Thick black lines represent fluidic channels used for transporting DNA into the electrical detector from the reservoirs. These channels are 40 µm wide, 100 nm deep, and several mm long. Support columns (not shown) in the middle of the loading channels help to prevent the ceiling structure from collapsing. The left and right loading channels are connected by 19 smaller microchannel branches, which are 6 µm wide and 100 nm deep. The top right panel is a close-up of region where 3 microchannel branches connect to the larger loading channel. This corresponds to the large black rectangle in 1A. The bottom left panel is a close up on center portion of a microchannel branch. This corresponds to the small black rectangle in the top left panel. As is drawn, two detection regions are present in each microchannel branch. The bottom right panel is a close-up of a detection region. Two platinum electrodes (a source and drain) are separated by a gap of 1 µm. The 6 µm microchannel branch tapers into a 500 nm nanochannel to thread the gap between the source and drain electrodes. An unspecified number of carbon nanotubes bridge the gap between electrodes. A portion of each nanotube exists in the nanochannel and is in direct contact with the fluid.

Major Fabrication Steps

The fabrication process can be broken down into 14 major steps and those are organized into 3 phases:

I. Cleanroom Processing on Full Wafers (Major Steps 1-3, shown below)
II. Carbon Nanotube Growth on Chips Diced from Full Wafers (Major Step 5 shown below)
III. Clean Room Processing on Chips (Major Steps 6-13, shown below)

Beginning with a 170 µm fused silica wafer, the 14 major fabrication steps are:

1) Alignment Layer
2) Pt/Ti Electrode Layer
3) Aluminum Oxide Supported Cobalt Catalyst Layer
4) Wafer Dicing
5) Carbon Nanotube Growth
6) Thin Silicon Nitride Layer
7) Microchannel/Nanochannel Sacrificial Chromium Layer
8) Thick Silicon Nitride Layer
9) Access Hole Layer #1 (For Wet Etch of Sacrificial Material)
10) Wet Etch of Sacrificial Material 11) Wet Etch of Thin Silicon Nitride Layer
12) Thin Silicon Nitride Layer #2 (For Enclosing Access Holes)
13) Access Hole Layer #2 (For allowing access of probe needles to source and drain contact pads)
14) Macroscopic Reservoir Attachment In the panels of FIG. 14, a diagram is used to illustrate only 9 of the 14 major steps, though below we make a few remarks about each of the 14 major steps.

FIG. 14 shows a select number of the 14 major steps. Only those steps which lend themselves to illustration are shown here. Each cross sectional image is labeled with its corresponding step number and name.

Step 1) Alignment marks (not actually shown) were etched into a 4 inch, 170 μm thick, fused silica wafer.

Step 2) Pt contact pads were deposited onto the wafer.

Step 3) Cobalt catalyst pads were deposited onto the wafer using photolithography, ebeam evaporation, and lift-off.

Step 4) Dicing (not shown).

Step 5) After dicing (illustration not shown), chips were placed into nanotube furnace for CNT growth.

Step 6) A 5-20 nm thin layer of silicon nitride was deposited on the wafer, covering the fused silica, Pt contact pads and nanotubes.

Step 7) A 10 nm thick, patterned layer of chromium was placed onto the wafer using photolithography, ebeam evaporation and liftoff.

Step 8) A 2 μm thick layer of low stress silicon nitride was deposited directly onto the nanotubes.

Step 9) Access holes defined along the length of the microchannels (not shown).

Step 10) After access holes were defined along the length of the microchannels (illustration not shown) the chromium sacrificial layer was selectively etched away using a CR-14 Chromium etchant (Cyantek).

Step 11) Wet etch of protective nitride layer, within which the nanotubes were buried. The etch height was controlled with a timed etch of heated MF-312 (5% TMAH, Microposit Corp.). The wet etch was followed by drying the channels, covering access holes with nitride, re-etching contact pad access, and installing macroscopic fluidic reservoirs, none of which is illustrated above.

Step 1, alignment layer. Fused silica wafers are initially featureless, and marks must be made on the wafer that allow for alignment of each of the subsequent lithography layers. Two types of alignment marks were employed in this process, which was designed for the GCA Autostep Aligner. Global GCA marks were used to perform a coarse alignment by eye. Micro-DFAS (Dark Field Alignment System) marks were then used to perform a fine alignment.

Step 2, Pt/Ti electrode layer. Source and drain electrodes for contacting carbon nanotubes were defined using photolithography, e-beam evaporation and lift-off. The electrodes were composed of Pt (30 nm thickness) and Ti (5 Å thickness). The purpose of titanium is to promote adhesion between the Pt metal and the fused silica wafer.

Step 3, aluminum oxide supported cobalt catalyst layer. Catalyst pads, for promoting nanotube growth, were defined using photolithography, e-beam evaporation and lift-off. The evaporated materials were Ti (5 Å), $Al_2O_3$ (15 nm), Co (2.5 Å). Titanium was used to promote adhesion between aluminum dioxide and fused silica. Aluminum dioxide was used for two purposes. First it is known in the art that catalyst deposited on aluminum oxide surfaces yields better growth than catalyst deposited on silicon dioxide. At least 10 nm is required so that a continuous film is achieved. Second, the thickness of the aluminum dioxide raises the position of the Co particles with respect to the Pt contact pad. This may increase the likeliness for a carbon nanotube to make it over the Pt during the growth stage.

Step 4, wafer dicing. Prior to carbon nanotube growth, the 4 inch (100 mm) device wafers were diced into 16 chips (20 mm×20 mm) using a wafer saw. Each of the chips contained one of the "devices" described in Section 6.2.2. This dicing step enabled the chips to fit in the carbon nanotube furnace. The fused silica furnace tube inner diameter was roughly 22 mm.

The wafer dicing process can cause damage to MEMs type structures. During development of the fabrication procedure, it was discovered that damage was being caused to areas of the fused silica between the source and drain electrodes. This problem was solved with the use of a thick resist coating to protect features from debris during dicing and changes to the device geometry, the length of the platinum wires was shorted, presumably reducing stress induced by the platinum.

Step 5, carbon nanotube growth. Single walled carbon nanotubes were grown using the art-known technique of chemical vapor deposition using a carbon nanotube furnace. One of two growth recipes was used depending on the desired yield of nanotubes. A recipe that included ethylene as a carbon precursor, and which was run at 800° C. resulted in a moderate yield of carbon nanotubes. A recipe that included both ethylene and methane as carbon precursors and which was run at 900° C. results in a higher yield of carbon nanotubes. Nanotube growth was initiated only at the location of the Co catalyst particles. The resulting direction and length of each nanotube was random, and the probability that a certain number of tubes connects source and drain electrodes was obtained by Poisson statistics.

Step 6, thin silicon nitride layer. After the nanotubes were grown, a thin layer of silicon nitride was conformally deposited on top of them using a Plasma Enhanced Chemical Vapor Deposition (PECVD) process. This layer was preferably about 10 nm in thickness. The function of the thin nitride layer was to protect the carbon nanotubes from wet chromium etchant during Step 10. Strong oxiding agent (cerric ammonium nitrate) in Cr-14 Chromium Etchant damages carbon nanotubes if it directly contacts them for an extended period of time. Thus during the chrome etch, nanotubes were separated from the channel by the thin nitride layer. That thin layer was later removed (Step 12) using an etchant that did not damage carbon nanotubes. Covering nanotubes with nitride provided some protection from the possibility of static charge induced damage during the remaining fabrication steps.

Because nitride was deposited directly onto bare nanotubes, the deposition parameters were chosen so as not to damage the tubes. PECVD silicon nitride was selected instead of PECVD silicon oxide, owing to the well known observation that nanotubes are quickly etched in an RF oxygen plasma. During the course of process development it was observed that low frequency RF plasma in direct contact with bare nanotubes induced damage to the tubes (in the form of reduced conductance). This is a result of physical ion bombardment. To protect the nanotubes from low frequency nitride deposition, a short high frequency nitride deposition was first performed. This covered the nanotubes and protected them from physical ion bombardment. This is described in more detail below in the section entitled "Effect of nitride deposition on carbon nanotube electrical properties."

Step 7, microchannel/nanochannel sacrificial chromium layer. Using photolithography, e-beam evaporation and lift-off, a layer of chromium was deposited on the wafer. The chromium pattern defined the shape and thickness of the desired micro-channels and nanochannels. The final channel height was preferably no less than the thickness of the chromium sacrificial layer (although it could be more depending on the wet etch Step 11). Chromium was chosen as the sacrificial material owing to the high selectivity between the wet etch rates of chromium versus silicon nitride and fused silica in CR-14 Chrome Etchant.

Step 8, thick silicon nitride layer. After Cr deposition, the sacrificial material and the carbon nanotubes were covered by a thick layer (~2 µm) of low stress nitride. This nitride layer later became the "ceiling" of the nanofluidic device. Its mechanical properties were therefore an important characteristic for maintaining structural integrity of the channel. A nitride film with low tensile stress and thickness of ~2 µm was chosen to prevent cracking or collapse of the nitride after sacrificial layer removal. Films with higher tensile stress were found to crack, and thinner films were found to collapse. Films with compressive stress properties were found to bow. Testing and characterization of these effects is shown in the section below entitled "Carbon nanotube growth."

Step 9, access hole layer #1 (for wet etch of sacrificial material). Access holes through the thick silicon nitride layer were created using a combination of photolithography and dry chemical etching. The access holes ran along the length of the microchannel and nanochannel regions. During this step, in addition to the access holes for wet chemical etching, holes above the contact pads were created, enabling access of probe needles to the source and drain contact pads.

Step 10, wet etch of sacrificial material. The sacrificial chromium layer was removed using Cyantek CR-14 Chromium Etchant. With access holes spaced approximately 50 µm apart along the length of the channel, and a lateral etch rate of 10 µm/hr., all of the chromium was removed in about 3 hours. Generally the etch was allowed to run roughly twice as long (5-6 hours). In Cr-14 etchant, the selectivity between chromium and silicon nitride was very high, as was the selectivity between chromium and fused silica.

Step 11, wet etch of thin silicon nitride layer. After removal of the chromium layer, a system of channels was created with a depth equal to that of the original chromium layer. This allowed for quick delivery of the next wet etchant (MIF 312). Trimethylammonium hydroxide (TMAH) was present at 5% of total volume in MIF 312. When heated, TMAH etched low stress GSI PECVD silicon nitride at a rate of about 2 nm/min. This allowed for upwards etching of the silicon nitride, to the point at which carbon nanotubes were released from within the nitride ceiling. The chip was submerged in MIF 312 at 70° C. for 15 min to 45 min, depending on the thickness of the previously deposited protective nitride layer.

Step 12, thin silicon nitride layer #2 (for enclosing access holes). After the second wet etch step, chips were dried and electrical conductance of nanotubes tested. The access holes used in the wet chemical etch were sealed for channels to be complete. Low stress silicon nitride was again deposited using PECVD. The final silicon nitride film was of medium thickness (several hundred nm) to ensure that all of the access holes were completely sealed.

Step 13, access hole layer #2 (for allowing access of probe needles to source and drain contact pads). Having deposited a final layer of silicon nitride, the contact pads was again uncovered. This was done using a combination of photolithography and reactive ion etching.

Step 14, macroscopic reservoir attachment. In the chip's near final state, the contact pads were exposed, but the nanochannels and microchannels were completely sealed. Entrances at the six microchannel ends were created by lightly scratching the nitride with a diamond scribe. Macroscopic reservoirs were then aligned to the channel entrances by eye and glued to the chip using RTV sealant. After the glue set, the devices were ready to be filled and used in experiments.

In-Depth Characterization of Select Processes in Fabrication Procedure

Etch Characterization

Wet etch rates. To describe the characteristics of the chromium sacrificial layer removal step, first is described the etching of another material layer, amorphous silicon, that had been tested as a candidate for the sacrificial layer before chromium was settled on. As known in the art, there exists excellent selectivity for amorphous silicon and silicon nitride in TMAH. For a-Si and LPCVD nitride, selectivities as high as 20000:1 have been reported in 5% TMAH. This combination of materials was therefore a good candidate for the sacrificial process. After testing the etch rates of a-Si and GSI PECVD nitride, it was found that the selectivities were much lower than expected. Namely, they were approximately 50:1.

Table 1 is a compilation of measured etch rates and values found in the literature. Column 1 data is from Williams (2003), Journal of Microelectromechanical Systems, vol. 12, no. 6, December 2003. Column 3 data is from Merlos (1993) Sensors and Actuators A, 37-38 737-743

TABLE 1

|  | Cr-14 at 25° C. | | MF-312 (5% TMAH) at 70° C. | |
| --- | --- | --- | --- | --- |
|  | Literature | Measured | Literature | Measured |
| Silicon | 0.0 nm/min | 0.0 nm/min | 100 nm/min | 100 nm/min |
| Silicon Nitride (High Stress) | — | 0.0 nm/min | 0.005 nm/min | 1.6 nm/min |
| Silicon Nitride (Low Stress) | — | 0.0 nm/min | — | 2.1 nm/min |
| Silicon Dioxide | 0.0 nm/min | 0.0 nm/min | 0.02 nm/min | 0.5 nm/min |
| Chromium | 93 nm/min | 23 nm/min | — | — |
| Fused Silica | 0.0 nm/min | — | — | — |

Table 1 gives etch rates for a variety of possible wall and sacrificial materials in Cr-14 and MF-312 etchants. For each etchant and material there is either a value for etch rate determined experimentally, reported in the literature, or both. The measured selectivity between chromium and silicon nitride is infinite within error. The measured selectivity between amorphous silicon and silicon nitride in 5% TMAH is between 48:1 and 62:1, depending on whether a high stress or low stress recipe was used for the nitride. This differs from the value reported in the literature of 20000:1 for amorphous silicon and high stress nitride. The discrepancy is attributed to the fact that the high stress nitride investigated in the literature was LPCVD deposited nitride, while that investigated in the present example was PECVD deposited nitride.

The poor selectivity of a-Si and GSI PECVD nitride resulted in channels which were tapered and much deeper near the access hole entrances. This observation is illustrated in FIG. 15 and optical images of the channels after the wet etch step are shown in FIG. 16. Chromium wet etch selectivities were later measured as well. During various stages of the etch, the distance between the nanochannel entrance and the chrome in a partially etched channel could be measured by optical microscopy. Examples of such images are shown in FIG. 17. The observed rate was approximately 10 μm/hr or 27 nm/min. Within the error of measurement, there was infinite selectivity between chromium and silicon nitride in Cr-14 etchant.

FIG. 15 is a schematic diagram illustrating the importance of selectivity in sacrificial Layer removal. Left Column) Channel depth is determined by sacrificial layer thickness only. Right Column) Channel depth is determined by sacrificial layer thickness plus amount of capping material etched.

FIG. 16 shows images of a-Si/Nitride based channels after partial removal of a-Si with TMAH etch. Access holes are the dark rectangles. The light gray areas are places where the a-Si sacrificial layer was not yet etched away. The gaps between the fused silica surface and nitride ceiling varied in depth owing to upward etching of the nitride as the a-Si was etched inward.

FIG. 17 shows images of Cr/Nitride based channels after partial removal of Cr with Cr-14 Chromium Etchant. FIGS. 17A-C are images of the microchannel region before etch, after 25 min, and after 3 hours. FIGS. 17D-F are close ups of the nanochannel region before etch, after 25 min, and after 3 hours. Note that because all portions of the etched channel were the same depth, there were not regions of etched channel with different colors as was the case with the channels shown in FIG. 16.

Dry Etch Rates

Using a combination of reactive ion etching, profilometry, and interferometry, dry etch rates were measured for silicon nitride. Low Stress Nitride in $CHF_3/O_2$, Oxford 80#1 Nitride Recipe was 98 nm/min.

Nitride Deposition

Silicon nitride films deposited by PECVD at temperatures lower than 400° C. are typically observed to be amorphous, and their structural, electrical and optical properties are strongly dependent on deposition parameters (Lin, K. C. and S. C. Lee, The structural and optical-properties of A-SINXH prepared by plasma-enhanced chemical-vapor deposition. Journal of Applied Physics, 1992. 72(11): p. 5474-5482; Parsons, G. N., J. H. Souk, and J. Batey, Low hydrogen content stoichiometric silicon-nitride films deposited by plasma-enhanced chemical vapor-deposition. Journal of Applied Physics, 1991. 70(3): p. 1553-1560). The electrical detector has characteristics wherein a nitride film that has low autofluorescence, is electrically insulating, and is structurally stable in the form of a nanochannel ceiling or wall is preferred.

In testing various nitride deposition parameters, it was observed that the first two conditions were met to satisfaction over the entire range of parameters tested. It is the mechanical properties of the film that varied by the greatest amount. Only a narrow range of deposition parameters resulted in a film with satisfactory mechanical properties.

For reasons that are discussed in detail later in this section, it was preferable that the deposited film be one of low tensile stress. Several deposition parameters are known to affect the residual stress of the material including deposition temperature (Walmsley, B. A., et al., Effects of deposition temperature on the mechanical and physical properties of silicon nitride thin films. Journal of Applied Physics, 2005. 98(4): p. 6; Martyniuk, M., et al., Stress in low-temperature plasma enhanced chemical vapour deposited silicon nitride thin films. Smart Materials and Structures, 2006, 15 S29-S38, doi: 10.1088/0964-1726/15/1/006), ratio of precursor gases leading to variations in stoichiometric content (Pearce, C. W., et al., Characteristics of silicon-nitride deposited by plasma-enhanced chemical vapor-deposition using a dual frequency radiofrequency source. Journal of Applied Physics, 1992. 71(4): p. 1838-1841), and the frequency or combination of frequencies used to generate the plasma during deposition (Pearce, C. W., et al., Characteristics of silicon-nitride deposited by plasma-enhanced chemical vapor-deposition using a dual frequency radiofrequency source. Journal of Applied Physics, 1992. 71(4): p. 1838-1841; Cianci, E., et al., Dual frequency PECVD silicon nitride for fabrication of CMUTs' membranes. Sensors and Actuators a-Physical, 2006. 127(1): p. 80-87).

While deposition temperature can be used in part to tune stress, and is typically a free parameter in nitride deposition processes, the present process was preferably run at a deposition temperature of 300° C. Other suitable temperatures can be readily determined by the skilled artisan. CNTs were already present on the chips before nitride deposition, and if the wafers were heated to temperatures much higher than 300° C. during loading into the PECVD machine, oxygen in the chamber could cause the CNTs to burn. Furthermore, it is known in the art that increasing deposition temperature causes an increases residual tensile stress. As will be shown later in this section, the tensile stress was decreased, as compared with the nominal stress value for deposited films, using standard protocols known in the art. Temperatures below 300° C. were not used because it has been reported that as deposition temperature is reduced toward 200° C. the observed film quality becomes poor because film porosity increases (Walmsley, B. A., et al., Effects of deposition temperature on the mechanical and physical properties of silicon nitride thin films. Journal of Applied Physics, 2005. 98(4): p. 6).

Having established 300° C. as the preferred deposition temperature, the frequency characteristics of the plasma were varied to tune film stress. As reported by Pearce et al. (Pearce, C. W., et al., Characteristics of silicon-nitride deposited by plasma-enhanced chemical vapor-deposition using a dual frequency radiofrequency source. Journal of Applied Physics, 1992. 71(4): p. 1838-1841), the use of two radio frequency generators, one at 13.56 MHz and one at several hundred kHz, can be used to vary intrinsic film stress by altering the amount of power supplied by each source. It was observed that the low frequency excitation favors the formation of N—H bonds, and the relative amount of N—H bonds and Si—H bonds were shown to affect stress. As the percentage of low frequency power used was increased from 50% to 70%, the film stress changed smoothly from 50 MPa tensile to 150 MPa compressive.

The GSI PECVD machine used had two radio frequency sources, one at 13.56 MHz, and another at 300 kHz, with maximum output powers of 1000 W and 200 W respectively.

A deposition parameter of 300° C. was preferred to a higher temperature. A fused silica substrate was preferred to a silicon substrate. These differences affect film stress through a mismatch in thermal expansion characteristics. Low temperature deposition reduces the effects of mismatch. The reported coefficients of linear thermal expansion for silicon, fused silica, and silicon nitride at 327° C. are 3.7, 0.5, and 2.8 $10^{-6}$ $K^{-1}$ respectively. A temperature transition from 300° C. to 20° C. resulted in a compression of 14%, 9.3% and 2.4% for each of the three materials on their own (Thermal Expansion, Nonmetallic Solids. Thermophyisical Properties of Matter, the TPRC Data Series. Vol. 13. 1977, IFI Plenum: NY, N.Y.). For stacked materials, it was assumed that the substrate wafer dominated the thermal compression process and the thin film was forced to comply.

When a thin film of silicon nitride deposited on a silicon wafer at 300° C. cooled to room temperature, it was forced to compress to 14% of its original length in one dimension. This was greater than the 9.3% linear compression it would experience if it were not fixed to the silicon surface. This thermal contraction mismatch caused the film to have a higher compressive stress than it would have had on its own.

For a thin film of silicon nitride deposited on a fused silica wafer, the effect was reversed. The fused silica substrate wafer compressed by only 2.4% in one direction, while the nitride, on its own, would have compressed by 9.3% upon cooling. Because the nitride was not permitted to fully relax, the film had a higher tensile stress than it would have if it had not been fixed to the fused silica.

Thus the effect of cooling from 300° C. to 25° C. had the opposite effect on stress for thin nitride films deposited on silicon as compared to films deposited on fused silica.

The effect of various types of stress on the micro- and nanochannel ceilings was next considered. The channel ceilings were modeled as doubly clamped beams. The channel length was much greater than the channel width and depth in all cases, therefore the dimension along the direction of the channel axis were ignored, and only the cross section was considered. Depending on the stress of the nitride film, the beam experienced forces that could cause it to deform in a number of different ways. For example, high compressive stress lead to buckling in either the up or down vertical directions, as is illustrated in FIGS. 18A and 19A. At the opposite extreme, a high tensile stress film inevitably lead to cracking of the ceiling at many points along the channel (data not shown). A low tensile stress film represented the ideal case, but if the stress was too small in magnitude, the beam could not resist deforming under the load of dispersion forces and/or the capillary forces acting on the walls during any number of fabrication steps in which the channel were dried.

To determine the appropriate stress, the regime of high to low tensile stress was investigated. A condition was sought under which both cracking and collapse is avoided. Under a uniform load, such as is induced by dispersion forces between a ceiling and a floor, the beam experiences a maximum downward deflection, z, given by, $$z = \frac{L^3 \cdot \lambda}{E \cdot h^3}$$

where L is the length of the beam (in our case the width of the nanochannel), λ is the load, E is the Young's modulus (which is a function of the stress), and h is the height of the thin film (beam thickness). Using this equation as a guide, the maximum deflection is more strongly dependent on the film thickness and length of channel spanned, than it is on the stress. These are two additional parameters that are preferably varied to create channel ceilings that do not crack under their own stress, yet also do not collapse.

FIGS. 18A-B show deformation of channel ceiling structure. FIG. 18A shows the effect of stress on deformation. FIG. 18B shows the effect of nitride thickness and width of channel spanned on deformation under a uniform load.

In FIGS. 18B, 19B and 19C, the effects of beam length (channel width) and thickness is shown on probability of collapse given a constant internal stress. Previous to these tests, the deposition parameters were determined that would result in a low enough tensile stress such that cracking did not occur. In the images of FIG. 19B and FIG. 19C, the same combination of frequencies is used during deposition.

In one embodiment, preferable deposition parameters were: high frequency power 19% (190 W), low frequency power 81% (162 W), deposition duration 20 min(=2 um thick film), maximum channel width 16 μm. This results in a negligibly small probability of cracking or collapsing for channels created with a sacrificial Cr layer as thin as 10 nm in thickness. A sub 10 nm Cr layer can also be used. For nitride films with thickness of less than 1000 nm, no degree of stress could be found which prevented both channel collapse and film cracking.

FIGS. 19A-C show various micrographs illustrating the effects of film stress, thickness and channel width on channel integrity. FIG. 19A shows a 40 μm wide channel with no support columns. The film was deposited using a pure low frequency deposition process with the IPE CVD machine, and was under a high degree of compressive stress. After removal of the Cr, the ceiling buckled both upwards and downwards. The left hand micrograph is an optical image in which variation in shades of gray (originally color in the optical image) and intensity results from variations in cavity height. The right hand image is an SEM micrograph of the same channel. The black line over the left image represents the location of a profilometry scan in which the maximum vertical deflection of the ceiling was found to be 2 μm.

FIG. 19B shows the effect of channel width on collapse probability can be seen by looking at a single image of a channel with various amounts of space between the walls and the support columns. The light areas represent an air gap between the floor and ceiling of 25 nm. The darker areas represent nitride in direct contact with the fused silica substrate below it. The light gray area to the far right represents Cr (25 nm thick) which had not yet been removed before the wet etch was stopped.

The three channels shown in 19C illustrate the effect of nitride thickness on probability of collapse. The evenly gray shaded channel for the 1650 nm thick film was the only one that did not collapse. Note that in all cases, profile scans were used to verify the notion that certain portions of the ceiling had or had not collapsed.

Carbon Nanotube Growth

Catalyst deposition. Cobalt catalyst particles were deposited in photolithographically defined areas, as described in this example in Section 6.2.3 in the subsection entitled "Device Fabrication Process Overview." Cobalt was eventually chosen over iron for the catalyst owing to processing restrictions in the GSI PECVD machine. However Fe catalyst was used in the initial stages of the project.

Based on observations of several thousand SEM images obtained, the carbon nanotubes appeared, on average, shorter and less dense when grown using Co catalyst than when grown using Fe catalysts. Both Co catalyst growth and Fe catalyst growth result in sufficient densities of nanotubes with lengths greater the several micrometers.

Nanotube Device Yield

Using the device design and procedure set forth in the Sections 6.1 and 6.2 (Examples 1 and 2), it has been observed that from 0 to 10 nanotubes bridge each source and drain electrode. The actual number of nanotubes per electrode pair was random and was governed by Poisson statistics. The probability mass function for rare occurrence statistics is $$f(k, \lambda) = \frac{\lambda^k \exp(-\lambda)}{k!}$$

where, in the present example, f is the probability that a source drain electrode pair has k connecting them, if the mean number of nanotubes connecting the source drain pairs is λ. If, for example, the mean number of connecting nanotubes per electrode pair is λ=1, then the probability that an given electrode pair has exactly k=1 connected nanotubes is f=$e^{-1}$≈0.36, the probability that there are no connected nanotubes for a given electrode pair is also f=$e^{-1}$≈0.36, and the probability that there is more than one connected nanotube for a given electrode pair is also f=$e^{-1}$≈0.38.

When running the ethylene growth process at 800° C., only about 10% of the electrode pairs had no connecting nanotube, given the device geometry and catalyst particles. When running the same process at 750° C., the percentage of electrode pairs showing no current above the noise was closer to 90%. These growth runs were performed with chips from the same wafer (i.e., same catalyst processing) and within a three week period (so nanotube furnace temperature probably had not drifted much).

The temperature adjustment offered some degree of control over nanotube yield in the above-described process. Other factors that also affect the number of connect nanotubes per device are catalyst and source drain pad size, source-drain separation distance, catalyst thickness, catalyst support ($Al_2O_3$ or fused silica), height of T-shaped Pt pad and height of Cr sacrificial layer. These parameters and others have been adjusted at one time or another throughout the process development, and any of them could be explored in a more systematic way.

Photolithography

Micro (μ) DFAS Alignment Marks

Figure 20:
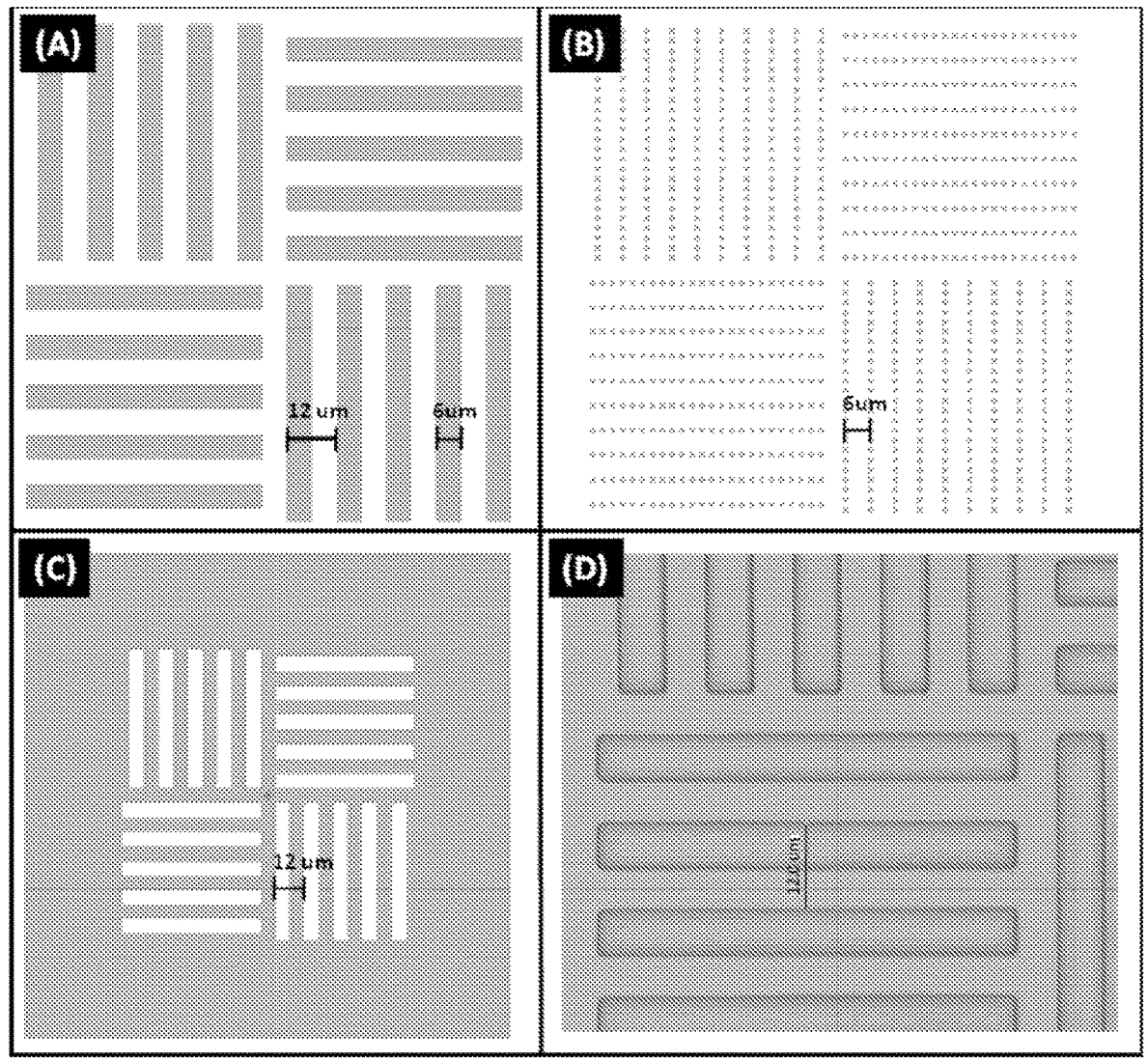

In any multilayer photolithography based process, the interlayer must be accurately aligned. In the method described in this example, alignment was achieved through the use of a system specific to the Autostep machine, the micro Dark Field Alignment System (microDFAS or μDFAS). To utilize this system, a patterned layer of regularly spaced marks are etched directly into the wafer. These are then used to align the wafer with the Autostep reticle in each of the subsequent alignment and exposure steps. There are several patterns available, each of which can be recognized by the microDFAS system. Choosing a pattern appropriate to our substrate and resist is crucial for good alignment. In FIGS. 20A-D, diagrams of three possible microDFAS patterns are shown (FIG. 20A-C), as is a bright field image of one of those patterns (FIG. 20D).

Figure 21:
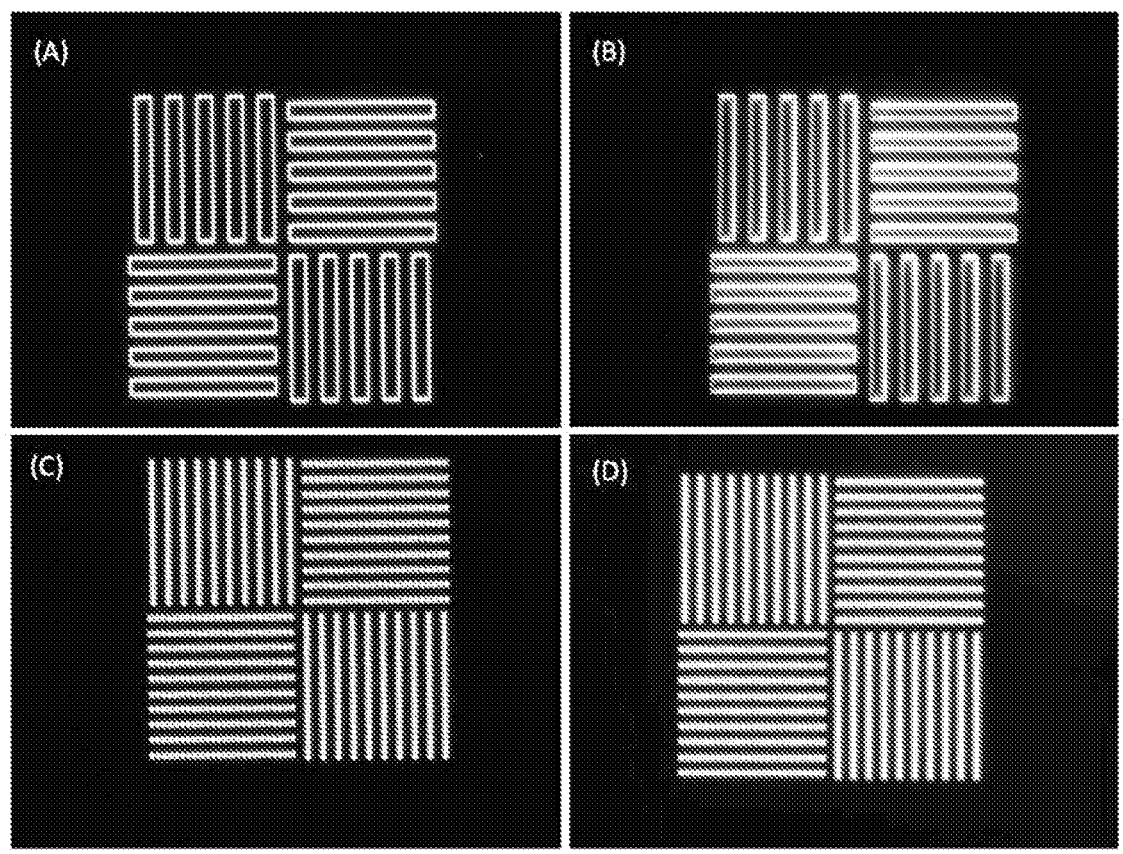

Dark field images of these marks appear quite different. In dark field microscopy, the edges of the etched features appear brightest, as can be seen by comparing FIG. 20D with FIG. 21A. The microDFAS system uses the long edges of each rectangle when aligning a wafer. In FIG. 21A the edges of the rectangle appear very sharp. If the alignment marks looks sharp, then the machine will have an easier job performing an accurate alignment. Typically, if the substrate wafer is silicon, coating the features with a layer of photoresist will not affect the dark field alignment pattern. In the electrical detector, the substrate wafer is fused silica, which has an index of refraction similar to that of photoresist. Thus when photoresist non-uniformly coats the etched rectangles, edges in the dark field image appear to be smoothed out instead of sharp. The apparent edge is blurred and shifted toward middle of each the rectangle. This results in a poor alignment mark signal and inconsistent alignment by the microDFAS system.

As an alternative to the "rectangle edge" pattern, a series of lines can be defined by etching small circles where the rectangle "edges" used to be. Thus the photoresist cannot severely distort the dark field image, as is apparent FIGS. 21C-D. Employing this pattern resulted in much better alignment by the microDFAS system.

FIGS. 20A-D shows variations of the micro DFAS mark pattern available for use with the Autostep mask aligner. FIG. 20A is a snapshot of a CAD image for a "solid rectangle" micro DFAS mark in positive tone. Shaded areas were exposed in the photolith step and were etched into the substrate wafer. The width of each rectangle was 6 μm and the half pitch is also 6 μm.

FIG. 20B is a snapshot of CAD image for a "segmented line" microDFAS mark in positive tone. The small shaded squares composing each segmented line are separated by approximately 2 μm. The segmented lines are spaced by 6 μm.

FIG. 20C is a snapshot of a CAD image for a "solid rectangle" micro DFAS mark in negative tone. Shaded areas were exposed in the photolith step and were etched into the substrate wafer. Thus the rectangles were un-etched and were raised off the surface. The negative tone version of the "segmented line" pattern is not shown.

FIG. 20D is a bright field image of a micro DFAS mark etched into a fused silica wafer. This mark is the "solid rectangle" pattern shown in FIG. 21A, where the rectangles was etched greater than 2 μm into the wafer.

FIG. 21A is a dark field image of μDFAS mark pattern 1 etched into fused silica. FIG. 21B is a dark field image of μDFAS mark pattern 1 under SPR 955 0.9 photoresist. Owing to uneven filling of the rectangular etch mark trenches, the line edges of the etch marks become blurred the dark field. FIG. 21C is a dark field image of μDFAS mark pattern 2 etched into fused silica. FIG. 21D is a dark field image of μDFAS mark pattern 2 under SPR 955 0.9 photoresist. Owing to uneven filling of the rectangular etch mark holes, the line edges of the etch marks become blurred the dark field. In the case of holes, however, this does not matter, since the entire hole is viewed as one "edge" by the μDFAS system.

LOR Thickness and Minimum Feature Separation

Several of the "major steps" in the process used a combination of photolithography e-beam evaporation and lift-off. A method was used in which a bi-layer resist, or more specifically, a lift-off resist (LOR), was used in combination with a standard photoresist layer. This method also produced sharp metal edge profiles, but did not require a lengthy image reversal step, and for certain patterns permitted more straightforward mask design.

Several versions of LOR are available, each having a different viscosity and producing a different LOR film thickness when spun onto a wafer. For most metal lift off applications, LOR 5A or 10A is preferable, which results in film thicknesses in the range of 400-600 nm and 900-1100 nm respectively. Typically LOR5A was the least viscous lift off resist that was tested. If, however, there existed features on a pattern that were separated by less than a micrometer, then a thinner LOR film might be required.

Figure 22:
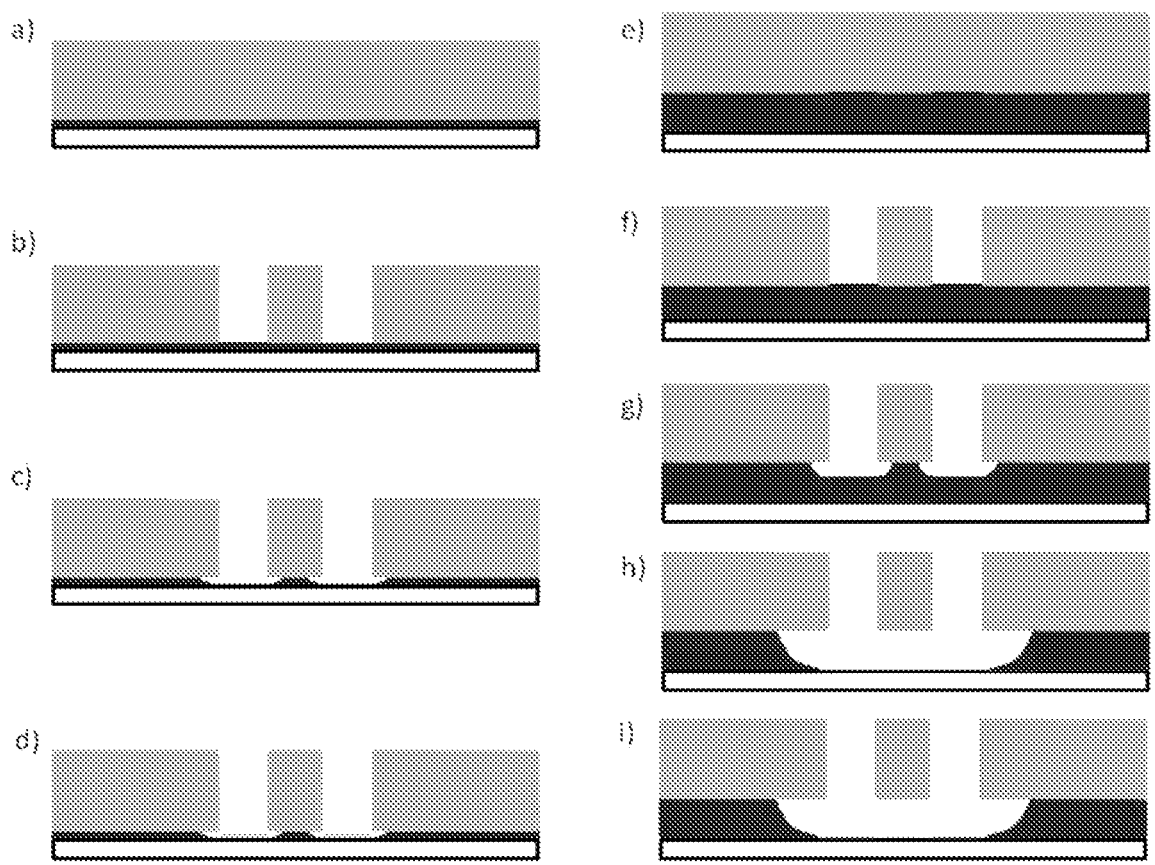

During development, after rapid dissolution of the exposed portions of photoresist, the LOR directly underneath that photoresist was etched isotropically, immediately creating an undercut. It was required however, to continue to etch the LOR until it had completely cleared in the patterned spaces where metal was to be deposited. If the LOR was 500 nm in thickness then the minimum lateral undercut was 500 nm. For two features closer than 1 µm apart, all of the LOR between them was etched. In the most desirable cases, this resulted in a suspended bridge of photoresist that could still be used for lift off. Such a scenario is illustrated in FIG. 22B. More often however, that bridge of photoresist either tore away or collapsed, and the pattern had to be reshot.

FIGS. 22A-I shows photoresist and Lift-off Resist (LOR) profiles for two different thicknesses of LOR. The left column shows the profile of 100 nm thick LOR during various stages. In FIG. 22A, a fused silica wafer was prepared with 100 nm LOR (bottom layer) and 900 nm photoresist (top layer). In FIG. 22B, after exposure the wafer was placed into 300 MIF developer. Initially the exposed pattern in photoresist dissolved. FIG. 22C shows that, over the course of the development process, LOR was isotropically etched at a much slower rate than the exposed photoresist, but at a faster rate that the unexposed photoresist. In FIG. 22D, a thin layer of metal was deposited by e-beam evaporation. FIG. 22E, a fused silica wafer was prepared with 500 nm LOR (bottom layer) and 900 nm photoresist (top layer).

In FIG. 22F-I, the photoresist was developed and the LOR was isotropically etched. If separation between two features was 1000 nm or less, then the LOR under the resist in between those features would clear completely. Thus it was possible for the resist to collapse or tear off, affecting the pattern of evaporated metal.

Thus, a LOR layer with a thickness on the order of 100 nm was used, as depicted in FIG. 22a. This was the case for the Pt electrode layer, since the gap between source and drain electrodes was roughly 1 µm.

Effect of Nitride Deposition on Carbon Nanotube Electrical Properties

Carbon nanotubes burn when heated in the presence of oxygen. They are similarly destroyed by oxygen plasma. Previous to the development of the fabrication process described in this example, it had been reported that CNTs do not burn during silicon nitride using thermal CVD (Holt, J. K., et al., Fabrication of a carbon nanotube-embedded silicon nitride membrane for studies of nanometer-scale mass transport. Nano Letters, 2004. 4: p. 2245-2250; Mizutani, T., et al., Effects of fabrication process on current-voltage characteristics of carbon nanotube field effect transistors. Japanese Journal of Applied Physics Part 1-Regular Papers Short Notes & Review Papers, 2005. 44(4A): p. 1599-1602). Furthermore, one group reported that CNTs can also survive PECVD nitride deposition, while another group reported that PECVD immediately destroyed the tubes, and thermal CVD was used instead.

While we are not able to use the thermal CVD furnaces in the CNF (material restrictions), we are permitted to use the GSI PECVD, as mentioned above. It is partly for this reason that silicon nitride was chosen as the capping material. Capping material is the material deposited on top of the sacrificial chromium layer. When the chrome is later etched away, this capping material becomes the ceiling of the nanochannels or microchannels.

Through process development, reports known in the art were verified that CNTs can survive silicon nitride deposition by PECVD, but only given certain process restrictions. When CNT survival has been observed, only high frequency RF generated plasma was used during nitride deposition. The present process, however, requires low frequency RF plasma to create low tensile stress nitride films. in order for the nitride film (capping layer) to be mechanically stable (not crack or collapse) low frequency RF plasma must be used for the majority of the time during nitride deposition.

Only low frequency RF plasma nitride deposition will produce nitride with the appropriate mechanical properties. However, it was found that low frequency RF plasma destroys nanotubes. Therefore, a brief high frequency RF deposition was employed to first cover the nanotubes with a thin layer of nitride without destroying them. High frequency RF plasma did not affect the nanotubes. Once they were protected by a small amount of nitride, a low frequency RF plasma could be used to deposit the remainder of the nitride film. Thus, the nitride capping layer had the desired mechanical properties, but the nanotubes were not damaged. For purely high frequency RF PECVD nitride deposition, individual carbon nanotubes appeared to both increase and decrease their conductance, while the average conductance over many nanotubes did not change significantly. This was a result of interactions between nanotube surfaces and charges associated with the deposited silicon nitride, the removal of water vapor, or the removal of oxygen from the CNT surface (Mizutani, T., et al., Effects of fabrication process on current-voltage characteristics of carbon nanotube field effect transistors. Japanese Journal of Applied Physics Part 1-Regular Papers Short Notes & Review Papers, 2005. 44(4A): p. 1599-1602; Kojima, A., et al., Air stable n-type top gate carbon nanotube filed effect transistors with silicon nitride insulator deposited by thermal chemical vapor deposition. Japanese Journal of Applied Physics Part 2-Letters & Express Letters, 2005. 44(8-11): p. L328-L330; Chen, B. H., et al., A carbon nanotube field effect transistor with tunable conduction-type by electrostatic effects. Solid-State Electronics, 2006. 50(7-8): p. 1341-1348). As the power of the low frequency RF was increased, both the individual and average nanotube conductances tended to decrease dramatically. Furthermore, this decrease in conductance only occurred as a result of the first few seconds of nitride deposition. After a short deposition, any subsequent nitride deposition did not result in a change of nanotube conductance, regardless of the duration or frequencies used.

The mechanism of nanotube destruction is physical bombardment of ions accelerated into the substrate surface by the low frequency electromagnetic field. Once nanotubes are covered by an initial layer of silicon nitride, they appear to be protected from further damage. Thus silicon nitride was deposited onto the carbon nanotubes as follows.

First, a silicon nitride film was deposited using a high frequency plasma for a short duration of time. 10 nm of nitride was deposited over 5 sec. Following deposition of this thin high stress film, a thick layer of low stress nitride was deposited using a dual frequency plasma. The 20 min deposition resulted in a low stress film that was 2 µm in thickness and that had the mechanical properties required for the micro and nanochannel wall/ceiling material.

6.3 Example 3: Detailed Protocol for Fabrication of Device Comprising a Nanofluidic Channel with an Integrated Carbon Nanotube The following is an example of a fabrication protocol that has been carried out based on the methods for fabricating the electrical detector set forth in Section 6.2 (Example 2).

Step 1: Fabrication of Alignment Layer
1. Pre-Processing:
   a. Obtain three, 100 mm diameter, 170 µm thick, fused silica wafers. (Mark Optics) Wafers should have a scratch dig parameter of 40/20 or lower, and an RMS surface roughness of <20 Å.
   b. Scribe Wafer Numbers onto back of wafers using a diamond scribe.
   c. Clean wafers in an automated spin-rinse-dry machine.
2. Photoresist Preparation:
   a. p-20 primer; spin at 3000 RPM, 5000 R/S, 45 sec
   b. SPR 220 3.0 Photoresist; spin at 3000 RPM, 5000 R/S, 45 sec
   c. Bake on hotplate at 115° C. for 2 min.
3. Photolithography in Autostep Mask Aligner
   a. Load the desired photolithography mask into the mask aligner.
   b. Expose for 0.3 sec
   c. Post exposure bake at 115° C. for 2 min
   d. Develop in 300 MIF for 90 sec via hand dip and agitation.
4. Reactive Ion Etch (Oxford 80#1 or Oxford 80#2)
   a. Descum wafers using 20 sec. O2 plasma at 150 W
   b. $CHF_3/O_2$ Oxide Recipe; etch for either 59 min (Oxford 80#)1 or 1 hr 20 min (Oxford 80#2)
   c. Fluorinated Polymer Removal using 40 sec. O2 plasma at 150 W
5. Resist Strip. Clean wafers using hot resist strip bath for ~2 hrs, followed by spin-rinse-dry.
Step 2: Pt/Ti Electrode Layer
1. Photoresist Preparation:
   a. p-20 primer; spin at 4000 RPM, 10,000 R/S, 45 sec
   b. LOR 1A (lift off resist); spin at 4000 RPM, 10,000 R/S, 45 sec
   c. Bake on hotplate at 180° C. for 5 min.
   d. SPR 955 0.9 Photoresist; spin at 4000 RPM, 5000 R/S, 45 sec
   e. Bake on hotplate at 100° C. for 2 min.
2. Photolithography
   a. Load desired mask in mask aligner.
   b. Expose for 0.14 sec.
   c. Post exposure bake at 115° C. for 2 min
   d. Develop in 300 MIF for 60 sec. via hand dip and agitation.
3. Descum (Branson): run standard photoresist descum for 1 min.
4. E-beam Evaporation of Ti/Pt (Even Hour or Odd Hour Evaporator)
   a. load samples, titanium slug, platinum slug, and new quartz crystal monitor QCM
   b. evaporate 4 nm titanium at rate of 0.2-0.4 Å/s
   c. evaporate 30 nm platinum at rate of 0.2-0.4 Å/s
5. Ti/Pt Lift-Off
   a. Place wafers in '1165' microposit remover and let sit overnight
   b. (next day) Sonicate for 20-30 min., transfer wafers to IPA, remove from IPA and dry with Nitrogen.
Step 3: Aluminum Oxide Supported Cobalt Catalyst Layer
1. Photoresist Preparation:
   a. p-20 primer; spin at 4000 RPM, 10,000 R/S, 45 sec
   b. LOR 1A (lift off resist); spin at 4000 RPM, 10,000 R/S, 45 sec
   c. Bake on hotplate at 180° C. for 5 min.
   d. SPR 955 0.9 Photoresist; spin at 4000 RPM, 5000 R/S, 45 sec
   e. Bake on hotplate at 100° C. for 2 min.
2. Photolithography
   a. Load desired mask(s) in mask aligner.
   b. Expose for 0.14 sec.
   c. Post exposure bake at 115° C. for 2 min
   d. Develop in 300 MIF for 75 sec via hand dip and agitation.
3. Descum (Branson): run standard photoresist descum for 1 min.
   a. E-beam Evaporation of $Al_2O_3$ supported Cobalt Catalysis
   b. load samples, titanium slug, aluminum oxide cobalt slug, and new QCM.
   c. evaporate 0.3 nm titanium at rate of 0.1 Å/s
   d. evaporate 15 nm aluminum oxide at rate of 0.2-0.4 Å/s
   e. evaporate 0.25 nm cobalt at rate of 0.1 Å/s
4. Supported Catalyst Lift-Off
   a. Place wafers in '1165' microposit remover and let sit overnight
   b. (next day) Sonicate for 20-30 min., transfer wafers to IPA, remove from IPA and dry with Nitrogen.
Step 4: Wafer Dicing
1. Photoresist Preparation (to protect features from dicing saw debris):
   a. SPR 220 7.0 Photoresist; spin at 2000 RPM, 1000 R/S, 45 sec
   b. Bake on hotplate at 115° C. for 2 min.
2. Dicing (Wafer Saw)
   a. Dice wafers into 20 mm×20 mm squares
   b. Peel tape from chips. Scribe labels onto chips.
3. Photoresist Strip
   a. Place chips in '1165' microposit remover and let sit for several hours or more.
   b. Sonicate for 20-30 min., transfer wafers to IPA, remove from IPA and dry with Nitrogen.
Step 5: Carbon Nanotube Growth
1. CVD growth of single walled carbon nanotubes:
   a. Clean furnace tube by baking each segment at 900° C. for 10 min. Cool to 500° C.
   b. Insert 3 Chips into the tube at the center of the furnace. Calcine chips by baking in atmosphere (tube ends open) for 30 min at 500° C. Cool to room temp (furnace thermometer<100° C.).
   c. Attach hoses to ends of tube and pre-flow process gases at room temp to purge system of oxygen. Using the electronic gas flow controllers, flow the following for ~10 min:
      i. 0.8 SLM Ar
      ii. 0.2 SLM $H_2$
      iii. 5.5 SCCM $C_2H_4$
   d. Switch off ethylene, and continue flowing argon and hydrogen. Raise temperature to 700° C. and hold this for 30 min. This serves to reduce the catalysts.
   e. Raise temperature to 800° C., wait 3 min.
   f. Add ethylene while maintaining hydrogen and argon. Hold this for 10 min. This is the CNT growth stage.
   g. Subtract ethylene. Reduce temperature to room temperature, while maintaining hydrogen and argon flow.
   h. Turn off all gases, open ends of furnace tube and remove chips. Place chips in conductive cases to reduce probability of static charge accumulation.
2. Probe Station Measurements (optional). At this stage it is a preferable to perform DC source drain measurements on the sensor regions (in this example, 38 regions) of each chip. Three or four chips can be tested in about 1 hour.
   a. Before performing measurements, take measures to reduce the likelihood of nanotube destruction from static charge. Ensure that relative humidity of room is around 45%. Use desktop deionizer. Individually connect each drain to ground with a 10 giga-ohm resistor in series. If static charge has built up, this last step will help to slowly dissipate it.
  b. It is also possible to electrolytically gate tubes at this point, using a drop of salty water and a third, gate electrode. If this is done, be sure to rinse chip with DI water before drying.

Step 6: Thin Silicon Nitride Layer
1. GSI PECVD for deposition of thin silicon nitride "protective" layer. First use "High Stress Nitride" recipe with the following modifications.
  a. Temperature=300 C
  b. RF #1=35% power; RF #2=0% Power
  c. Deposition time between 2 sec and 5 sec.
2. Next use "Low Stress Nitride" recipe with the following modifications.
  a. Temperature=300 C
  b. RF #1=35% power; RF #2=0% Power
  c. Deposition time between 5 and 10 sec, depending on the desired thickness of the nitride protective later.

Step 7: Microchannel/Nanochannel Sacrificial Chromium Layer
1. Photoresist Prep:
  a. p-20 primer; spin at 4000 RPM, 10,000 R/S, 45 sec
  b. LOR 1A (lift off resist); spin at 4000 RPM, 10,000 R/S, 45 sec
  c. Bake on hotplate at 180° C. for 5 min.
  d. SPR 955 0.9 Photoresist; spin at 4000 RPM, 5000 R/S, 45 sec
  e. Bake on hotplate at 100° C. for 2 min.
2. Photolithography
  a. Load desired mask(s) in mask aligner.
  b. Expose for 0.14 sec.
  c. Post exposure bake at 115° C. for 2 min
  d. Develop in 300 MIF for 75 sec. via hand dip and agitation.
3. Descum (Branson): run standard photoresist descum for 1 min.
4. E-beam Evaporation of Chromium (Even Hour or Odd Hour Evaporator)
  a. load samples, chromium, and new QCM
  b. evaporate 10 nm chromium at rate of 0.2-0.4 Å/s
5. Chromium Lift Off
  a. Place wafers in '1165' microposit remover and let sit overnight
  b. (next day) Sonicate for 20-30 min., transfer wafers to IPA, remove from IPA and dry with Nitrogen.

Step 8: Thick Silicon Nitride Layer
GSI PECVD for deposition of thick silicon nitride layer. A low stress nitride recipe (many suitable versions are known in the art) was used with the following modifications:
  a. Temperature=300° C.
  b. RF #1=35%; RF #2=0% Power
  c. Deposit for 5 sec. This results in a thin film for CNT protection.
  d. RF #1=19% power; RF #2=80% Power
  e. Deposit for 20 min. This results in approximately 2 μm of nitride.

Step 9: Access Hole Layer #1
1. Photoresist Prep:
  a. p-20 primer; spin at 3000 RPM, 5000 R/S, 45 sec
  b. SPR 220 3.0 Photoresist; spin at 3000 RPM, 5000 R/S, 45 sec
  c. Bake on hotplate at 115° C. for 2 min.
2. Photolithography
  a. Load desired masks in mask aligner.
  b. Exposure for 0.3 sec; 0.36 sec and 0.3 sec.
  c. Post exposure bake at 115° C. for 2 min
  d. Develop in 300 MIF for 90 sec. via hand dip and agitation.
3. Reactive Ion Etch (Oxford 80#1 or Oxford 80#2)
  a. Descum wafers using 20 sec. O2 plasma at 150 W
  b. $CHF_3/O2$ Nitride Recipe; etch for 40 min (Oxford 80#2).
  c. Fluorinated Polymer Removal using 40 sec. O2 plasma at 150 W
4. Resist Strip. Clean wafers using '1165' microposit remover. Soak for several hours or overnight. Transfer to IPA and then dry with nitrogen.

Step 10: Wet Chemical Etch of Chromium Sacrificial Material
1. Place chips in Cr-14 chrome etch. Etch for 6-8 hours or overnight.
2. Transfer chips to a beaker of $dH_2O$. Move $dH_2O$ beaker with chips to the photoresist hood. Allow chips to soak for 15-30 min.
3. Transfer chips to beaker of IPA. Let soak for 5 min. Remove and dry with nitrogen, and then do electrical measurements on chips, or continue to step 11, substep 2 below, without transferring to IPA and drying.

Step 11: Wet Chemical Etch of Thin Protective Nitride Layer
1. Insert chips into a beaker of IPA. Let soak for 5 min.
2. Transfer chips to a beaker of $dH_2O$. Transfer chips to a beaker of MF 312 (5% TMAH)
3. Move beaker with chips into a hood.
4. Transfer chips into a heated beaker of MF 312 (this beaker should be pre-heated to 70° C.). Etch at 70° C. for 20-60 min, depending on the thickness of protective nitride that must be removed.
5. Transfer chips to beaker of $dH_2O$. Move $dH_2O$ beaker with chips to the photoresist hood. Transfer chips to beaker of IPA. Let soak for 5 min. Remove and dry with nitrogen, and then do electrical DC measurements on chips.

Step 12: Deposition of Thin Silicon Nitride Layer #2
1. GSI PECVD for deposition of thin silicon nitride "protective" layer. Use "Low Stress Nitride" recipe with the following modifications.
2. Temperature=300° C.
3. RF #1=19% power; RF #2=80% Power
4. Deposition time=5 min.

Step 13: Access Hole Layer #2
1. Photoresist Prep:
  a. p-20 primer; spin at 3000 RPM, 5000 R/S, 45 sec
  b. SPR 220 3.0 Photoresist; spin at 3000 RPM, 5000 R/S, 45 sec
  c. Bake on hotplate at 115° C. for 2 min.
2. Photolithography
  a. Load mask in mask aligner.
  b. Expose for 0.3 sec
  c. Post exposure bake at 115° C. for 2 min
  d. Develop in 300 MIF for 90 sec. via hand dip and agitation.
3. Reactive Ion Etch (Oxford 80#1 or Oxford 80#2)
  a. Descum wafers using 20 sec. $O_2$ plasma at 150 W
  b. $CHF_3/O_2$ Nitride Recipe; etch for either 5-7 min (Oxford 80#)1 or 7-9 min (Oxford 80#2).
  c. Fluorinated Polymer Removal using 40 sec. $O_2$ plasma at 150 W 4. Resist Strip. Clean wafers using '1165' microposit remover. Soak for several hours or overnight. Transfer to IPA and then dry with nitrogen.

Step 14: Macroscopic Reservoir Attachment

1. Scratch openings at the end of each microchannel using a diamond scribe.
2. Prepare six reservoirs by slicing the ends off of pipet tips with a razor blade.
3. Put RTV sealant on the bottom edge of each pipet tip before pressing it to the surface at the microchannel end.

6.4 Example 4: Rapid, Ultra-Sensitive Detection of MicroRNA Expression from Single Cells Using Silicon Nanowire Transistors

6.4.1 Overview

Researchers have recently discovered that the expression of small ribonucleic acid molecules termed microRNA (miRNA) can be used to accurately classify human cancer and may assist in treatment. It is difficult to measure these cancer markers from single cells derived from complex tissues. This example describes a combination of nanotechnology and microfluidics to build a transformative technology that enables the research and clinical community to rapidly and sensitively measure microRNA expression from single cells. A combination of microfluidics with silicon nanowire electronic sensors is used for the rapid, ultra-sensitive, multiplexed detection of microRNA expression using single cells obtained from tissue samples.

It is known in the art that microRNA expression is correlated with various human cancers and that microRNAs can function as tumor suppressors and oncogenes. The ability to differentiate a benign from cancerous tumor using a single cell based on its microRNA expression, as demonstrated in the present example, is a powerful tool in the research, diagnosis and treatment of cancer. This example demonstrates a robust technology combining microfluidics with silicon nanowire electronic sensors for the rapid, ultrasensitive, multiplexed detection of miRNA expression using single cells obtained from tissue samples. Established 'top-down' nanofabrication techniques using standardized complementary metal-oxide semiconductor (CMOS) compatible technology are employed to efficiently construct reproducible arrays of semiconducting silicon nanowire transistors. These nanowires are individually functionalized with commercially available probe oligonucleotides designed to bind to known miRNAs, or corresponding complementary DNA (cDNA), that have been implicated in tumorigenesis. Combining the nanowires with microfluidic delivery channels for the target miRNAs enables real-time, ultrasensitive electronic detection of miRNA expression.

Silicon nanowires have already been shown to be extremely sensitive for the label-free detection of DNA (Gao Z, et al. "Silicon Nanowire Arrays for Label-Free Detection of DNA." Analytical Chemistry, 2007: 3291-3297; Hahm J, Lieber C M. "Direct ultrasensitive electrical detection of DNA and DNA sequence variations using nanowire nanosensors." Nano Letters, 2004: 51-54), proteins (Stern E, et al. "Label-free immunodetection with CMOS-compatible semiconducting nanowires." Nature, 2007: 519-522), and single viruses (Patolsky F, et al. "Electrical detection of single viruses." Proc Natl Acad Sci USA, 2004: 14017-1402) since their high surface to volume ratio allows their carrier mobility to be modulated by minute changes in the electric potential at their surface. Compared to quantitative real-time polymerase chain reaction, the method described in this example has two main advantages: it does not require potentially biasing amplification of reverse transcribed cDNA, and electronic detection provides a more robust and simpler method for point of care devices than fluorescent detection. Additionally, a separate microfluidic device can be added to perform all single-cell sample preparation subsequent to delivery of the reverse transcribed cDNA to the charge sensor chip. Nanofabrication techniques well known in the art are employed to efficiently construct reproducible arrays of silicon nanowire transistors. These nanowires are individually functionalized with commercially available probe oligonucleotides designed to bind to known microRNAs that have been implicated in tumorigenesis. Combining the nanowires with microfluidic delivery channels for the target microRNAs enables real-time, ultra-sensitive electronic detection of microRNA expression.

First, nanolithography tools are used to fabricate silicon wafers each containing hundreds of nanowire sensor chips. This process optimized using standard semiconductor processing technology that offers excellent reproducibility and allows direct integration of the chips with electrical readout circuits. The electronic properties of the nanowire transistors are characterized to determine the geometrical properties that maximize gain while limiting noise.

Second, a network of microfluidic channels is integrated onto the sensor chip for the controlled delivery of probes and target microRNAs to different regions allowing for multiplexed detection. The ability to functionalize the nanowire surfaces with specific probe oligonucleotides is determined using fluorescent and electrical binding assays known in the art.

Third, key factors determining the nanowire sensor performance limits are systematically investigated. These factors include the minimum amount of microRNA that can be detected, the change in the device response for given changes in concentration, selectivity, and cross-reactivity.

Fourth, a separate microfluidic device is developed for manipulating, lysing, and extracting microRNA from a single cell for subsequent delivery to the charge sensor chip. Thus by combining recent advances in nanoelectronics and microfluidics, a robust sensor is developed for the label-free electronic profiling of microRNA expression in a single cell with all processing steps integrated on the chip.

This technology has significant advantages over the current state of the art since it provides sensitive detection without potentially biasing amplification steps, dramatically reduces the amount of expensive reagents required, and is highly portable. By developing a point of care system to measure microRNA expression from complex tissue tumors, the embodiment of the invention described in this example has significant potential to assist with early stage diagnosis and prognosis of cancer.

6.4.2 Introduction

MicroRNAs (miRNAs) are a recently discovered class of non-protein-coding RNAs consisting of ~22 nucleotides that regulate gene expression (Ambros V. 2003, Cell, Vol. 113, pp. 673-676). Within the last five years, researchers have found that microRNA expression profiles of a relatively small number of genes can be used to identify solid tumor cancers (Lu J, et al. "MicroRNA expression profiles classify human cancers." Nature 435, no. 7043 (2005): 834-838; Volinia S, et al. "A microRNA expression signature of human solid tumors defines cancer gene targets." Proc Natl Acad Sciences USA 103, no. 7 (2006): 2257-2261), and can be used to identify the tissue in which cancers of unknown primary origin arose, a major clinical problem (Rosenfeld N, et al. "MicroRNAs accurately identify cancer tissue origin." Nature Biotechnology 26, no. 4 (2008): 462-469). It is believed that the differential expression of miRNAs in various tumors could be a powerful tool in diagnosing and treating cancer (Esquela-Kerscher A, Slack F J. "Oncomirs—microRNAs with a role in cancer." Nature Reviews Cancer, 2006: 259-269). The example describes the development of a chip comprising semiconducting silicon nanowire transistors for the rapid ultrasensitive detection of microRNA profiles from single cells extracted from complex tissue. An electrical detector capable of sensitively and rapidly measuring miRNA expression from single cells derived from complex tumor tissue will have a major impact in the early stage diagnosis, prognosis, and treatment of certain forms of cancer.

Pancreatic cancer, for example, is the fourth leading cause of cancer related deaths in the U.S. with the worst prognosis of all cancers, reflecting the inability to detect it at an early stage and lack of effective therapy (Oliveira-Cunha M, Siriwardena A K, Byers R. "Molecular Diagnosis in Pancreatic Cancer." Diagnostic Histopathology, 2008: 214-222). An miRNA signature has been identified that distinguishes pancreatic cancer from normal and benign pancreas (Lee E J, et al. "Expression profiling identifies microRNA signature in pancreatic cancer." International Journal of Cancer, 2007: 1046-1054). The methods used to determine this signature, however, require an initial starting sample of thousands of cells per individual. As there is growing evidence linking altered miRNA expression to chronic lymphocytic leukemia (Calin G A, et al. "MicroRNA profiling revelas distinct signatures in B cell chronic lymphocytic leukemias." Proc Natl Acad Sci USA, 2004: 11755-11760), colorectal cancer (Miachel M Z, et al. "Reduced accumulation of specific microRNAs in colorectal neoplasia." Mol Cancer Res, 2003: 882-831), lung cancer (Johnson S, et al. "RAS is regulated by the let-7 microRNA family." Cell, 2005: 635-647), breast cancer (lorio M V, et al. "MicroRNA gene expression deregulation in human breast cancer." Cancer Res, 2005: 7065-7070), and thyroid cancer (He H, et al. "The role of microRNA genes in papillary thyroid carcinoma." Proc Natl Acad Sci USA, 2005: 19075-19080), the ability to measure a distinct miRNA signature from single cells in real time therefore provides an indispensable tool for the research and clinical cancer community. A sensor device that requires only a single cell will also provide cancer researchers with a unique tool to study the time development of miRNA expression in animal models of cancer with increased fidelity. Furthermore, the portability of the sensor (chips are approximately 1 cm by 1 cm and are only attached to a computer via wires for readout) and the ability to measure the concentration of vanishingly small quantities of miRNA in tens of minutes makes it more practical for a point-of-care device than any existing technology. Consequently, the embodiment of the invention described in this example has the potential for major impact in the cancer community. Further, miRNAs have been implicated in the pathogenesis of several human diseases including neurodegenerative disorders, viral disease, diabetes, and obesity (Weiler J, et al. "Anti-miRNA oligonucleotides (AMOs): ammunition to target miRNAs implicated in human disease?" Gene Therapy, 2006: 496-502).

6.4.3 Research Design

Fabrication of Chips Containing Arrays of Semiconducting Silicon Nanowires from Silicon-on-Oxide Wafers Using Standardized Semiconductor Technology Chips containing semiconducting silicon nanowires are fabricated using CMOS technology. Nanolithography tools are used for the top-down fabrication of wafers that each contain hundreds of nanowire sensor chips. This process is optimized using standard semiconductor processing technology that offers excellent reproducibility and allows direct integration of the chips with electrical readout circuits. The electronic properties of the nanowire transistors are characterized to determine the geometrical properties (primarily width and height) that maximize their transconductance while limiting noise.

Prototype chips containing nanowires of different lateral dimensions are electronically tested using standard methods. After comparing the transistor properties using both a liquid and bulk gate, there is the potential for chips with wider nanowires (approximately 500 nm) to perform as well as chips with narrow (100 nm or less) nanowires. This allows fabrication of the chips using stepper photolithography rather than the more costly and time consuming electron beam lithography that is planned for the narrow wire prototypes. An amplifier and controller software for the simultaneous readout of nanowire channels is also constructed using standard, art known methods.

Integration of a Network of Microfluidic Channels into a Chip

Microfluidic channels are integrated into a chip for the controlled delivery of probes and target microRNAs to addressable regions, which allows for multiplexed detection. The design and fabrication of the channels is performed using standard art known methods. Microfluidic channels are integrated into the chip using photolithography and thermal bonding of photoresist directly to glass cover wafers. The inclusion of valves to individually address different nanowires is made and optimized using standard art known methods.

The ability to functionalize the nanowire surfaces after silanization with specific probe oligonucleotides is determined using standard fluorescent and electrical binding assays. The silanization procedure to functionalize the nanowires is well known in the art and the binding of probes to nanowires can be validated using standard methods.

Determination of the Nanowire Sensor Performance Limits

The nanowire sensor performance limits are systematically determined for multiplexed miRNA detection and miRNA profile expression in pancreatic tumor cell lines is measured. The performance factors include the minimum amount of microRNA that can be detected, the change in the device response for given changes in spiked miRNA concentration, selectivity, cross-reactivity, and the number of different miRNAs that can be measured simultaneously. Using pancreatic tumor cell lines the charge sensor's performance in measuring 16 of the most aberrantly expressed miRNAs in pancreatic cancer (Lee E J, et al. "Expression profiling identifies microRNA signature in pancreatic cancer." International Journal of Cancer, 2007: 1046-1054) is compared with Northern blotting and quantitative PCR results.

Development of a Separate Microfluidic Delivery Device

A separate microfluidic device is developed for manipulating, lysing, and extracting microRNA from a single cell for subsequent delivery to the charge sensor chip. Using soft lithography techniques, polydimethylsiloxane (PDMS) chips are constructed with different valving mechanisms and characterized for the transportation of a single cell from a reservoir to an extraction chamber where the cell is lysed. The construction of the microfluidic channels and integration of soft pneumatic valves is achieved using standard methods known in the art.

The miRNA is reversed transcribed to cDNA using standard methods. The cDNA is electrophoretically driven through a capillary electrophoresis separation nanochannel and cDNA mobility is measured using methods described herein, then diverted to the charge sensor chip for subsequent quantification.

6.4.4 Methods

A chip is developed composed of semiconducting silicon nanowires for the real-time and ultrasensitive detection of microRNA obtained from single cells of complex tissue. Semiconducting nanowires combined with surface binding provide a robust label-free detection method that is attractive for applications in life sciences. The chip contains individually addressable semiconducting silicon nanowires that have been functionalized with oligonucleotide probes (Invitrogen) specific for binding complentary DNA (cDNA) that have been reversed transcribed from miRNA. The detection method relies on the ability of the nanowires to act as field effect transistors that exhibit a conductivity change in response to minute variations in the electrical potential at their surface, which occurs when the target and probe molecules hybridize. The sensitivity of the nanowires results because the variation in electric potential (termed gating) at their surface leads to depletion or accumulation of charge carriers throughout the entire cross-sectional bulk of the wire.

FIG. 23 shows a schematic representation of a nanowire sensing device. A semiconducting silicon nanowire (dark gray cylinder) is functionalized with oligonucleotide probes for miRNA detection (light gray S-curves) is connected via platinum probe electrodes on the silicon-on-insulator chip. A silver reference electrode is inserted into the microfluidic channel electrolyte solution and all wires are connected to a computer measuring current as a function of time. The current changes significantly when target cDNA molecules bind to the nanowire and alter the local electrostatic potential. In actuality, the charge sensor chip is wire bonded to a leadless chip carrier and inserted into a custom made amplifier so that a single cable connects the chip to the computer.

Semiconducting silicon nanowires are known in the art to achieve sensitive label-free DNA detection via this field-effect mechanism, sensing DNA at concentrations down to femtomolar levels and requiring only zeptomoles of starting material (6).

There are currently two broad methods for producing silicon nanowires, typically referred to as 'topdown' or 'bottom-up' approaches. The bottom-up approach relies on the natural ability of certain atoms and molecules to self-assemble into more complex configurations based on controlled chemical reactions. The top-down method begins with bulk materials and uses nanofabrication machines to pattern and etch the material into the desired nanostructures. The bottom-up approach has achieved ultrasensitive label-free detection of biological species, such as DNA (Hahm J, Lieber C M. "Direct ultrasensitive electrical detection of DNA and DNA sequence variations using nanowire nanosensors." Nano Letters, 2004: 51-54), proteins (Cui Y, Lieber C M. "Functional nanoscale electronic devices assembled using silicon nanowire building blocks." Science, 2001: 851-853), and viruses (Patolsky F, et al. "Electrical detection of single viruses." Proc Natl Acad Sci USA, 2004: 14017-1402). However, the method relies on transferring previously synthesized nanowires to wafers with predefined electrical contacts. The inability to synthesize the nanowire in a precise location results in variable device yield and performance per wafer. Large scale fabrication of individually addressable silicon nanowires for multiplexed sensing requires a uniform and repeatable process that results in high yields of nanowires per chip with similar electrical properties.

Consequently, a top-down approach to nanowire fabrication that is fully compatible with complementary metal-oxide-semiconductor fabrication (CMOS) techniques is preferred. This means that the chips can be produced cost-effectively in bulk at any semiconductor foundry. The semiconducting nanowire sensors of the invention differ from DNA microarray chips that have been the workhorse thus far in genome wide measurements of RNA expression in several aspects. The major difference is that the binding of the target and probe nucleic acid directly alters the current (typically micro or nano amperes) running through a silicon nanowire, and this change in current can be identified in real-time. The nanowire sensor is advantageous because it eliminates the necessity of labeling the target with a fluorescent probe for readout since it measures the altered electric potential induced by the hybridization. This means that the lasers, spectral filters, and imaging equipment necessary for microarray measurements are now replaced by wires connecting the nanowire chip to a computer.

In another embodiment, the electrical device comprises a system of microfluidic channels, as shown in FIG. 24, which has been used for quantitative single molecule analysis (see Section 6.1), to interface to the nanowire arrays. The microfluidic channel network provides multiplexed detection since spatially separated nanowires can be selectively functionalized with probes specific to a given miRNA. Since the silicon nanowires have a native oxide coating, the extensive information available in the art for chemistries to link nucleic acid probes to silica or glass surfaces can also be used for the nanowire modification. For example, silanization protocols can be used for nanowire functionalization (19). Chips containing, e.g., 4, 8, and 16 parallel microfluidic channels with a common input and output reservoir are designed so that a single syringe pump can be attached for all fluid handling (see FIG. 25). Chips containing one to several thousand parallel microfluidic channels are contemplated. The channels are fabricated using contact photolithography in combination with SU-8 photoresist, a technique well known in the art, and are implemented with simple mechanical valves for controlling flow through a given region.

FIG. 24 (left) is a photograph of a 100 millimeter diameter fused silica wafer containing 27 devices, each consisting of a parallel array of 16 fluidic channels for single molecule analysis. Fluidic ports are added (left side of wafer) to interface with fluid reservoirs leading to channels. FIG. 24 (middle) is a schematic of a nanochannel array device. (A) Cross section of device consisting of two bonded fused silica wafers (a,b) with the upper wafer containing the nanostructures. A microchannel bridges the interface between the nanochannels and attached fluid reservoirs (c). Electrical connections to the channel are made via platinum electrodes (d). (B) Close-up of the nanochannel array in the upper wafer. DNA molecules have been drawn in the loading zone (a), as they enter a nanochannel (b), and in an elongated equilibrium conformation in a nanochannel (c). Middle figure from Mannion et al., *Biophys. J.* 90, 12 (2006).

FIG. 24 (right) is a top down scanning electron micrograph of nanochannel array (c) and magnified image of a single nanochannel (d) with dimension 150×135 nm (width× height). The scale bars are 920 and 195 nm in images (c) and (d), respectively. Right figure from Levy et al., *Nano Lett.* 8, 11 (2008).

FIG. 25 is a schematic representation of the microfluidic network on the nanowire sensor chip. In this embodiment, it comprises eight parallel channels connected by a common inlet and outlet reservoir. The rectangles in the central portion of the chip indicate regions of semiconducting nanowire arrays. The rectangles on the edge of the chip are connected to the source and drain regions of each nanowire (not shown) and provide for wire bonding the chip to an integrated circuit. The chip is approximately one cm per side and will fit inside a custom amplifier.

The microfluidic channel network serves to significantly reduce the time required for hybridization (relative to microwells) since it confines the target to within tens of microns of the probe. The optimal flow rate for the target solution through the channel is determined to reach equilibrium in the order of minutes based on the geometry of the chip, target concentration, and considerations of reaction-versus diffusion-limited kinetics (Squires T, Messinger R, Manalis S. "Making it stick: convection, reaction, and diffusion ni surface-based sensors." Nature Biotechnology, 2008: 417-426). The use of microfluidic channels results in an internal volume on the chip of a few nanoliters, which serves to reduce the volume of expensive reagents required to perform the measurements.

A separate microfluidic device for the handling, lysing, reverse transcription, and collection of miRNA from single cells for subsequent delivery to the charge sensor chip is also developed. Before setting forth the fabrication process, the comparison of the sensor of the invention to existing technologies is addressed. As previously stated, microarray DNA chips are one of the most powerful and widely used methods for determining genome wide miRNA expression. However, the initial amount of RNA required is on the order of micrograms so the technology is not suited for quantification from single cells.

Northern blotting is an older technology for measuring RNA expression that is rather time-consuming, requires the use of radioactive material, and lacks the sensitivity of quantitative real-time reverse transcriptase polymerase chain reaction (RT-qPCR).

RT-qPCR is often described as the gold standard for sensitive RNA quantification. This technique is capable of measuring RNA expression from single cells, offers a wide dynamic range, and is the most analogous in terms of performance to our proposed charge sensor. RT-qPCR consists of producing a single strand cDNA copy of the RNA through reverse transcription, amplification of the cDNA using PCR, and the detection and quantification of the cDNA products in real time. Both the charge sensor and RT-qPCR share the initial step (which can be quite variable depending on the use of primer) of reverse transcribing the RNA in common. However, there are a number of problems cited in the literature for using PCR to amplify the cDNA which are avoided in the charge sensor approach due to its ultrasensitive ability to detect single binding events (Bustin S, Nolan T. "Pitfalls of Quantitative Real Time Reverse-Transcription Polymerase Chain Reaction." Journal of Biomolecular Techniques, 2004: 155-166). Inhibitory components frequently found in biological samples can result in a significant reduction in the sensitivity and kinetics of the PCR amplification cycle, which can create false-negative results. Also, reproducible quantification of any low abundance cDNA target is problematic due to the variability inherent in amplification of small amounts of cDNA within a complex nucleic acid mixture. This so called 'Monte-Carlo' effect implies that the lower the abundance of a template, the less likely its true abundance is reflected after amplification (Karrer E E, et al. "In situ isolation of mRNA from individual plant cells: Creation of cell-specific cDNA libraries." Proc Natl Acad Sci USA, 1995: 3814-3818).

A standard protocol for performing RT-qPCR assigns a total time of approximately 15 hours; roughly fifty percent of that time is spent determining the inhibitors, optimizing the PCR step, and performing the PCR amplification (Nolan T, Hands R, Bustin S. "Quantification of mRNA using real-time RT-PCR." Nature Protocols, 2006: 1559-1582). For a technology that has existed for about 20 years, there is considerable lack of standardization at many stages of the protocol that researchers find frustrating and has led to conflicting results (Garson J A, et al. "Unreliable real-time PCR analysis of human endogenous retrovirus-W HERV-W_RNA expression and DNA copy-number in multiple sclerosis." AIDS Research and Human Retroviruses, 2009: 377-378) and retractions (Bohlenius H, et al. "Retraction." Science, 2007: 317). Consequently, the innovative merging of microfluidic and nanoelectronic technologies in the sensor electrical detector for single cell miRNA expression quantification leads to significant improvement over state of the art technologies. The advantages of the semiconducting silicon nanowire sensor are the ability to achieve ultrasensitive labelfree detection without amplification, standard fabrication techniques leading to high uniformity, yield, and reproducibility, reduced expense for reagents, real-time readout, and ease of portability for possible point of care use. Also, the use of CMOS processing means the devices could be produced cost-effectively in bulk.

Fabrication Process for Constructing Nanowire Sensors

Beginning with silicon-oninsulator (SOI) wafers that consist of consecutive layers of approximately 360 nm of polycrystalline silicon<100>, 400 nm of silicon oxide, and 500 microns of a silicon substrate (SOITEC), the top silicon layer is progressively oxidize and HF etched to thin it to 40 nm thickness. Photolithography and reactive ion etching (RIE) are used to define contact structures for the nanowires. These structures are subsequently implanted with boron ions using art known methods so that the modulation of charged carriers occurs across the nanowire rather than the electrode-wire interface, as is the case for the Schottky barrier transistor.

Nanowires of varying width between 50 and 1000 nm and approximately 3 microns in length are defined by electron beam lithography. The top oxide is removed by reactive ion etch except for over the nanowire and contact structures where it serves as a mask. An anisotropic TMAH wet etch is used to define the nanowires on the buried oxide surface, relying on the differential etch rates for silicon<100> and <111> directions (8). This is a preferred step in the process since it results in smooth nanowires that have been shown to have excellent electrical properties relative to wires formed by RIE.

Photolithography and lift-off techniques are used to deposit metal pads for electrical contacts and for contact to the back silicon substrate. The contact lines are passivated with LPCVD silicon nitride to allow operation of the device in an electrolyte solution.

Chips are fabricated with, e.g., 16, 32, and 64 separately addressable charge sensors, although ranges of is 2-10, 10-50, 50-100, or 100-500 charge sensors are contemplated. In some embodiments, a plurality of charge sensors (e.g., 2-10, 10-50, 50-100, or 100-500) is located in a single nanofluidic channel on the electrical detector. In other embodiments, the plurality is distributed among 2 or more nanofluidic channels.

Chips are also fabricated in which the number of charge sensors (e.g., nanowires) connecting single source and drain electrodes is e.g., 1, 4, and 8. Increasing the number of nanowires per electrical contact can result in more uniform properties for the transistors and provides redundancy.

Each silicon wafer is diced into approximately 150 chips that are one square centimeter in area. The chips are wire-bonded to a 68-pin leadless chip carrier integrated circuit. The chips are placed in a custom built box that provides for amplified DC readout on 16 channels simultaneously and is connected to a data acquisition card (National Instruments) interfaced to a computer.

For sensing operations a Ag/AgCl reference electrode enclosed in a small glass frit are inserted into the solution to set the gate voltage. Custom software (LabView) is used to determine important semiconductor parameters of the nanowire transistors including threshold voltage, transconductance, and subthreshold slope. These parameters determine how sensitively and quickly the nanowires respond to changes in their electrostatic environment.

The nanowires are calibrated by measuring the change in current induced by variations in pH so that they can be compared to other nanoelectronic devices. After validating the electronic properties of the nanowires, a silanization functionalization scheme is optimized, using standard methods, for the attachment of oligonucleotide probes. Fluorescently labeled probes (Invitrogen) can be used in this optimization to visually verify binding as well as electronic means. A systematic determination is made, using standard methods, of the nanowire sensor performance limits for multiplexed miRNA detection using probes and targets designed for controls in microarray experiments. The performance factors include the minimum amount of microRNA that can be detected, the change in the device response for given changes in spiked miRNA concentration, selectivity, cross-reactivity, time to reach binding equilibrium, the variation in response based on buffer salt concentration, and the number of different miRNAs that can be measured simultaneously.

These tests are performed using commercially available oligonucleotide probes and cDNA targets (Invitrogen). The basic protocol is to measure the nanowire conductance as a function of time at the source-drain and liquid gate potentials that maximize the signal to noise ratio (as determined from the electronic characterization) while the targets are flushed over the nanowires in the microfluidic channels. An important parameter of the assay is the buffer salt concentration since it determines the length over which changes in the electrostatic potential surrounding charged molecules can effectively gate the nanowires (termed the Debye length). With a low salt concentration, hybridization is detectable over large distances from the nanowire but this will also increase the time for hybridization since the target and probe will then repel each other more strongly. Thus, it is preferable to determine a proper balance between these competing factors for an optimal salt concentration.

With the completion of these measurements, the nanowire sensor performance limits for multiplexed miRNA detection are demonstrated in a controlled environment absent complications from impure miRNA or reverse-transcriptase.

Having validated the performance of the nanowires in a controlled environment, the miRNA profile expression is then measured in pancreatic tumor cell lines (American Type Tissue Collection, VA), purified total RNA from tumor pancreas (Ambion), and total RNA from normal pancreases (Ambion). The same protocol can be followed for total RNA extraction (Trizol, Invitrogen) and reverse transcriptase reactions (Applied Biosystems) as used in Lee et al. 2007 (Lee E J, et al. "Expression profiling identifies microRNA signature in pancreatic cancer." International Journal of Cancer, 2007: 1046-1054) where a unique miRNA signature of pancreatic cancer was identified using RT-qPCR. The probes functionalized to the nanowires are the same that were used in the Northern blotting tests of Lee et al. 2007 that were used to confirm the RT-qPCR results. This test allows quantitatively assessment of the performance of nanowire miRNA detection relative to RT-qPCR in a 'real-world' experiment that attempts to deliver answers to important cancer research goals.

The final component to fully make use of the nanowire sensor's sensitivity is the implementation of a separate delivery system consisting of a microfluidic chip for single cell manipulation, lysing, performing reverse transcription, and extracting the cDNA. This can be accomplished, in one embodiment, by using soft-lithographic techniques to make cheap disposable microfluidic channels from polydimethylsiloxane (PDMS) bonded to glass slides that incorporate pneumatic actuated valves (Unger M A, et al. "Monolithic Microfabricated Valves and Pumps by Multilayer Soft Lithography." Science, 2000: 113-116), a temperature controller, and a capillary electrophoresis channel.

A schematic illustration of this embodiment of the sensor device is shown in FIG. 26. Cells are electrophoretically transported from an inlet reservoir through a T-junction where individual cells are diverted to a 500 nL reaction chamber that can be isolated using the pneumatic valves. The cells are rapidly freeze-thaw lysed in less than one minute by placing a chip of dry ice over the chamber (Toriello N, et al. "Integrated microfluidic bioprocessor for single-cell gene expression analysis." Proc Natl Acad Sci USA, 2008: 20173-20178). In this embodiment, for simplicity, both the single cell capture and lysing require external input from an experimenter. Other embodiments can be easily contemplated by the skilled practitioner that do not require external input.

The lysed cell is reverse-transcribed at a constant temperature of 42° C. for 30 minutes in the reaction chamber that contains resistive heating elements on the back side of the glass substrate fabricated by sputtering titanium and platinum, photolithography, and a chemical etch. The lysed cellular contents along with the transcribed cDNA are electrophoretically transported from the reaction chamber through a capillary electrophoresis channel and the cDNA is diverted through a separate channel to a holding outlet for integration with the charge sensor chip.

The time that the cDNA should be diverted from the CE channel (for a given separation voltage applied along the channel) is experimentally determined beforehand using fluorescently labeled cDNA probes and microscopy and standard techniques known in the art.

FIG. 26 is a schematic illustration of PDMS microfluidic channels for cell manipulation, lysing, reverse transcription, and capillary electrophoresis of cDNA. Cells are electrophoretically driven from inlet A to a waste outlet; along the way the external voltages are switched to send a single cell into the reaction chamber B where it is held in isolation for cell lysing and reverse transcriptase. The vertically oriented and L-shaped channels indicate control lines that are activated by pumps off the chip and act as valves by compressing and pinching off flow in the fluidic channels beneath them. Reagents for reverse transcriptase are pumped through inlet C to the reaction chamber that contains a resistive heating element. The entire lysed contents along with the cDNA are then electrophoretically driven through a capillary electrophoresis channel (purple) to a waste outlet. At a previously measured time during the electromigration the voltage is temporarily switched to send the cDNA to a collection reservoir for subsequent delivery to the charge sensor chip.

6.5 Example 5: Conformation, Length and Speed Measurements of Electrodynamically Stretched DNA in Nanochannels

6.5.1 Abstract

The example demonstrates a method for rapidly and precisely measuring the conformation, length, speed and fluorescence intensity of single DNA molecules constrained by a nanochannel. DNA molecules were driven electrophoretically from a nanoslit into a nanochannel to confine and dynamically elongate them beyond their equilibrium length for repeated detection via laser induced fluorescence spectroscopy. A single molecule analysis algorithm was developed to analytically model bursts of fluorescence and determine the folding conformation of each stretched molecule. This technique achieved a molecular length resolution of 114 nm and an analysis time of around 20 ms per molecule, which enabled the sensitive investigation of several aspects of the physical behavior of DNA in a nanochannel. $\lambda$-bacteriophage DNA was used to study the dependence of stretching on the applied device bias, the effect of conformation on speed, and the amount of DNA fragmentation in the device. A mixture of $\lambda$-bacteriophage with the fragments of its own HindIII digest, a standard DNA ladder, was sized by length as well as by fluorescence intensity, which also allowed the characterization of DNA speed in a nanochannel as a function of length over two and a half orders of magnitude.

6.5.2 Introduction

The demand for increased analytical ability in the biological sciences has spurred the development of submicrometer and nanometer scale structures for single molecule analysis. These structures facilitate the manipulation and analysis of biological molecules with higher speed and precision than is possible with conventional technology. Such capabilities promise to be useful in applications ranging from genomic sequencing to pathogen detection, and in fundamental research in fields such as molecular biology and biophysics.

An assortment of nanoscale structures for enhanced single-molecule analysis has recently been developed, including solid-state nanopores (Li, J., D. Stein, C. McMullan, D. Branton, M. J. Aziz, and J. A. Golovchenko. 2001. Ion-beam sculpting at nanometer length scales. Nature 412: 166-169; Li, J. L., M. Gershow, D. Stein, E. Brandin, and J. A. Golovchenko. 2003. DNA molecules and configurations in a solid-state nanopore microscope. Nat. Mater. 2:611-615), entropic trap arrays (Han, J. and H. G. Craighead. 1999. Entropic trapping and sieving of long DNA molecules in a nanofluidic channel. J. Vac. Sci. Technol. A-Vac. Surf. Films 17:2142-2147; Han, J. and H. G. Craighead. 2000. Separation of long DNA molecules in a microfabricated entropic trap array. Science 288:1026-1029; Han, J. Y. and H. G. Craighead. 2002:Characterization and optimization of an entropic trap for DNA separation. Anal. Chem. 74:394-401), zero mode waveguides (Samiee, K. T., M. Foquet, L. Guo, E. C. Cox, and H. G. Craighead. 2005. lambda-repressor oligomerization kinetics at high concentrations using fluorescence correlation spectroscopy in zero-mode waveguides. Biophys. J. 88:2145-2153; Levene, M. J., J. Korlach, S. W. Turner, M. Foquet, H. G. Craighead, and W. W. Webb. 2003. Zero-mode waveguides for single-molecule analysis at high concentrations. Science 299:682-686), metallic nanoslit near field scanners (Tegenfeldt, J. O., O. Bakajin, C. F. Chou, S. S. Chan, R. Austin, W. Fann, L. Liou, E. Chan, T. Duke, and E. C. Cox. 2001. Near-field scanner for moving molecules. Phys. Rev. Lett. 86:1378-1381), and pillar arrays (Turner, S. W. P., M. Cabodi, and H. G. Craighead. 2002. Confinement-induced entropic recoil of single DNA molecules in a nanofluidic structure. Phys. Rev. Lett. 88:1281031-1281034; Kaji, N., Y. Tezuka, Y. Takamura, M. Ueda, T. Nishimoto, H. Nakanishi, Y. Horiike, and Y. Baba. 2004. Separation of long DNA molecules by quartz nanopillar chips'under a direct current electric field. Anal. Chem. 76:15-22; Huang, L. R., J. O. Tegenfeldt, J. J. Kraeft, J. C. Sturm, R. H. Austin, and E. C. Cox. 2002. A DNA prism for high-speed continuous fractionation of large DNA molecules. Nat. Biotechnol. 20:1048-1051).

Submicrometer- and nanometerscale fluidic channels used in conjunction with fluorescence spectroscopy have also shown significant potential for the manipulation and analysis of single DNA molecules. Much of this work has focused on the implementation of rapid and sensitive analytical techniques such as fragment sizing (Foquet, M., J. Korlach, W. Zipfel, W. W. Webb, and H. G. Craighead. 2002. DNA fragment sizing by single molecule detection in submicrometer-sized closed fluidic channels. Anal. Chem. 74:1415.1422; Chou, H. P., C. Spence, A. Scherer, and S. Quake. 1999. A microfabricated device for sizing and sorting DNA molecules. Proc. Natl. Acad. Sci. U.S.A. 96:11-13, correlation spectroscopy (Foquet, M., J. Korlach, W. R. Zipfel, W. W. Webb, and H. G. Craighead. 2004. Focal volume confinement by submicrometer-sized fluidic channels. Anal. Chem. 76:1618-1626), binding assays (Stavis, S. M., J. B. Edel, K. T. Samiee, and H. G. Craighead. 2005. Single molecule studies of quantum dot conjugates in a submicrometer fluidic channel. Lab Chip 5:337-343), identification of nucleic acid engineered labels (Stavis, S. M., J. B. Edel, Y. G. Li, K. T. Samiee, D. Luo, and H. G. Craighead. 2005. Detection and identification of nucleic acid engineered fluorescent labels in submicrometre fluidic channels. Nanotechnology 16:S314-S323), mobility measurements (Stavis, S. M., J. B. Edel, Y. G. Li, K. T. Samiee, D. Luo, and H. G. Craighead. 2005. Single-molecule mobility and spectral measurements in submicrometer fluidic channels. J. Appl. Phys. 98:449031-449035), and polymerase chain reaction analysis (Stavis, S. M., S. C. Corgié, B. R. Cipriany, H. G. Craighead, and L. P. Walker. 2007. Single molecule analysis of bacterial PCR products in submicrometer fluidic channels, Biomicrofluidics 1, 034105). The physical behavior and genetic analysis of single DNA molecules in nanochannels are subjects of particular interest as well (Kaji, N., Y. Tezuka, Y. Takamura, M. Ueda, T. Nishimoto, H. Nakanishi, Y. Horiike, and Y. Baba. 2004. Separation of long DNA molecules by quartz nanopillar chips under a direct current electric field. Anal. Chem.

76:15-22; Huang, L. R., J. O. Tegenfeldt, J. J. Kraeft, J. C. Sturm, R. H. Austin, and E. C. Cox. 2002. A DNA prism for high-speed continuous fractionation of large DNA molecules. Nat. Biotechnol. 20:1048-1051; Mannion, J. T. and H. G. Craighead. 2007. Nanofluidic structures for single biomolecule fluorescent detection. Biopolymers 85:131-143; Craighead, H. 2006. Future lab-on-a-chip technologies for interrogating individual molecules. Nature 442:387-393).

DNA has been hydrodynamically linearized in submicrometer fluidic devices, which can be used for genomic sequencing when combined with repeated fluorescence detection (Chan, E. Y., N. M. Goncalves, R. A. Haeusler, A. J. Hatch, J. W. Larson, A. M. Maletta, G. R. Yantz, E. D. Carstea, M. Fuchs, G. G. Wong, S. R. Gullans, and R. Gilmanshin. 2004. DNA mapping using microfluidic stretching and single-molecule detection of fluorescent site-specific tags. Genome Res. 14:1137-1146; Bakajin, O. B., T. A. J. Duke, C. F. Chou, S. S. Chan, R. H. Austin, and E. C. Cox. 1998. Electrohydrodynamic stretching of DNA in confined environments. Phys. Rev. Lett. 80:2737-2740; Larson, J. W., G. R. Yantz, Q. Zhong, R. Charnas, C. M. D'Antoni, M. V. Gallo, K. A. Gillis, L. A. Neely, K. M. Phillips, G. G. Wong, S. R. Gullans, and R. Gilmanshin. 2006. Single DNA molecule stretching in sudden mixed shear and elongational microflows. Lab Chip 6:1187-1199111).

DNA molecules have also been shown to become elongated to an extended equilibrium length when introduced into a nanochannel (Tegenfeldt, J. O., C. Prinz, H. Cao, S. Chou, W. W. Reisner, R. Riehn, Y. M. Wang, E. C. Cox, J. C. Sturm, P. Silberzan, and R. H. Austin. 2004. The dynamics of genomic-length DNA molecules in 100-nm channels. Proc. Natl. Acad. Sci. U.S.A. 101:10979-10983), which has been utilized for restriction mapping (Riehn, R., M. C. Lu, Y. M. Wang, S. F. Lim, E. C. Cox, and R. H. Austin. 2005. Restriction mapping in nanofluidic devices. Proc. Natl. Acad. Sci. U.S.A. 102:10012-10016). Further work has investigated other aspects of the physics of elongated DNA strands in nanochannels, including entropically driven dynamics and compression against nanoscale constrictions (Reisner, W., K. J. Morton, R. Riehn, Y. M. Wang, Z. N. Yu, M. Rosen, J. C. Sturm, S. Y. Chou, E. Frey, and R. H. Austin. 2005. Statics and dynamics of single DNA molecules confined in nanochannels. Phys. Rev. Lett. 94:1961011-1961014; Reccius, C. H., J. T. Mannion, J. D. Cross, and H. G. Craighead. 2005. Compression and free expansion of single DNA molecules in nanochannels. Phys. Rev. Lett. 95:2681011-2681014; Mannion, J. T., C. H. Reccius, J. D. Cross, and H. G. Craighead. 2006. Conformational analysis of single DNA molecules undergoing entropically induced motion in nanochannels. Biophys. J. 90:4538-4545).

There has also been a growing interest in using nanochannels to analyze single molecules with spatial resolution beyond the optical diffraction limit while benefiting from the advantages of established fluorescence spectroscopy techniques (Tegenfeldt, J. O., C. Prinz, H. Cao, S. Chou, W. W. Reisner, R. Riehn, Y. M. Wang, E. C. Cox, J. C. Sturm, P. Silberzan, and R. H. Austin. 2004. The dynamics of genomic-length DNA molecules in 100-nm channels. Proc. Natl. Acad. Sci. U.S.A. 101:10979-10983) and other methods (Tegenfeldt, J. O., O. Bakajin, C. F. Chou, S. S. Chan, R. Austin, W. Fann, L. Liou, E. Chan, T. Duke, and E. C. Cox. 2001. Near-field scanner for moving molecules. Phys. Rev. Lett. 86:1378-1381; Gordon, M. P., T. Ha, and P. R. Selvin. 2004. Single-molecule high-resolution imaging with photobleaching. Proc. Natl. Acad. Sci. U.S.A. 101:6462-6465; Thompson, R. E., D. R. Larson, and W. W. Webb. 2002. Precise nanometer localization analysis for individual fluorescent probes. Biophys. J. 82:2775-2783).

In this example, a method is described to quickly and precisely measure the conformation, length, speed and fluorescence intensity of single DNA molecules constrained by a nanochannel. DNA molecules were driven electrophoretically from a nanoslit into a nanochannel, as illustrated in FIG. 27A, which confined and dynamically elongated the molecules beyond their equilibrium length in a nanochannel. The stretched molecules were then transported through two spatially separated focal volumes, defined by lasers focused sequentially on the nanochannel, which enabled speed and cross correlation measurements (Tegenfeldt, J. O., O. Bakajin, C. F. Chou, S. S. Chan, R. Austin, W. Fann, L. Liou, E. Chan, T. Duke, and E. C. Cox. 2001. Near-field scanner for moving molecules. Phys. Rev. Lett. 86:1378-1381) and increased statistical validity and experimental throughput. The use of a nanochannel also reduced fluorescent background noise, increased excitation uniformity, and allowed single molecule detection at higher concentrations when compared to measurements made in larger fluidic channels or free solution (Foquet, M., J. Korlach, W. R. Zipfel, W. W. Webb, and H. G. Craighead. 2004. Focal volume confinement by submicrometer-sized fluidic channels. Anal. Chem. 76:1618-1626; Stavis, S. M., J. B. Edel, K. T. Samiee, and H. G. Craighead. 2005. Single molecule studies of quantum dot conjugates in a submicrometer fluidic channel. Lab Chip 5:337-343).

For each DNA molecule detected, photon bursts from the two fluorescent signals were matched and subsequently fit to analytical models describing the conformation, length, speed and intensity of the DNA strands. An example of the signals and fits resulting from the analysis of a DNA molecule interpreted as folded at the front end is shown in FIG. 27B. This analysis algorithm made possible a direct determination of molecular length and conformation with spatial resolution beyond the optical diffraction limit, established in the presented work at 114 nm, with an analysis time of 20 ms per molecule. The measurements depicted in FIG. 27B were also used to infer DNA length from total fluorescence burst intensity, a previously demonstrated analytical method (Foquet, M., J. Korlach, W. Zipfel, W. W. Webb, and H. G. Craighead. 2002. DNA fragment sizing by single molecule detection in submicrometer-sized closed fluidic channels. Anal. Chem. 74:1415-1422; Chou, H. P., C. Spence, A. Scherer, and S. Quake. 1999. A microfabricated device for sizing and sorting DNA molecules. Proc. Natl. Acad. Sci. U.S.A. 96), and the two methods were compared and combined. The confluence of these factors represents an important step forward toward applications that place a premium on spatial resolution and analysis time, such as single-molecule genomic sequencing.

The introduced methods were then used with the well-known system λ-bacteriophage DNA and its derivatives to study DNA fragmentation, folding, and dynamic stretching as a function of applied bias, and speed as a function of apparent length, folding and contour length. The results of these experiments help elucidate several aspects of the electrophoresis and friction of DNA molecules in nanoscale environments. DNA speed was found to increase slightly with folding, and stretching was found to increase with applied device bias and electric field. For mixtures of DNA fragments, speed was found to be almost constant with length, showing a slight decrease only for short fragments.

6.5.3 Theory, Methods and Materials

Single Molecule Burst Theory

The two collected photon count signals are generated by projecting the fluorescent images of individual DNA molecules moving in the nanochannel on two different optical fibers, which are connected to separate avalanche photodiodes. To describe the general signal shape, a DNA molecule with N base pairs and contour length L in a nanochannel with a depth and width D is considered. The strand is homogenously stained with $N_f$ fluorescent dye molecules giving a dye/basepair ratio $g=N_f/N$, and uniformly stretched to an end-to-end length $l_R=sL$, where s is the stretching factor ($0 \le s \le 1$). Folded molecules, as illustrated in FIG. 27A, are distinguished from unfolded molecules by one end of the strand showing a looped configuration, resulting in a higher fluorophore concentration along the length of the channel.

For an unfolded DNA molecule, the fluorophore concentration c can be written as a function of the position along the nanochannel axis x as:

$$c(x) = c_0[\Theta(x-x_0+l_R/2) - \Theta(x-x_0-l_R/2)] \quad (1)$$

where $\Theta(x)$ is the Heaviside step function, $x_0$ is the position of the center of the molecule, and $c_0 = Ng/(D^2 l_R)$ is the average fluorophore concentration inside the channel volume occupied by the DNA strand.

The DNA strand is illuminated by a focused (but not diffraction-limited) laser beam of power P and frequency v. Assuming a radial Gaussian shape with an $e^{-1/2}$ radius of $\sigma_R$, the laser intensity l(x,y) in the focal plane of the objective is:

$$I(x, y) = I_0 \exp\left(-\frac{x^2+y^2}{2\sigma_B^2}\right) \quad (2)$$

with amplitude $l_0 = k_{Ex}P/(2\pi\sigma_B^2)$ and with the factor $k_{Ex}$ used to account for dichroic absorption losses. The resulting fluorescence is collected by an objective of magnification m and imaged by the tube lens of the microscope on a fused silica fiber with diameter d. The investigated volume of the nanochannel is limited in the x direction from $-d/2m$ to $+d/2m$ by the fiber acting as an aperture and in the y and z directions to $-D/2$ to $D/2$ by the nanochannel. As $\sigma_B > d/m$ it is assumed that the DNA is illuminated by approximately constant laser intensity $l_o$ in all three dimensions, and since $d/m \gg D$ the calculation is reduced to one dimension. The number of emitted photons per channel length and time f(x) along the nanochannel x axis is therefore $$f(x) = f_0[\Theta(x-x_0+l_R/2) - \Theta(x-x_0-l_R/2)] \quad (3)$$

with an amplitude $f_0 = c_0 Q \varepsilon D^2 l_0/(h\nu)$, Planck's constant h, quantum yield Q, and the natural molar extinction coefficient of the dye $\varepsilon$. The resulting image at the fiber position is a convolution of f(x) with the intensity point spread function PSF(x) of the microscope objective and the tube lens which is modified to account for the objective magnification in:

$$i(x) = \frac{k_{Em}}{m} \int_{-\infty}^{+\infty} f(x') PSF(x/m - x') dx' \quad (4)$$

with the factor $k_{Em}$ accounting for the collection efficiency of the objective and absorption losses of the emission filters. Assuming a Gaussian point spread function with an $e^{-1/2}$ radius of $\sigma$:

$$PSF(x) = \frac{1}{\sqrt{2\pi}\,\sigma} \exp\left(-\frac{x^2}{2\sigma^2}\right) \quad (5)$$

the image can be described by:

$$i(x) = i_0 \frac{1}{2}\left[\mathrm{erf}\left(\frac{x/m - x_0 + l_R/2}{\sqrt{2}\,\sigma}\right) - \mathrm{erf}\left(\frac{x/m - x_0 - l_R/2}{\sqrt{2}\,\sigma}\right)\right] \quad (6)$$

with an amplitude $i_0 = k_{Em}f_0/m$. In the microscope image plane, the image is focused on an optical multimode fiber and transmitted to the photodiode. Fiber coupling and absorption losses reduce the resulting signal by a factor $k_{Fib}$. The number of photons per time $p(x_0)$ arriving at the detector is therefore $$p(x_0) = k_{Fib} \int_{-d/2}^{+d/2} i(x) dx = \frac{p_0 m}{d}\{pt(x_1) - pt(x_2) - [pt(x_3) - pt(x_4)]\} \quad (7)$$

with the signal amplitude $$p_0 = \frac{k_{Fib}k_{Em}f_0 d}{m} = \frac{k_{Fib}k_{Em}c_0 Q\varepsilon D^2 k_{Ex} Pd}{2\pi\sigma_B^2 m h\nu} \quad (8)$$

and the function parts (i=1, 2, 3, 4)

$$pt(x_i) = \frac{\sigma}{\sqrt{2\pi}} \exp\left(-\frac{x_i^2}{2\sigma^2}\right) + \frac{x_i}{2}\mathrm{erf}\left(\frac{x_i}{\sqrt{2}\,\sigma}\right) \quad (9)$$

and $x_{1/2} = x_0 - l_R/2 \pm d/(2m)$, $x_{3/4} = x_0 + l_R/2 \pm d/(2m)$.

This simple integration was made assuming that the step-index multimode optical fiber used has a collection efficiency with a pulse function lateral dependence.

The fluorophore concentration of a molecule with a folded front end can be described in a manner similar to the unfolded case. Inside the channel it occupies only an apparent length $l_A$, but its real end-to-end length $l_R$ can be calculated by adding the length of the folded over part $l_L$. The fluorophore concentration $c_{fold}$ can be written as $$c_{fold}(x) = c_0[\Theta(x-x_0+l_A/2) + \Theta(x-x_0-l_A/2+l_L) - 2\Theta(x-x_0-l_A/2)] \quad (10)$$

which leads to a photodiode signal:

$$p_{fold}(x_0) = \frac{p_0 m}{d}\{pt(x_1) - pt(x_2) + [pt(x_3) - pt(x_4)] - 2[pt(x_5) - pt(x_6)]\} \quad (11)$$

with $x_{1/2} = x_0 - l_A/2 \pm d/(2m)$, $x_{3/4} = x_0 + l_A/2 - l_L \pm d/(2m)$, and $x_{5/6} = x_0 + l_A/2 \pm d/(2m)$.

Higher orders of folding can be derived analogously.

In this example, two lasers were used to define two focal volumes along the length of the nanochannel, and two photodiodes were then used to image the DNA strand at two different positions x=0 and x=sd. The time-dependent signals can then be described by $p(v_S(t-t_0))$ and $p(v_S(t-t_0)-sd)$ respectively with $t_0$ being the time when the center of the molecule is at x=0 and $v_S$ being the speed of the strand. It is assumed that different apparent DNA lengths ($l_{41}$, $l_{42}$) and amplitudes ($p_{01}$, $p_{02}$) are possible at x=0 and x=sd due to changes in molecular conformation and different optical loss factors.

Cross-Correlation Theory

By analyzing the cross correlation function of the two measured fluorescent signals, Fluorescence Correlation Spectroscopy (FCS) provides time-averaged information about the sample (Elson, E. L. and D. Magde. 1974. Fluorescence Correlation Spectroscopy Conceptual Basis and Theory. Biopolymers 13:1-27; Magde, D., W. W. Webb, and E. Elson. 1972. Thermodynamic Fluctuations in a Reacting System—Measurement by Fluorescence Correlation Spectroscopy. Phys. Rev. Lett. 29:705-708; Magde, D., E. L. Elson, and W. W. Webb. 1974. Fluorescence Correlation Spectroscopy Experimental Realization. Biopolymers 13:29-61). A modified FCS approach is used in this example to yield the average speed and length of DNA strands, which is then used to guide the subsequent single molecule burst analysis algorithms. The cross correlation function is known to be $$G_C(\tau) = 1 + \frac{\int\int W_1(x)W_2(x')\rho(x, x', \tau)dxdx'}{\overline{C}^2 \int W_1(x)dx \int W_2(x')dx'}. \quad (12)$$

with the molecular fluorescence detection efficiency (MDE) functions $W_1(x)=W(x)$ and $W_2(x)=W(x-sd)$ of the two focal volumes, the concentration fluctuation function $\rho(x,x',\tau)$ and the mean concentration $\overline{C}$ (Brinkmeier, M., K. Dorre, J. Stephan, and M. Eigen. 1999. Two beam cross correlation: A method to characterize transport phenomena in micrometer-sized structures. Anal. Chem. 71:609-616).

A sample consisting of unfolded DNA molecules of a single length $l_C$ is assumed. For the velocities $v_C$ used for high speed analysis, diffusion can be neglected (Foquet, M., J. Korlach, W. R. Zipfel, W. W. Webb, and H. G. Craighead. 2004. Focal volume confinement by submicrometer-sized fluidic channels. Anal. Chem. 76:1618-1626) and the concentration fluctuation function becomes $\rho(x,x',\tau)= \overline{C}\delta(x-x'-v_C\tau)$ (Magde, D., W. W. Webb, and E. L. Elson. 1978. Fluorescence Correlation Spectroscopy. 3. Uniform Translation and Laminar-Flow. Biopolymers 17:361-376).

As the stretched DNA strands are longer than the investigated channel length ($l_C$>d/m), $W(x)$ becomes equal to $p(x)$ from Eq. 7. To analytically solve the integrals in Eq. 12, $W(x)$ is approximated by a modified sigmoidal function which matches the slopes of $p(x)$ at $x=\pm l_C/2$:

$$W(x) = p_0\left[1 - \frac{1}{1 + \exp(-4\ m/d(|x| - l_C/2))}\right] \quad (13)$$

The result for $G_C(\tau)$ was derived analytically using Mathematica (Wolfram Research, Champaign, Ill.) according to methods known in the art (data not shown).

As $G_C(\tau)$ varies between experimental runs due to folding and fragmentation of the sample, cross correlation fits were imperfect but adequate to guide the subsequent single molecule analysis algorithm. The quality of cross correlation fits will improve as smaller nanochannels are used to reduce folding of the DNA molecules.

Single-Molecule Burst Analysis

The analysis algorithm for the two photon count signals consisted of the localization of bursts of fluorescence resulting from the detection of DNA molecules, the matching of corresponding bursts in both photon count signals and the combined fitting of the corresponding bursts. Partner bursts were analyzed simultaneously to enable the most sensitive determination of molecular speed from the time of travel between the two focal volumes, as well as from both individual bursts. Analysis parameters were modified with varying device bias and resulting molecular speed. The following parameter ranges correspond to device biases, U, of 1V-100V. The photon count signals were originally recorded at a bin time of 10 µs and then rebinned to 10 µs-500 µs in order to improve and accelerate analytic burst fitting. Rebinning was limited to preserve the shape of each fluorescent burst. All bursts in both signals were localized by the use of a thresholding algorithm. Single-molecule detection thresholds were set at least seven standard deviations above the mean background noise values, which were determined by Poisson fitting the overall photon count distributions of the two signals to Poisson distributions. This eliminated virtually all noise from inadvertent analysis Multiple bursts separated by $\Delta t_{Gap}$-10 ms-0.1 ms were combined into one burst. The results of the cross correlation analysis were used to find matching bursts.

For a burst in the first photon count signal at time $t_0$, the matching burst in the second signal was defined as the burst closest to the time $t_0+t_P$, with $t_P=sd/v_C$ being the peak position of the cross correlation curve. A burst was considered for further analysis only if a corresponding burst was found between $t_1=t_0+t_P-\Delta t_P$ and $t_2=t_0+l_P+\Delta t_P$ with $\Delta t_P=(d+l_C)/v_C$. In the case of a heterogeneous sample the correlation curves were not fitted, and the values for $t_P$ and $\Delta t_P$ were chosen manually from the cross correlation curve.

Partner bursts were fitted simultaneously using a modified Levenberg-Marquard algorithm. Six different folding models based on observations of existing burst shapes were used to account for up to three levels of molecular folding. The level of folding was determined by comparing the maximum photon count of the first partner burst to the maximum of the photon count distribution for all bursts in the measurement, neglecting the signal slopes at the beginning and end of the bursts.

This distribution maximum was assumed to be the average photon count resulting from the detection of unfolded DNA strands wholly in the focal volume, and was assigned as the amplitude $p_{0,1}$ of the fitting formula for channel 1. The fitting amplitude $p_{0,2}$ for channel 2 was chosen analogously. Fitting amplitudes were fixed to analyze the bursts correctly. It was only in the case of very slow moving molecules and experimental run times exceeding 2 min (corresponding to a device bias of U=1-2V) that individually fitting the burst amplitudes for each molecule gave better results. This accounted for increasing residence times in the nanoslit, and a resulting increase in dye loss to the nanoslit surfaces, as well as photobleaching from scattered light near the nanochannel array.

If a molecule was assumed to be folded two or three times, two fitting models were compared and the one yielding a lower $\chi^2$ was chosen. The photon count per molecule was determined by summing the counts between the start and end times of the pulse. These times were determined by the fitting algorithm, and not the thresholding algorithm, to increase their accuracy. This analysis was performed using custom software programmed in Labview (National Instruments, Austin, Tex.) which allowed correction of the automatically chosen model for every fit.

Figure 33:
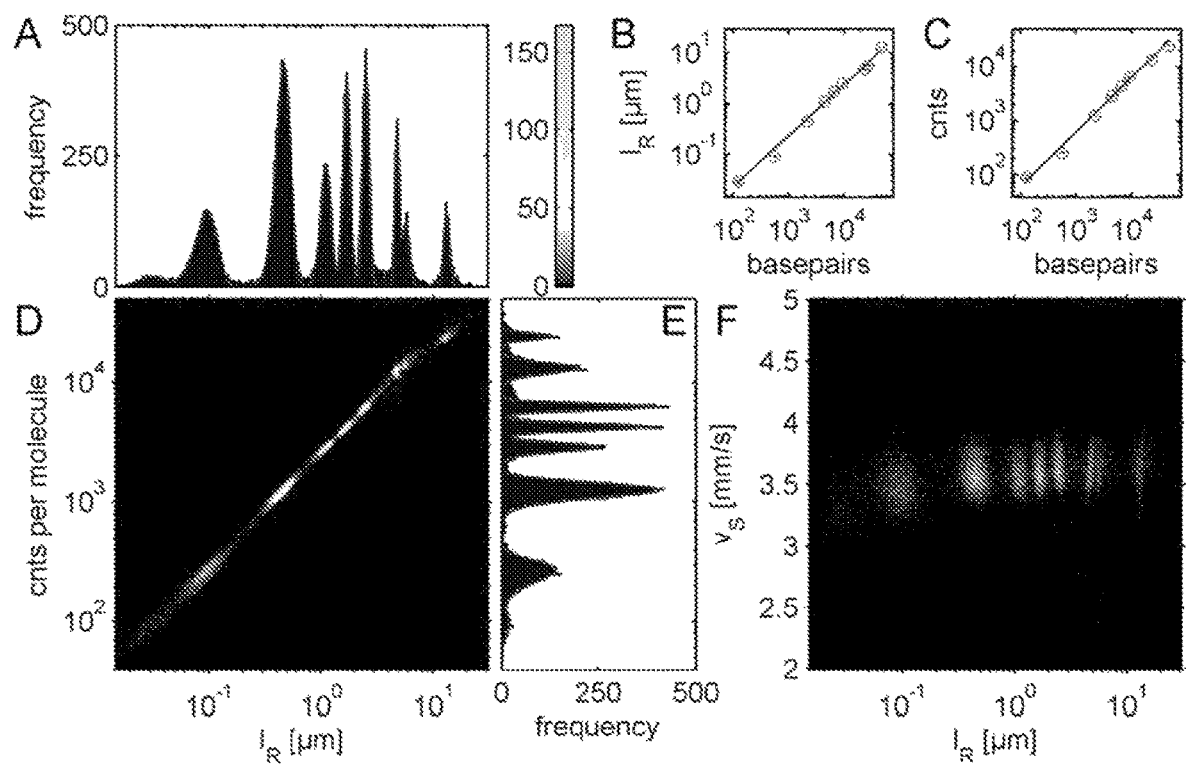

A small number of detection events showing overlapping molecules or molecular laser damage were excluded from further analysis in all measurements, except for the one shown in FIG. 33 having over 16,000 molecules. Bursts from overlapping molecules were identified by the superposition of burst shapes of the type shown in FIG. 29B. Photodamage was observed as a single photon burst from an intact molecule in the first focal volume, followed by two photon bursts from fragments in the second focal volume. Occasionally, the second burst remained intact but showed a partial decrease in fluorescence intensity.

Gaussian Fitting of Logarithmic Distributions

In the experimental results shown in FIGS. 33A-F, the DNA length varied over 2.6 orders of magnitude, and therefore the color coded plot (shown in grayscale in FIG. 33D) as well as the distributions in FIGS. 33A and 33E were binned logarithmically. For FIG. 33A it was assumed that each of the real length peaks is Gaussian. Peak i can then be described as $f_i(l_R) = a_{Ri} \exp[(l_R - l_{Ri})^2 / 2\sigma_{Ri}^2]$ with amplitude $a_{Ri}$, mean value $l_{Ri}$ and standard deviation $\sigma_{Ri}$. Logarithmic binning with bin size dy of this curve leads to:

$$f_{logi}(l_R) = \int_{r_1}^{r_2} f_i(l'_R) dl'_R \quad (14)$$

$$= \sqrt{\pi/2}\, a_{Ri} \sigma_{Ri} \left[ \mathrm{Erf}\left( \frac{-10^{-dy/2} l_R + l_{Ri}}{\sqrt{2}\, \sigma_{Ri}} \right) - \mathrm{Erf}\left( \frac{-10^{dy/2} l_R + l_{Ri}}{\sqrt{2}\, \sigma_{Ri}} \right) \right]$$

using the integration boundaries $r_1 = 10^{(\log_{10}(l_R) - dy/2)}$ and $r_2 = 10^{(\log_{10}(l_R) + dy/2)}$. A superposition of nine functions of this type was used to fit the real length distribution in FIG. 33A, and the photon count distribution in FIG. 33E was fit in an analogous manner.

Optical Setup

An Olympus IX71 inverted microscope (Olympus, Melville, N.Y.) with a Prior Pro-Scan II stage (Prior Scientific, Rockland, Mass.) was used in conjunction with nanochannel devices for single molecule detection. The microscope stage was equipped with integrated position sensors and servo motors to control lateral drift, and drift in the focal plane was measured using a stage height probe (Heidenhain, Traunreut, Germany) and controlled with an external focus servo motor (Prior Scientific). An argon-krypton mixed gas tunable laser (Melles Griot Laser Group, Carlsbad, Calif.) and a solid state sapphire laser (Coherent, Santa Clara, Calif.) were used with Z488/10X excitation filters (Chroma Technology, Rockingham, Vt.) for fluorescence excitation at 488 nm. A variety of optical elements including mirrors and kinematic mounts (Newport, Irvine, Calif.) were used to guide the laser beams into the microscope, with their entry angles tuned to yield focal volumes separated along the length of the nanochannel by 11-12 μm. Both lasers were tuned to have a power of 250 μW, as measured after the circular polarizer, except in the experiment shown in FIGS. 33A-F in which the laser power was 1.5 mW.

Figure 28:
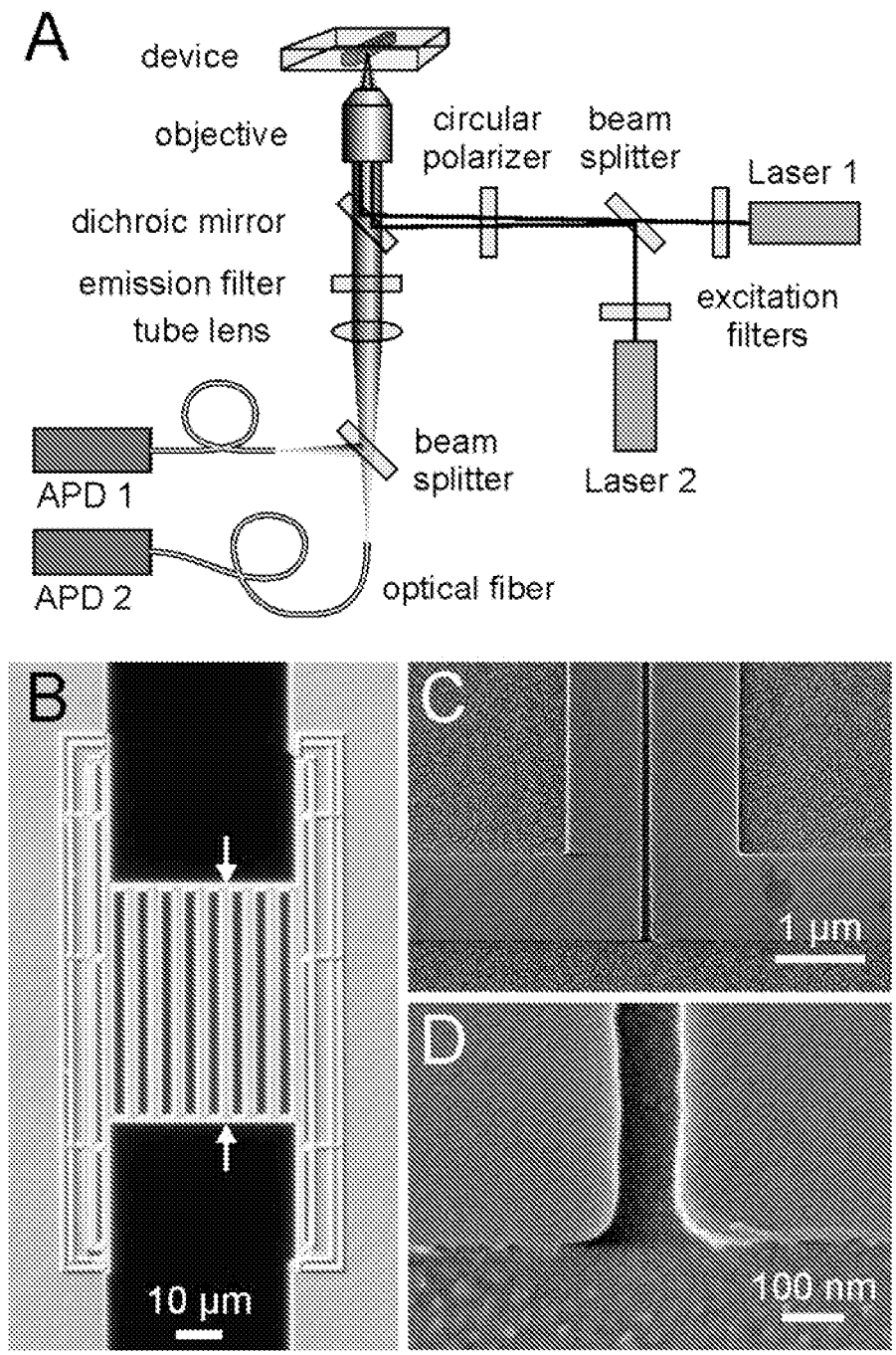

A Z488RDC dichroic mirror (Chroma) reflected the laser beams into the back of a UApo/340 water immersion objective (40×, 1.15 NA, Olympus). Collected fluorescence emission passed through a 535AF45 emission filter (Omega Optical, Brattleboro, Vt.). The signal was divided using a beam splitter (Omega) and focused by the internal tube lens of the microscope on two high power step index fused silica multimode optical fibers (50 μm inner diameter, 125 μm cladding diameter, OZ Optics Limited, Ottawa, ON, Canada). At the end of the fibers light was detected with two avalanche SPCM-AQR-14-FC photodiodes (Perkin Elmer, Fremont, Calif.). An overview of the optical setup is shown in FIG. 28A. A Photometrics Cascade 512B camera (not shown in FIG. 28A, Photometrics, Tucson, Ariz.) was used to align the focused lasers to the nanochannel, visualize the experiment and image several hundred quantum dots (Qdot 525 streptavidin conjugate, Invitrogen, Carlsbad, Calif.) adsorbed to a fused silica coverslip for characterization of the point spread function of the microscope objective. The point spread function was described by a Gaussian with a standard deviation of $\sigma = 140 \pm 20$ nm. Further details of the optical setup can be found in Stavis, S. M., J. B. Edel, Y. G. Li, K. T. Samiee, D. Luo, and H. G. Craighead. 2005. Single-molecule mobility and spectral measurements in sub-micrometer fluidic channels. J. Appl. Phys. 98:449031-449035.

Device Fabrication

Nanochannels were fabricated in fused silica using a combination of electron beam and optical lithography. A 150 nm thick film of poly(methyl-methacrylate) resist was spun onto a 500 μm thick substrate wafer (Mark Optics, Santa Ana, Calif.) followed by an evaporated 25 nm thick film of gold. A negative device pattern was exposed using a JBX-9300FS electron beam lithography system (JEOL, Peabody, Mass.). After removal of gold and development of the resist, the nanochannel pattern was transferred to a chromium mask by evaporation and liftoff. A microchannel etch mask was patterned using standard optical lithography procedures and the same liftoff process. An optical micrograph of the resulting chromium mask can be seen in FIG. 28B. The micro- and nanochannels were then simultaneously etched into the substrate using a Plasmalab 80Plus RIE (Oxford Instruments, Eynsham, UK) with a $CHF_3/O_2$ mixture. FIGS. 28C and 2D are electron micrographs showing the interface between the microchannel and a nanochannel. Inlet and outlet holes were excised from the substrate by alumina powder blasting through the backside of the wafer. To enclose the channels, a 170 μm thick fused silica cover wafer (Mark Optics) was bonded and annealed at a temperature of 1050° C. to the substrate wafer. Following device fabrication, sample reservoirs were glued to the inlet and outlet holes and sealed with reusable adhesive during use. Platinum wires provided electrical contacts with the sample solutions. Further details of the fabrication process can be found in Mannion, J. T., C. H. Reccius, J. D. Cross, and H. G. Craighead. 2006. Conformational analysis of single DNA molecules undergoing entropically induced motion in nanochannels. Biophys. J. 90:4538-4545.

Samples

DNA samples were labeled using the bis-intercalating fluorescent dye YOYO-1 (Invitrogen) with a dye to base pair ratio of 1 to 5. λ-bacteriophage DNA (New England Biolabs, Ipswich, Mass.) at a concentration of 25 μg/mL was heated to a temperature of 65° C. for 5 min and added to a mixture of YOYO-1 dye in 5× Tris-Borate-EDTA buffer (TBE, pH 8.3, Sigma-Aldrich, St. Louis, Mo.) with 6% (v/v) B-mercaptoethanol (Sigma-Aldrich) as an antiphotobleaching reagent. A HindIII digest of λ-bacteriophage DNA (New England Biolabs) was prepared in a similar manner with the exception that it was heated to 60° C. The digest was mixed in equal parts with pure λ-bacteriophage at a total concentration of 50 μg/mL, with the appropriate heating temperature used for each constituent before mixing. The sample was then labeled with YOYO-1. In this case the buffer also contained 1% (w/w) poly(n-vinylpyrrolidone) (PVP, molecular mass 40 kD, Sigma-Aldrich) to reduce both electroosmotic flow and nonspecific binding of DNA to channel walls (38-40). The contour length of λ-bacteriophage DNA (48.5 kbp) can be calculated from the basepair spacing of 0.34 nm to be $L_\lambda=16.5$ μm. Recent studies have shown that the dye TOTO-1, which is similar to YOYO-1, increases the contour length $L_\lambda$ by 30-35% at a dye/basepair ratio of 1:4 (Bakajin, O. B., T. A. J. Duke, C. F. Chou, S. S. Chan, R. H. Austin, and E. C. Cox. 1998. Electrohydrodynamic stretching of DNA in confined environments. Phys. Rev. Lett. 80:2737-2740; Perkins, T. T., D. E. Smith, R. G. Larson, and S. Chu. 1995. Stretching of a single tethered polymer in a uniform flow. Science 268:83-87). $L_\lambda$ is therefore expected to rise by 23% to 20 μm for a dye ratio of 1:5.

Autocorrelation Function

The normalized one-dimensional autocorrelation function $G_{AC}(\tau)$ is defined as:

$$G_{AC}(\tau) = 1 + \frac{\int\int W(x)W(x')\rho(x, x', \tau)dxdx'}{\overline{C}^2(\int W(x)dx)^2}. \quad (S\text{-}1)$$

with the concentration fluctuation function ρ(x,x',τ) and the Molecular Detection Efficiency (MDE) function W(x). For stretched out DNA molecules flowing at high speed through a nanofluidic channel upon which a laser is focused we assume $\rho(x,x',\tau)=\overline{C}\delta(x-x'-v)$ and:

$$W(x) = p_0\left[1 - \frac{1}{1+\exp(-4\ m/d(|x|-l/2))}\right] \quad (S\text{-}2)$$

The MDE uses a modified sigmoidal function to describe the detection of long DNA molecules flowing through a region of uniform excitation intensity. This constant excitation profile approximates the result of the optical fiber imaging only the central section of a focused but non-diffraction limited laser spot described by a broad Gaussian. FIG. 34 shows a comparison between the MDE p(x) from Eq. 7 above and its much simpler replacement W(x) from Eq. S-2.

We also define the three time constants $t_1=d/(mv)$, $t_2=sd/v$ and, $t_3=L/v$. As a result we obtain:

$$G_{AC}(\tau)-1=G_0 z_{A1}/n_{A1} \quad (S\text{-}3)$$

with the prefactor:

$$G_0 = \lim_{\tau \to 0}(G_A(\tau)-1)$$

$$= \frac{t_1}{t_3}\left[2\ln\left(1+e^{\frac{2t_3}{t_1}}\right)-\right.$$

$$\left.\tanh\left(\frac{t_3}{t_1}\right)-1\right] \bigg/ 4\overline{C}l\left[1+\frac{t_1}{2t_3}\ln\left(1+e^{-\frac{2t_3}{t_1}}\right)\right]$$

and the numerator:

$$z_{A1} = \left(1+e^{\frac{2t_3}{t_1}}\right)\left[\frac{2\tau}{t_1}\left(2e^{\frac{8\tau}{t_1}}-e^{\frac{4t_3}{t_1}}-e^{\frac{4(t_3+\tau)}{t_1}}\right)+\right.$$

-continued $$\left(e^{\frac{4\tau}{t_1}}+e^{\frac{4(t_3+\tau)}{t_1}}-2e^{\frac{4t_3}{t_1}}\right)\ln\left(1+e^{\frac{2t_3}{t_1}}\right)++\left(e^{\frac{4t_3}{t_1}}-e^{\frac{8\tau}{t_1}}\right)\ln\left(e^{\frac{2t_3}{t_1}}+e^{\frac{4\tau}{t_1}}\right)\right]$$

and denominator:

$$n_{A1} = \left(e^{\frac{4t_3}{t_1}}+e^{\frac{4\tau}{t_1}}\right)\left(-1+e^{\frac{4\tau}{t_1}}\right)\left[-e^{\frac{2t_3}{t_1}}+\left(1+e^{\frac{2t_3}{t_1}}\right)\ln\left(1+e^{\frac{2t_3}{t_1}}\right)\right].$$

Cross-Correlation Function

The normalized one-dimensional cross-correlation function $G_{CC}(\tau)$ can be written as:

$$G_{CC}(\tau) = 1 + \frac{\int\int W_1(x)W_2(x')\rho(x, x', \tau)dxdx'}{\overline{C}^2\int W_1(x)dx\int W_2(x')dx'}. \quad (S\text{-}4)$$

with the concentration fluctuation function ρ(x,x',τ) and the MDE functions $W_1(x)$ and $W_2(x)$ describing the sequential detection of DNA molecules. For stretched out DNA molecules flowing at high speed through a nanofluidic channel upon which two lasers are focused and separated by a distance sd we assume $\rho(x,x',\tau)=\overline{C}\delta(x-x'-v)$, $W_1(x)=W(x)$ and $W_2(x)=W(x-sd)$. As a result we obtain:

$$G_{CC}(\tau)-1 = \begin{cases} k_C z_{C1}/n_{C1} & \text{for } \tau > sd/v \\ k_C z_{C2} & \text{for } \tau = sd/v \\ k_C z_{C3}/n_{C3} & \text{for } \tau < sd/v \end{cases} \quad (S\text{-}5)$$

with the prefactor:

$$k_C = \left\{\overline{C}l\left[1+\frac{t_1}{2t_3}\ln\left(1+e^{-\frac{2t_3}{t_1}}\right)\right]\ln\left(1+e^{\frac{2t_3}{t_1}}\right)\right\}^{-1}$$

the numerators:

$$z_{C1} = \frac{2(\tau-t_2)}{t_1}e^{\frac{4(t_2+t_3+\tau)}{t_1}} - \frac{4\tau}{t_1}e^{\frac{8\tau}{t_1}} +$$

$$\frac{2(t_2+\tau)}{t_1}e^{\frac{4(2t_2+t_3)}{t_1}}++e^{\frac{4t_2}{t_1}}\left(2e^{\frac{4(t_2+t_3)}{t_1}}-e^{\frac{4\tau}{t_1}}-e^{\frac{4(t_3+\tau)}{t_1}}\right)\ln\left(1+e^{\frac{2t_3}{t_1}}\right)-$$

$$\left(e^{\frac{4(2t_2+t_3)}{t_1}}-e^{\frac{8\tau}{t_1}}\right)\ln\left(e^{\frac{2(2t_2+t_3)}{t_1}}+e^{\frac{4\tau}{t_3}}\right)$$

$$z_{C2} = \left(1+e^{\frac{2t_3}{t_1}}\right)^{-1}+\ln\left(1+e^{\frac{2t_3}{t_1}}\right)-1$$

$$z_{C3} = \frac{2t_2}{t_1}e^{\frac{4(t_2+t_3+\tau)}{t_1}} - \frac{4t_2}{t_1}e^{\frac{8t_2}{t_1}} + \frac{2t_2}{t_1}e^{\frac{4(t_3+2\tau)}{t_1}} -$$

$$\frac{2\tau}{t_1}e^{\frac{4(t_2+t_3+\tau)}{t_1}}\frac{2\tau}{t_1}e^{\frac{4(t_3+2\tau)}{t_1}}++e^{\frac{4t}{t_1}}\left(-e^{\frac{4t_2}{t_1}}-e^{\frac{4(t_3+2\tau)}{t_1}}+2e^{\frac{4(t_3+\tau)}{t_1}}\right)$$

$$\ln\left(1+2e^{\frac{2t_3}{t_1}}\right)+\left(e^{\frac{8t_2}{t_1}}-e^{\frac{4(t_3+2\tau)}{t_1}}\right)\ln\left(e^{\frac{4t_2}{t_1}}+e^{\frac{2(t_3+2\tau)}{t_1}}\right)$$

and the denominators:

$$n_{C1} = \left(e^{\frac{4t_2}{t_1}}-e^{\frac{4\tau}{t_1}}\right)\left(e^{\frac{4(t_2+t_3)}{t_1}}-e^{\frac{4\tau}{t_1}}\right)$$

-continued $$n_{C2} = \left(e^{\frac{4t_2}{t_1}} - e^{\frac{4\tau}{t_1}}\right)$$

$$n_{C3} = \left(e^{\frac{4t_2}{t_1}} - e^{\frac{4\tau}{t_1}}\right)\left(e^{\frac{4t_2}{t_1}} - e^{-\frac{4(t_3+\tau)}{t_1}}\right).$$

6.5.4 Results and Discussion

This example demonstrates a method to dynamically elongate, rapidly detect and carefully analyze single DNA molecules in a nanofluidic channel. This example also demonstrates the use of this method to investigate some of the physical phenomena occurring when DNA strands are manipulated in this manner, including speed as a function of folding, stretching and speed as a function of electric field, and speed as a function of length. Several experiments were conducted using variations of the well known system, λ-bacteriophage DNA, including random fragments thereof and controlled fragments from a mixture of λ-bacteriophage DNA with its own HindIII digest.

Length Analysis of Single λ-Bacteriophage DNA Molecules

Each experimental run yielded two photon count signal traces as well as their cross correlation function. Bursts of fluorescence in the two photon count signals were identified by a thresholding algorithm. Corresponding partner bursts were matched by estimating the time window of their occurrence based on preceding fits of the cross correlation function, yielding estimates for the speed $v_C$ and average apparent length $l_C$ of the molecules. The majority of bursts exhibited multiple levels of fluorescence intensity, which were interpreted as the result of folded DNA molecules. The observed burst shapes are similar to the electrical current changes observed during DNA translocation through artificial nanopores (Li, J. L., M. Gershow, D. Stein, E. Brandin, and J. A. Golovchenko. 2003. DNA molecules and configurations in a solid-state nanopore microscope. Nat. Mater. 2:611-615; Chen, P., J. J. Gu, E. Brandin, Y. R. Kim, Q. Wang, and D. Branton. 2004. Probing single DNA molecule transport using fabricated nanopores. Nano Lett. 4:2293-2298). An example of this phenomenon is shown in FIG. 27B.

Almost all molecules exhibited some degree of front end folding, which was also observed in previous experiments involving single DNA molecules in nanochannels (Reccius, C. H., J. T. Mannion, J. D. Cross, and H. G. Craighead. 2005. Compression and free expansion of single DNA molecules in nanochannels. Phys. Rev. Lett. 95:2681011-2681014; Mannion, J. T., C. H. Reccius, J. D. Cross, and H. G. Craighead. 2006. Conformational analysis of single DNA molecules undergoing entropically induced motion in nanochannels. Biophys. J. 90:4538-4545), but to a lesser degree. The increased difference in the electric field strength between the nanoslit and the nanochannel in the device used here is a likely cause for this increased front end folding. It is hypothesized that the large electric field gradient leads to the random entrance of whatever part of the DNA molecule first comes close enough to the nanochannel, despite the higher entropic forces hindering the entrance of looped structures into the channels. The metaphor of "sucking spaghetti" (Austin, R. 2003. Nanopores—The art of sucking spaghetti. Nat. Mater. 2:567-568) helps explain why folding is rarely observed in the middle or at the end of the molecules, which are stretched out at these locations. There are several other possible explanations for the observed front end folding. For the high speeds used in these experiments, molecules may become folded inside the channel due to hydrodynamic effects or interactions with the channel surface. Elongation and folding caused by interactions with the nanoslit surfaces before entrance into the nanochannel is possible, and interactions with the nanochannel surfaces could also lead to a compression of the leading strand end. None of these alternative explanations were observed at lower speeds (Mannion, J. T., C. H. Reccius, J. D. Cross, and H. G. Craighead. 2006. Conformational analysis of single DNA molecules undergoing entropically induced motion in nanochannels. Biophys. J. 90:4538-4545); and the long persistence length of DNA as well as the existence of quantized burst shapes including 3, 6 and 7 in FIG. 29 makes compression unlikely, which is why the folding interpretation was preferred in this example. A mixture of the mentioned effects is also possible, and in this case molecules with a short initial peak could be modeled by a modified version of Eq. 10 using a variable initial step height. This would lead to fitting functions with shapes that differ from those used here only by different slopes in the leading signal edge. As analysis of the slopes is currently limited by fluctuations in fluorescence, the results for the real length will be very close to the current results here.

Based on these observations, seven theoretical molecular conformations were used to describe up to three levels of front end folding, as shown in FIG. 29A. For two and three folds, respectively, two and three conformations exist which differ in the length of the folded section of a molecule relative to neighboring nonfolded ends, when considering the molecule from right to left. Using these seven molecular conformations, six analytical models denominated as α-ζ were developed to fit measured fluorescence bursts. Differentiation of the fluorescence burst models comes from the mathematical description of the resulting fluorophore concentration profiles along the channel axis. For two folds, the apparent length of the molecules can be dominated either by the single strand end or by the loop, leading to different fluorophore concentration levels. The length of the next concentration level is then described as a fraction of the apparent length. For three folds, the apparent length of the molecules can again be dominated either by a single strand end or by the loop, leading to two different models. The lengths of the two left shapes are both dominated by the single strand end, enabling them to be described by the same model ε. Almost all single molecule detection events in the example here could be described by these various models. Several examples of fluorescent bursts, corresponding molecular conformations and analytical fits are shown in FIG. 29B. While the fluorescence intensity was quite constant in the unfolded regions, as seen in burst shape 1, super-Poissonian signal fluctuations were still evident. This indicates that although the molecules were uniformly stretched, they were not fully elongated to their contour length, resulting in strand density fluctuations. For each DNA molecule investigated, a fitting model was selected based on burst height, and the two partner bursts were fitted together. An unfolded molecule, for example, was fitted with the function $p(v_s(t-t_0))+p_{Off1}$ for signal 1 and $p(v_s(t-t_0)-sd)+p_{Off2}$ for signal 2, both based on the function $p(x_0)$ of Eq. 7. For a molecule with a single front end loop, $p_{fold}(v_s(t-t_0))+p_{Off1}$ was used to fit signal 1 and $p_{fold}(v_s(t-t_0)-sd)+p_{Off2}$ was used to fit signal 2, both based on Eq. 11.

Analogous functions were created and used for higher degrees of folding. In all cases, the fitting parameters included the speed $v_S$, the apparent lengths $l_{A1}$ and $l_{A2}$ resulting from the two signals, and the initial burst time $t_0$.

Previously determined parameters such as the laser spot distance sd, fiber diameter d, objective magnification m, background noise levels $p_{Off1}$ and $p_{Off2}$ for the two signals, and the Gaussian radius of the point spread function σ were kept constant for all fits. The signal amplitude prefactors $p_{0,1}$ and $p_{0,2}$ for the two signals were generally kept constant. For analysis times longer than two minutes, the prefactors were fitted to account for dye loss and photobleaching effects in the nanoslit. Depending on the degree of folding, additional folding factors were also fitted, such as $f_a=l_{L1}/l_{A1}=l_{L2}/l_{A2}$ for a molecule with a single fold. It was assumed that the folding factors for both signals were constant for this experiment, while changes in apparent length ($l_{A1}$, $l_{A2}$) and folded over (looped) length ($l_{L1}$, $l_{L2}$) were possible. Due to slightly different optical fiber alignments, the two signals gave molecule lengths differing up to 10%, and the higher average length was selected, as the smaller value was assumed to arise from a slight misalignment of that optical fiber. An actual variation of the strand length between the two detection volumes was unlikely as length changes were expected to happen on a timescale of 10 s (Mannion, J. T., C. H. Reccius, J. D. Cross, and H. G. Craighead. 2006. Conformational analysis of single DNA molecules undergoing entropically induced motion in nanochannels. Biophys. J. 90:4538-4545).

752 intact λ-bacteriophage molecules were detected in three similar experiments with a device bias of 50V. Bursts of fluorescence described by the β, γ, and ε folding models were observed most often (33%, 46% and 20%. respectively) while only 1% of observed bursts were described by the other models. The automated fitting algorithm selected the δ fitting model for short fragments only, while the γ fitting model would have also worked, and never for intact λ-bacteriophage molecules. The eighth burst shape in FIG. 29B is shown as an example of a rare detection event which was not described fully by one of the six basic models shown in FIG. 29A. Model β came closest to describing the shape of the burst in this case, which could have been caused by overlapping molecules, a fold or a knot. A similar phenomenon was observed previously (Mannion, J. T., C. H. Reccius, J. D. Cross, and H. G. Craighead. 2006. Conformational analysis of single DNA molecules undergoing entropically induced motion in nanochannels. Biophys. J. 90:4538-4545); in this earlier study, a knot was detected in a DNA molecule undergoing entropic recoil from a nanochannel, which did not dispel over time as a simple fold would have. Although this detection event shows a limitation of the models used to fit the bursts of fluorescence, it is also an illustration of the ability in a single molecule measurement to detect rare species or transient events.

FIGS. 30A-F shows the results of a one minute experiment in which 416 molecules from a λ-bacteriophage DNA sample were detected. The definitions of the different lengths used to describe a folded DNA strand with a single loop are shown in FIG. 30C. The apparent length $l_A$ neglects any folding of the strand and is determined by analyzing only the start to end length of the DNA strand. The apparent length is of interest as it enables a more direct comparison of the results presented here with other methods of DNA analysis, including translocation of DNA through nanopores and hydrodynamic stretching. The looped length $l_L$ is the length of the folded over segment of DNA, and the real length $l_R$ is the sum of the apparent and looped lengths. The free length $l_F$ describes the section of DNA that is not folded over. While the apparent length could also be determined by a simple thresholding algorithm, the other length values result only from fitting the burst shapes.

A comparison of these different length values is shown in FIGS. 30A and 30B. The distribution of real lengths in FIG. 30B shows a much sharper peak, corresponding to intact λ-bacteriophage DNA molecules, than the apparent length distribution in FIG. 30A. Based on analysis accounting only for apparent length, many molecules in this distribution appear to be fragments. When the real length is calculated, however, the molecules are found instead to be intact and folded, correcting the distribution. This is readily observed when the number of photons collected from each molecule is plotted against the apparent length (FIG. 30D) and the real length (FIG. 30E) of the molecules. Although the apparent length distribution of molecules in FIG. 30D is widely scattered, the real length distribution in FIG. 30E is focused and fit to a single line. The sample also contained a small fraction of λ-DNA multimers which were observed at higher photon counts and with longer length than visualized in FIGS. 30A-F. The distributions of the photon count per molecule and of the real length can be fitted with Gaussians yielding a mean photon count of 48,000±2,000 photons and a real length of 10.7±0.3 μm for intact λ-bacteriophage DNA molecules. This is longer than the equilibrium length of 7-8 μm measured for λ-bacteriophage molecules in 100 nm×200 nm channels (Tegenfeldt, J. O., C. Prinz, H. Cao, S. Chou, W. W. Reisner, R. Riehn, Y. M. Wang, E. C. Cox, J. C. Sturm, P. Silberzan, and R. H. Austin. 2004. The dynamics of genomic-length DNA molecules in 100-nm channels. Proc. Natl. Acad. Sci. U.S.A. 101:10979-10983; Reccius, C. H., J. T. Mannion, J. D. Cross, and H. G. Craighead. 2005. Compression and free expansion of single DNA molecules in nanochannels. Phys. Rev. Lett. 95:2681011-2681014), which is expected, as the measured value is not the equilibrium length, but rather the dynamically stretched length.

This stretching effect was previously found for T4-bacteriophage DNA molecules entering nanochannels. The ensuing relaxation showed a time constant of 9.3 s (Mannion, J. T., C. H. Reccius, J. D. Cross, and H. G. Craighead. 2006. Conformational analysis of single DNA molecules undergoing entropically induced motion in nanochannels. Biophys. J. 90:4538-4545). The relative standard deviation of the Gaussian fits was found to be smaller for the real length distribution than for the photon count distribution (3.1% versus 4.7%). All molecules within two standard deviations of the mean photon count and the mean real length were assumed to be intact λ-bacteriophage DNA molecules (black arrows mark region in FIG. 30D), which accounts for 52% of all molecules detected. Assuming that the rest of the smaller molecules were fragments of λ-bacteriophage DNA molecules, and neglecting the few λ-bacteriophage concatemers detected, the sum of the length of these fragments divided by the mean real length of λ-bacteriophage DNA gives 60 as the original number of intact molecules.

The percentage of intact strands was then calculated to be 78%, which is somewhat lower than the 86% of intact λ-bacteriophage DNA molecules as determined by agarose gel electrophoresis. This measurement was performed by the manufacturer using samples from the same lot, and the resulting fluorescence image was analyzed with a rolling ball background correction using Image J (National Institute of Mental Health, Bethesda, Md.), a Gaussian distribution to model the spatially averaged intensity of the DNA band, and a range of two standard deviations around the mean to differentiate intact molecules from fragments. Contributing factors to this increased fragmentation include hydrodynamic shear forces from manual sample loading, electrical forces in the nanochannel device, and photo damage from scattered laser light. The amount of fragmentation reported here compares favorably, however, to that observed using other methods of elongation and analysis (Chan, E. Y., N. M. Goncalves, R. A. Haeusler, A. J. Hatch, J. W. Larson, A. M. Maletta, G. R. Yantz, E. D. Carstea, M. Fuchs, G. G. Wong, S. R. Gullans, and R. Gilmanshin. 2004. DNA mapping using microfluidic stretching and single-molecule detection of fluorescent site-specific tags. Genome Res. 14:1137-1146).

To estimate the resolution of the method, the mean standard error of the fitted apparent length and the real length of the intact λ-bacteriophage molecules were calculated to be 84 nm and 114 nm, respectively, from 97 molecules analyzed using model β. For higher orders of folding, the mean standard error for the real length increases: 143 nm for model γ, and 278 nm for model ε. These values can be indirectly compared with a resolution of 150 nm obtained in 1 min by Tegenfeldt et al. for a single λ-bacteriophage DNA molecule in a nanochannel at its equilibrium length of 8 μm (Tegenfeldt, J. O., C. Prinz, H. Cao, S. Chou, W. W. Reisner, R. Riehn, Y. M. Wang, E. C. Cox, J. C. Sturm, P. Silberzan, and R. H. Austin. 2004. The dynamics of genomic-length DNA molecules in 100-nm channels. Proc. Natl. Acad. Sci. U.S.A. 101:10979-10983). The values cannot be directly related, however, as the former is the average standard error of fits to single bursts, and the latter results from a Gaussian fit to a distribution of length measurements taken over a longer period of time to average out thermal fluctuations for a single molecule.

The free length of the folded molecules is of particular interest, as this is the section of the strand where the position of a site specific fluorescent label could be determined in future experiments without ambiguity. The inset in FIG. 30E shows the distribution of the free length/real length $l_F/l_R$ for all intact molecules. Of the intact molecules, 79% show a $l_F/l_R > 0.5$, meaning that in half of these cases (39.5%) any position up to the middle of the strand can be determined. This is based, however, on the assumption that half of the molecules enter the channel in the right direction (5'-end first, for example). This reduces the number of λ-bacteriophage molecules that could yield information about the site-specific position of a fluorescent tag to 26% (0.67× 0.39). The inset in FIG. 30E also justifies the interpretation of the peak value of the photon count distribution of all bursts as the result of an unfolded DNA strand occupying the focal volume, and the use of this value as a signal prefactor.

A limiting factor of the method presented in FIGS. 30A-F is the length of the focal volumes l=d/m=1.25 μm. When the length of a DNA molecule in the nanochannel was shorter than this value, the resulting fluorescent bursts did not exhibit quantized intensity levels, and the signal amplitude was determined only by the number of dye molecules which are intercalated in the strand. Eq. 7 predicts that while molecular folding would not affect the amplitude of these signals, it would be visible in a sudden variation in the slopes at the beginning and the end of the fluorescent burst. These slope changes were not detectable, however, as signal fluctuations were too high in the presented work. The α fitting model was used in this case to describe signal intensities lower than the average burst height, resulting in an apparent length value determined by peak amplitude and as a result photon count. The burst fitting and photon counting methods therefore converged for molecules shorter than 1.25 μm, which can be seen in FIG. 30D. The same limitation affected folded molecules with a folded over length of less than 1.25 μm.

Additional information, such as molecular conformation, was theoretically present as variations in the signal slopes, but its analysis was again obscured by signal fluctuations as well as any deviations from assumptions made about the optical system, such as laser illumination and fiber collection efficiency profiles. In the case of conformation, different conformations of the folded strands were described by the same fitting model, and it was not possible to determine if a burst of fluorescence with a short initial peak was the result of a strand folded over at the end, or a molecule showing a random coil configuration at the end. Although the latter configuration has been found in microchannel structures for DNA stretching (Tegenfeldt, J. O., O. Bakajin, C. F. Chou, S. S. Chan, R. Austin, W. Fann, L. Liou, E. Chan, T. Duke, and E. C. Cox. 2001. Near-field scanner for moving molecules. Phys. Rev. Lett. 86:1378-1381) it was not described in DNA translocation experiments using 10 to 20 nm pores (Li, J. L., M. Gershow, D. Stein, E. Brandin, and J. A. Golovchenko. 2003. DNA molecules and configurations in a solid-state nanopore microscope. Nat. Mater. 2:611-615) nor was it found in optical investigations of longer DNA molecules in 100 nm nanochannels (Mannion, J. T., C. H. Reccius, J. D. Cross, and H. G. Craighead. 2006. Conformational analysis of single DNA molecules undergoing entropically induced motion in nanochannels. Biophys. J. 90:4538-4545). Further insight into the conformation of smaller molecules could be gained by reducing the length of the focal volume. This could be achieved by using smaller fiber diameters, by using an objective with higher magnification (with the resulting reduction in spot distance for the optical setup used here) or by combining nanochannels with optical nanoslits for near field microscopy (Tegenfeldt, J. O., O. Bakajin, C. F. Chou, S. S. Chan, R. Austin, W. Fann, L. Liou, E. Chan, T. Duke, and E. C. Cox. 2001. Near-field scanner for moving molecules. Phys. Rev. Lett. 86:1378-1381). Velocity information was also present in the signal slopes, and its analysis was similarly limited. This limit was overcome, however, by fitting partner busts simultaneously, in which case the time of travel between the focal volumes dominated the determination of velocity due to its large effect on the combined fit.

Previous work involving DNA stretching and analysis has made use of hydrodynamic forces to elongate DNA and subsequently determine the position of fluorescent peptide nucleic acid tags bound to specific motif sites, yielding sequence information about the strand (Perkins, T. T., D. E. Smith, and S. Chu. 1997. Single polymer dynamics in an elongational flow. Science 276:2016-2021; Phillips, K. M., J. W. Larson, G. R. Yantz, C. M. D'Antoni, M. V. Gallo, K. A. Gillis, N. M. Goncalves, L. A. Neely, S. R. Gullans, and R. Gilmanshin. 2005. Application of single molecule technology to rapidly map long DNA and study the conformation of stretched DNA. Nucleic Acids Res. 33:5829-5837). Although this method is able to fully stretch DNA strands, the fluidic channels used were inhomogeneously illuminated. As shown here, dynamic electrophoretic stretching in nanochannels is not yet optimized to yield fully stretched strands, but achieves uniform illumination across the nanochannel. This increases excitation uniformity and enables the determination of the DNA conformation by analytic fitting, theoretically permitting even the use of folded strands for the determination of site-specific information. Uniform illumination also yields more accurate fragment sizing based on photon counting, which leads to a higher percentage of molecules that can be confirmed as intact. This is achieved without the velocity correction of the photon count as often used in hydrodynamic stretching (Phillips, K.

M., J. W. Larson, G. R. Yantz, C. M. D'Antoni, M. V. Gallo, K. A. Gillis, N. M. Goncalves, L. A. Neely, S. R. Gullans, and R. Gilmanshin. 2005. Application of single molecule technology to rapidly map long DNA and study the conformation of stretched DNA. Nucleic Acids Res. 33:5829-5837; Chan, E. Y., N. M. Goncalves, R. A. Haeusler, A. J. Hatch, J. W. Larson, A. M. Maletta, G. R. Yantz, E. D. Carstea, M. Fuchs, G. G. Wong, S. R. Gullans, and R. Gilmanshin. 2004. DNA mapping using microfluidic stretching and single-molecule detection of fluorescent site-specific tags. Genome Res. 14:1137-1146).

Electrodynamic stretching was also observed to be uniform along the length of the nanochannel, although the molecules were not completely elongated. This means that even at speeds an order of magnitude smaller than in hydrodynamic stretching, tag positions could be determined using the stronger fluorescent signals resulting from longer illumination times. Further electrodynamic stretching of the strands could most likely be achieved by the creation of stronger electric field gradients at the entrance of the nanochannel. Gradients of at least an order of magnitude stronger can be achieved either by the use of smaller nanochannels, the connection of fewer parallel nanochannels to the nanoslit or increasing the depth of the nanoslit. The fabrication of 10 nm nanochannels has already been shown (Cao, H., Z. N. Yu, J. Wang, J. O. Tegenfeldt, R. H. Austin, E. Chen. W. Wu, and S. Y. Chou. 2002. Fabrication of 10 nm enclosed nanofluidic channels. Appl. Phys. Lett. 81:174-176) as well as the repetitive translation of DNA molecules from nanoslits to microchannels (Han, J. and H. G. Craighead. 1999. Entropic trapping and sieving of long DNA molecules in a nanofluidic channel. J. Vac. Sci. Technol. A-Vac. Surf. Films 17:2142-2147; Han, J. and H. G. Craighead. 2000. Separation of long DNA molecules in a microfabricated entropic trap array. Science 288:1026-1029) have already been shown.

Dependence of Molecular Speed on Degree of Folding

To investigate the effects of DNA folding on speed, the results of three subsequent 1 min runs of λ-bacteriophage DNA (including the experiment shown in FIGS. 30A-F) at a device bias of U=50V were combined. FIG. 31A shows the distribution of the speed $v_S$ versus the apparent length/real length $l_A/l_R$ for 752 intact λ-bacteriophage DNA molecules. Molecules with increased folding and therefore smaller $l_A/l_R$ had a slightly higher speed $v_S$. The speed distribution $v_S$ is also plotted as a function of the number of folds in the strands in FIG. 31B. The number of folds for each molecule was determined by the analytical model chosen to describe its resulting fluorescent burst. The overall influence of folding was found to be weak. Unfolded molecules were rare, resulting in just two data points, and molecules with three folds were observed to have a slightly higher speed $v_S$ than molecules with one or two folds. This could be the result of increased hydrodynamic interactions between the parallel strands of the folded molecules. As electrophoretically driven DNA molecules are supposed to be free draining, these hydrodynamic interactions might take place only when the strand segments are very close, explaining the weakness of the effect. But molecular dynamics simulations may be necessary to fully explain this result.

Dependence of Molecular Speed, Mobility and Friction on Device Bias

To investigate the effects of device bias on molecule speed and length, molecules from a λ-bacteriophage DNA sample were driven through a nanochannel at several different device biases U. Five continuous runs were performed for each device bias, and the cross correlation curves as well as the single bursts of fluorescence were analyzed by use of the respective models. The average single-molecule speed $\bar{v}_S$ is plotted as a function of device bias U in FIG. 32A. A linear fit of $\bar{v}_S(U)$ yields a slope of $m_S$=60.9±1.4 μm/(Vs), confirming that speed increases linearly with device bias and electric field, as expected. For comparison, a plot of the speed $\bar{v}_C(U)$ resulting from the cross correlation functions is added to the figure, and shows a very similar slope of $m_C$=61.0±0.7 μm/(Vs).

The ratio of the electric field E inside one of the nanochannels to the device bias U was calculated from device dimensions to be 31 cm$^{-1}$. Dividing the slope of the linear fit of $\bar{v}_S(U)$ by this ratio gives the mobility of a DNA molecule as $\mu_S=\bar{v}_S/E$=2.0×10$^{-4}$ cm$^2$/(Vs). Assuming a charge per unit length of λ=1.1 e$_0$/nm for the labeled DNA molecules (30), and considering that folding seems to have only a slight effect on speed, the friction coefficient per unit contour length was estimated to be $\xi_S=\lambda/\mu_S$=9.3 fNs/μm$^2$. This is close to the 10.0 fNs/μ$^2$ found in similar nanochannel devices (Mannion, J. T., C. H. Reccius, J. D. Cross, and H. G. Craighead. 2006. Conformational analysis of single DNA molecules undergoing entropically induced motion in nanochannels. Biophys. J. 90:4538-4545). This calculation can be viewed only as an approximation, however, as some parallel channels to the investigated channel showed unintended constrictions with unknown influence on the real electric field in this particular device.

Dependence of Stretching on Device Bias

FIG. 32B illustrates the variation of real length of the DNA strands with increasing device bias. Because of the fragmentation of the λ-bacteriophage DNA molecules, the results for the single-molecule length are plotted as grayscale intensity distributions instead of the mean values. As the number of molecules per distribution varied between ~140 and ~1200 molecules, the real length distributions are shown normalized for each device bias. In rough terms, the maximum of the real length distributions, corresponding to the majority of intact λ-bacteriophage DNA strands, remains constant until ~10 V. An increase in real length is then observed until ~75 V, followed by a plateau at higher device biases. A complete explanation for this trend is beyond the scope of this study and must account for DNA stretching as a result of entrance effects and entropic confinement in the nanochannel, as well as hydrodynamic and channel surface friction. The average length $\bar{l}_C$ resulting from cross correlation analysis is plotted as an overlay to the single molecule distributions. The increasing trend from the single molecule distributions is not as evident, as the single molecule analysis routine accounts for folding and fragmentation of the molecules neglected by the correlation analysis.

Dependence of Length and Speed on DNA Size

An experiment was performed in order to test the sensitivity of the method, compare it to previously demonstrated techniques based on intensity measurements, and determine the dependence of DNA speed on the number of base pairs in a nanochannel. This dependence is of interest for the development of theory regarding the electrophoresis of DNA confined to nanoscale environments, and for applications that exploit DNA size dependence to achieve biomolecular separation. A sample with a broad size range of DNA molecules was prepared by mixing λ-bacteriophage DNA in equal parts with its own HindIII digest. The resulting mixture contained nine primary types of DNA molecules (in base pairs: 125, 564, 2,027, 2,322, 4,361, 6,557, 9,416, 23,130, and 48,502). More than 16,000 molecules were detected in a 2 min experiment and automatically analyzed, the results of which are presented in FIGS. 33A-F. Almost all the scattered data points were the result of overlapping molecules following Poisson focal volume occupation statistics (Foquet, M., J. Korlach, W. Zipfel, W. W. Webb, and H. G. Craighead. 2002. DNA fragment sizing by single molecule detection in submicrometer-sized closed fluidic channels. Anal. Chem. 74:1415-1422).

Two other phenomena were observed in this experiment which required modifications to the analysis algorithm as described previously. The second photon burst consistently molecule detection in submicrometer-sized closed fluidic channels. Anal. Chem. 74:1415-1422), although the sample was heated to avoid this effect. This peak is not observed in FIG. 8E, due to the lower resolution of inferring DNA size through photon count at longer DNA lengths.

The fit results for these peak positions and relative standard deviations are shown in Table 1.

TABLE 1

Fitting Results for FIGS. 33A and 33E.

| Peak in 7A | Peak in 7E | DNA strand size [bp] | Percentage of molecules in 7A | Real length $l_R$ [μm] | Relative standard deviation of $l_R$ [%] | Counts per molecule [cnts] | Relative standard deviation of counts [%] |
|---|---|---|---|---|---|---|---|
| 1 | 1 | 125 | 9.5 | 0.0182 | 56 | 57.1 | 44 |
| 2 | 2 | 564 | 12 | 0.0927 | 24 | 257 | 24 |
| 3 | 3 | (2027 + 2322)/2 | 25 | 0.454 | 15 | 1250 | 15 |
| 4 | 4 | 4361 | 9.4 | 1.10 | 11 | 2880 | 8.7 |
| 5 | 5 | 6557 | 11 | 1.70 | 7.1 | 4280 | 7.0 |
| 6 | 6 | 9416 | 11 | 2.51 | 6.6 | 6310 | 6.3 |
| 7 | 7 | 23130 | 6.0 | 4.77 | 4.2 | 13200 | 11 |
| 8 | / | 23130 + 4361 | 2.7 | 5.71 | 6.6 | — | — |
| 9 | 8 | 48502 | 3.3 | 13.1 | 6.1 | 24800 | 6.9 | exhibited increased folding, which was addressed by allowing different folding factors for the partner bursts. This was most likely the result of increased nanochannel surface roughness between the two focal volumes (Reccius, C. H., J. T. Mannion, J. D. Cross, and H. G. Craighead. 2005. Compression and free expansion of single DNA molecules in nanochannels. Phys. Rev. Lett. 95:2681011-2681014). The longest DNA molecules also had a lower than expected photon count and burst height, which was accounted for by choosing a smaller fit amplitude for molecules with counts over 20,000 photons. This was attributed to the lower mobility of longer DNA strands in the nanoslit, with a resulting increase in the observed loss of dye molecules to the nanoslit surfaces, and photobleaching by scattered laser light. Although this mobility effect was observed previously only in shallower nanoslits (Cross, J. D., E. A. Strychalski, and H. G. Craighead. 2007. Size-dependent DNA mobility in nanochannels. J. Appl. Phys. 102:247011-247015), a similar outcome may have occurred here because of the rougher nanoslit channel surfaces.

The sample also contained a small fraction of λ-bacteriophage DNA multimers which were observed at higher photon counts and with longer length than visualized in FIGS. 33A-F. FIG. 33D shows a color coded intensity histogram of photon counts per molecule versus real length $l_R$. The distributions of real length and photon count per molecule are plotted in FIG. 33A and FIG. 33E, respectively. The distributions in FIGS. 33A and 33E were fitted with superpositions of 9 and 8 logarithmically modified Gaussians, respectively, as described in Eq. 14. In both plots, peak 3 was interpreted as a combined peak of the 2,027 bp and 2,322 bp fragments, per the analysis of Foquet et al. (Foquet, M., J. Korlach, W. Zipfel, W. W. Webb, and H. G. Craighead. 2002. DNA fragment sizing by single molecule detection in submicrometer-sized closed fluidic channels. Anal. Chem. 74:1415-1422). Peak 8 in FIG. 33A results from a fraction of the 4,361 bp and 23,130 bp fragments annealing at the complementary ends and creating an additional 27,491 by fragment (Foquet, M., J. Korlach, W. Zipfel, W. W. Webb, and H. G. Craighead. 2002. DNA fragment sizing by single In FIGS. 33A and 33E, multiple peaks were observed and matched with the known DNA strand sizes. Fitting the real length distribution in FIG. 33A gives the real length $l_R$ and the standard deviation of the different strand sizes. Fitting the counts per molecule distribution in FIG. 33E gives the counts per molecule and standard deviations. The percentage of molecules was derived from FIG. 33A.

The relative standard deviations decrease in a sigmoidal fashion (not shown) with increasing strand size for both fits, with the exception of peak 7 in FIG. 33E, as it contains unresolved 27,491 bp DNA strands which are fitted as a separate peak in FIG. 33A. The resolution for both measures increases for longer molecules, as opposed to gel electrophoresis. This was also observed in previous photon count measurements, and is related to the fact that fluctuations in dye fluorescence, detection efficiency and in the number of dye molecules attached to strands of equal size obey Poisson statistics (Foquet, M., J. Korlach, W. Zipfel, W. W. Webb, and H. G. Craighead. 2002. DNA fragment sizing by single molecule detection in submicrometer-sized closed fluidic channels. Anal. Chem. 74:1415-1422; Chou, H. P., C. Spence, A. Scherer, and S. Quake. 1999. A microfabricated device for sizing and sorting DNA molecules. Proc. Natl. Acad. Sci. U.S.A. 96:11-13). These fluctuations influence the quality of the burst fits in a similar fashion and therefore lead to a similar resolution increase for longer strands. Because dye binding is sequence dependent, the number of dye molecules bound to a strand did not reach equilibrium because of the low off-rate of YOYO-1 from DNA. Both phenomena negatively affected the resolution. The measured real length of 13.1 μm for λ-bacteriophage DNA was found to be longer than in the experiments shown in FIGS. 30A-F and FIGS. 32A-B.

These experiments were performed in different devices, which may have different channel widths, particularly at the critical channel entrance. In FIG. 33B and FIG. 33C the mean length and the mean photon counts per molecule for the fitted peaks were plotted against the assumed number of base pairs for the fragments. The resulting dependence was well described by a linear fit, underscoring the fact that each peak corresponded to the expected fragment. This also indicates that the stretching factor $s=l_R/L$ is independent of strand length.

The slopes of the fits were $m_{IR}=0.24\pm0.01$ nm/bp and $m_C=0.63\pm0.02$ cnts/bp. The latter is a factor of four smaller than the 2.5 cnts/bp that was achieved by Foquet et al (Foquet, M., J. Korlach, W. Zipfel, W. W. Webb, and H. G. Craighead. 2002. DNA fragment sizing by single molecule detection in submicrometer-sized closed fluidic channels. Anal. Chem. 74:1415-1422), which is due to the use of different optical components including smaller optical fibers and increased adsorption of the dye molecules to the nanoslit surfaces. Despite this lower detection efficiency, a fraction of the smallest fragment of the λ-HindIII digest was resolved due to decreased noise from a smaller nanochannel and the use of two focal volumes.

The second photon count signal had a filtering effect, as fluorescent bursts without partners in the time range predicted by cross correlation analysis were discarded. This allowed time range was about an order of magnitude larger than the observed time difference variation and did not influence the distributions. The photon count for the longest DNA molecules in FIG. 33C lies significantly below the linear fit, as a result of increased dye loss and photobleaching for this molecule in the device used here.

The percentage of the total molecules detected in each peak is also reported in Table 1. Considering annealing effects (see, e.g., Foquet, M., J. Korlach, W. Zipfel, W. W. Webb, and H. G. Craighead. 2002. DNA fragment sizing by single molecule detection in submicrometer-sized closed fluidic channels. Anal. Chem. 74:1415-1422), peaks 1-8 comprise the expected percentages of the total count. Peak 1 has a reduced value due to the high single molecule detection threshold, and peak 9 is reduced due to the retardation of long molecules in the nanoslit.

Neglecting λ-bacteriophage molecules, the total percentage of intact digest fragments in these peaks was calculated to be 82%, based on the results shown in FIG. 33A. The same value was determined to be 81% using agarose gel electrophoresis. This higher percentage of intact molecules, as compared to λ-bacteriophage DNA, results from random fragments coinciding with digested fragment peaks.

FIG. 33F is a color, coded intensity histogram (here shown in gray scale) of the number of molecules against the molecule speed $v_S$ and the real length $l_R$. This measurement was repeated for device biases of 25V and 100V (results not shown) and the same trend was observed, which was also similar to that observed for DNA molecules of comparable lengths in free solution (Stellwagen, N. C., C. Gelfi, and P. G. Righetti. 1997. The Free Solution Mobility of DNA. Biopolymers 42:687-703). This indicates that the deformation from the random coil shape of unconfined DNA into the elongated and stretched conformation has a negligible influence on the speed of strands with length longer than the channel width.

The smallest fragment (125 bp) was observed to have a slightly lower speed; a similar trend was observed around 100 bp in free solution (Stigter, D. 2002. Wall effects on DNA stretch and relaxation. Biophysical Chemistry 101:447-459), and attributed to electrolyte friction. It could also be related here to DNA lengths which are smaller than the width and depth of the nanochannel, permitting molecular orientations more transverse to the channel length which result in increased hydrodynamic friction. These orientations are denied to longer molecules, as the known stiffness of double-stranded DNA characterized by its persistence length results in an orientation more aligned to the channel axis.

To correctly interpret shorter DNA fragments with apparent length smaller than the focal volume length $d/m=50$ μm/40=1.25 μm, the prefactors $p_{0,1}$ and $p_{0,2}$ of the fitting formulas must be accurately predetermined. This was possible only if the burst height for single unfolded DNA strands remained constant throughout the experiment. The time limit for this was found to be ~2 min as a result of stage or laser drift, which limited the number of molecules detected at lower voltages. Another limit was related to the device loading time. The fluorescence intensity of the molecules was found to decrease with the time the DNA molecules spent in the nanoslit region of the device, even before being directly exposed to the focused lasers. Explanations for this effect include photobleaching by scattered or reflected laser light, or loss of positively charged YOYO-1 dye molecules attracted to the negatively charged channel walls. Increasing channel background fluorescence was indeed observed after the nanochannel outlets, although the solution contained PVP to dynamically coat the channel surfaces and reduce interactions. This phenomenon was particularly evident with the device used in the experiment shown in FIGS. 33A-F.

6.5.5 Conclusion

This example presents a method to rapidly analyze fluorescently labeled DNA molecules, and several experiments investigating the physics of DNA in nanochannels were performed. DNA molecules were driven electrophoretically from a nanoslit into a nanochannel to confine and dynamically elongate the strands beyond their equilibrium conformation. Two lasers were focused sequentially along the length of the nanochannel to induce bursts of fluorescence from the molecules. These bursts showed multiple intensity levels indicative of folding, and the collected photon count signals were analyzed with various analytical fitting models which yielded molecular conformation, length, and speed of single DNA strands.

Molecular length was determined both by fitting each fluorescent burst shape to analytical models and by photon counting. While counting photons was simpler, modeling and fitting the bursts yielded better resolution for longer strands for the optical setup used here, and has several other advantages for analyzing unknown samples: no calibration sample is needed for burst shape fitting, and it is less affected by excitation intensity and variations in fluorescent labeling. The resolution for λ-bacteriophage DNA with one fold at the front end was 114 nm for individual molecules with a mean real length of 11 μm, and the analysis time was ~20 ms per molecule. The speed of the molecules was found to increase only slightly with folding. A possible cause of this trend is increased hydrodynamic interactions between strand segments in proximity. Deeper insight into the influence of hydrodynamic friction and surface interactions on the molecule speed could be achieved by molecular dynamics simulations. DNA stretching was found to increase with applied device bias and electric field, which was estimated from device dimensions to be 56 times higher in the nanochannels than in the nanoslit.

The analysis of a mixture of λ-bacteriophage with its own HindIII digest demonstrated that our method can identify, by length, 9 of 10 fragments ranging over 2.5 orders of magnitude in size. When compared to standard agarose gel electrophoresis, longer strands (>20 kbp) can be analyzed, the measurement time is at least 30 times faster and much less sample is consumed. Although resolution decreases with size for agarose gels, the opposite is found for this method. DNA speed was found to be almost constant for all fragments investigated, showing only a slight decrease for short fragments. Confinement, elongation and interaction with channel surfaces did not lead to a significant size dependent influence on speed.

Information can also be obtained pertaining to the length and conformation of molecules shorter than the focal volume length that is present in the signal start and end slopes, but that is currently obscured by signal fluctuations. This can be achieved by further elongating the DNA molecules by using smaller nanochannels, which would lead to a higher uniformity of basepair density along the channel. This will yield fluorescence signals with smaller fluctuations, leading to improved length determination using the method here. The accuracy of other physical information such as molecular conformation and speed will also increase, leading to more insight into the behavior of DNA molecules in highly constrained environments. As burst fitting can provide spatial information beyond the diffraction limit, the method described here can be used for extremely rapid and ultrahigh spatial resolution measurements. Other applications are the position of a site-specific label and biophysical effects such as knot formation. As this label or knot may fall in a folded over segment of DNA, with a resulting ambiguous position, models must be developed to extract positional information. The analysis of samples containing longer DNA strands can use photon burst fitting models that account for the increased probability of more complicated folding conformations and knot formation.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. An electrical detector for detecting a single charged molecule or particle of interest or a plurality of charged molecules or particles of interest comprising:
a nanofluidic channel or plurality of nanofluidic channels, wherein the channel depth of each nanofluidic channel is smaller than, on the order of, or 2-10 times the Debye screening length;
a source and drain electrode pair or a plurality of source and drain electrode pairs,
a charge sensor or a plurality of charge sensors associated with each nanofluidic channel, wherein:
the charge sensor or each charge sensor in the plurality of charge sensors is one continuous individually addressable nanowire or one continuous individually addressable nanotube,
the charge sensor or each charge sensor in the plurality of charge sensors is electrically connected by electrical contacts to, and is addressable by, a single source and drain electrode pair; and
at least one portion of the charge sensor or of each charge sensor in the plurality of charge sensors is in the interior of the nanofluidic channel, whereby the charge sensor or each charge sensor in the plurality of charge sensors is contacted by fluid in the nanofluidic channel.

2. The electrical detector of claim 1, wherein the plurality of nanofluidic channels is 2-10, 10-50, 50-100, 100-500, 500-1000, or 1000-5000 channels.

3. The electrical detector of claim 1 wherein the width of the nanofluidic channel(s) is 0.1 nm 1 nm, 1 nm-5 nm, 5 nm-10 nm, 10 nm-50 nm, 50 nm-100 nm, 100 nm-500 nm, 500 nm-1 µm, 1 µm-5 µm or 5 µm-10 µm.

4. The electrical detector of claim 1 wherein the nanotube is a p-type or n-type nanotube.

5. The electrical detector of claim 1 comprising a microfluidic or macrofluidic structure fluidically connected to the nanofluidic channel or channels.

6. The electrical detector of claim 1, wherein the charge sensor, or at least one of the charge sensors in the plurality of charge sensors, is an addressable semiconducting charge sensor that behaves as an electrolyte gated field effect transistor.

7. The electrical detector of claim 1, wherein the charge sensor or sensors is or are functionalized.

8. The electrical detector of claim 7 wherein the charge sensor or sensors is or are functionalized with a molecule selected from the group consisting of an antibody, a portion of an antibody, and an oligonucleotide.

9. The electrical detector of claim 1 comprising a substrate.

10. The electrical detector of claim 1 wherein:
a constant source-drain bias voltage is applied with a constant source-drain bias voltage applicator, and
current through the charge sensor or sensors is monitored.

11. The electrical detector of claim 1 wherein the dimensions of the nanofluidic channel or channels constrain or confine—the single charged molecule or particle of interest or the plurality of charged molecules or particles of interest to within a sensing range of the charge sensor.

12. A method for detecting a biological or chemical species of interest or a tag associated with the species comprising:
providing the electrical detector of claim 1;
flowing the species or an entity comprising the species through the nanofluidic channel or a nanofluidic channel of the plurality of nanofluidic channels of the electrical detector; and
contacting the charge sensor or a charge sensor of the plurality of the charge sensors with the species or the tag, thereby producing a detectable signal indicative of the presence of the biological or chemical species of interest.

13. A method for detecting a local solution potential of interest comprising:
providing the electrical detector of claim 1;
flowing the solution through the nanofluidic channel or a nanofluidic channel of the plurality of nanofluidic channels of the electrical detector; and
contacting the charge sensor or a charge sensor of the plurality of the charge sensors with the solution, thereby producing a detectable local solution potential signal.

14. The electrical detector of claim 1, additionally comprising:
an insulator insulating electrical contacts of:
the source electrode and the drain electrode of the source and drain electrode pair, or a source electrode and a drain electrode of a source and drain electrode pair of the plurality of source and drain electrode pairs.

15. The electrical detector of claim 1, wherein the charge sensor or each charge sensor in the plurality of charge sensors is located on a bottom surface of the nanofluidic channel or on a bottom surface of each of the nanofluidic channels in the plurality of nanofluidic channels, thereby allowing the single charged molecule or particle of interest or the plurality of charged molecules or particles of interest to pass above the charge sensor or the plurality of charge sensors located on the bottom surface of the nanofluidic channel or on the bottom surface of each of the nanofluidic channels in the plurality of nanofluidic channels.

* * * * *